(12) United States Patent
Carroll et al.

(10) Patent No.: US 10,040,766 B2
(45) Date of Patent: Aug. 7, 2018

(54) UBIQUITINATION INHIBITORS

(71) Applicant: Rigel Pharmaceuticals, Inc., South San Francisco, CA (US)

(72) Inventors: David Carroll, San Francisco, CA (US); Arvinder Sran, Fremont, CA (US); Rajinder Singh, Belmont, CA (US); Jianing Huang, Foster City, CA (US); Lyuben Tsvetkov, Foster City, CA (US); Sarkiz Issakani, Redwood City, CA (US); Donald Payan, Hillsborough, CA (US); Simon Shaw, Oakland, CA (US)

(73) Assignee: RIGEL PHARMACEUTICALS, INC., South San Francisco, CA (US)

( * ) Notice: Subject to any disclaimer, the term of this patent is extended or adjusted under 35 U.S.C. 154(b) by 0 days.

(21) Appl. No.: 14/826,281

(22) Filed: Aug. 14, 2015

(65) Prior Publication Data

US 2016/0068490 A1    Mar. 10, 2016

Related U.S. Application Data

(60) Provisional application No. 62/037,449, filed on Aug. 14, 2014.

(51) Int. Cl.
| | |
|---|---|
| C07D 401/12 | (2006.01) |
| C07D 215/40 | (2006.01) |
| C07D 401/14 | (2006.01) |
| C07D 401/04 | (2006.01) |
| C07D 405/04 | (2006.01) |
| C07D 409/04 | (2006.01) |

(52) U.S. Cl.
CPC ......... *C07D 215/40* (2013.01); *C07D 401/04* (2013.01); *C07D 401/12* (2013.01); *C07D 401/14* (2013.01); *C07D 405/04* (2013.01); *C07D 409/04* (2013.01)

(58) Field of Classification Search
USPC .......... 514/235, 253.06, 646, 235.5
See application file for complete search history.

(56) References Cited

U.S. PATENT DOCUMENTS

| | | | |
|---|---|---|---|
| 2005/0009871 A1 | 1/2005 | Ramesh et al. | |
| 2007/0254894 A1* | 11/2007 | Kane ............. | C07D 401/12 514/253.06 |
| 2012/0214803 A1* | 8/2012 | Buhr .............. | C07D 215/40 514/222.8 |

FOREIGN PATENT DOCUMENTS

| | | |
|---|---|---|
| WO | 2008/074068 A1 | 6/2008 |
| WO | 2012/122534 A2 | 9/2012 |
| WO | 2013/052943 A2 | 4/2013 |

OTHER PUBLICATIONS

Shridhar Bhat et al, "Substituted oxines inhibit endothelial cell proliferation and angiogenesis," Organic & biomolecular chemistry, vol. 10, No. 15, Jan. 1, 2012, p. 2979.
Sung Keon Namgoong et al, "Synthesis of the Quinoline-Linked Triazolopyrimidine Analogues and Their Interactions with the Recombinant Tobacco Acetolactate Synthase," Biochemical and Biophysical Research Communications, vol. 258, No. 3, May 1, 1999, pp. 797-801.
Database Registry (Online) Chemical Abstracts Service, Jul. 15, 2004, Database accession No. 710307-72-5.
Database Registry (Online) Chemical Abstracts Service, Dec. 18, 2007, Database accession No. 958585-17-6.
International Search Report and Written Opinion dated Sep. 24, 2015 for PCT Application No. PCT/US2015/045174 filed Aug. 14, 2015.

* cited by examiner

*Primary Examiner* — Pancham Bakshi
(74) *Attorney, Agent, or Firm* — McDonnell Boehnen Hulbert & Berghoff LLP; Travis Young

(57) ABSTRACT

Disclosed are sulfonamidoquinoline compounds, as well as pharmaceutical compositions and methods of use. One embodiment is a compound having the structure

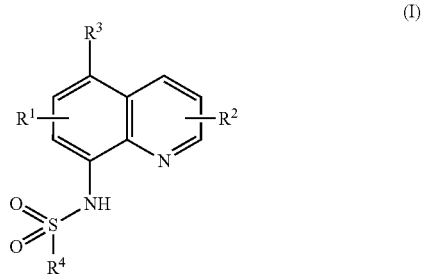

(I)

and pharmaceutically acceptable salts, prodrugs and N-oxides thereof (and solvates and hydrates thereof), wherein $R^1$, $R^2$, $R^3$ and $R^4$ are as described herein. In certain embodiments, a compound disclosed herein inhibits ubiquitination, and can be used to treat disease by blocking the degradation of tumor suppressors.

16 Claims, No Drawings

UBIQUITINATION INHIBITORS

CROSS REFERENCE TO RELATED APPLICATIONS

This application claims priority to U.S. Provisional Patent Application No. 62/037,449, filed on Aug. 14, 2014, which is hereby incorporated herein by reference in its entirety.

BACKGROUND

Field of Invention

This invention comprises compounds, pharmaceutical compositions and methods of use of the compounds and compositions containing them. This invention relates more particularly to certain sulfonamidoquinoline compounds and pharmaceutical compositions thereof, and to methods of inhibiting ubiquitination. Further methods comprise treating and/or preventing disease using certain sulfonamidoquinoline compounds to block the degradation of tumor suppressors.

Technical Background

Ubiquitination of a protein provides a signal for its targeted degradation and recycling via the ubiquitin-proteasome pathway. The process of ubiquitination takes place in a series of steps, beginning with the activation of ubiquitin through a ubiquitin-activating enzyme E1 and the transfer to a ubiquitin-conjugating enzyme E2. Finally the ubiquitin is linked to the lysine of the target protein in the presence of an ubiquitin-protein ligase E3 (referred to as a ubiquitin ligase). Chains of four or more ubiquitin domains activates the degradation process by the proteasome.

The E3 ubiquitin ligase acts as a substrate recognition module for the ubiquitination system in which each E3 provides specificity for only a small number of substrates. This specificity makes E3 ligases attractive targets for drug discovery (analogous to kinases), for instance by preventing degradation of pro-apoptotic proteins in cancer cells.

The development of small molecule E3 ligase inhibitors is challenging due to the requirement of the molecules to disrupt protein-protein interactions (PPI's). PPI's are an area that has not been well explored in small-molecule drug-discovery because the interaction surfaces are often large with flat or shallow grooves at the interfaces. This is in contrast to the tight, well defined pockets present in traditional enzymes or receptors. However, it has the potential to be rewarding and is beginning to be recognized, and there have been several examples of the disruption of E3 ligase binding. One of the initial investigations in this area came from work on the disruption of binding between p53 and MDM2. MDM2 serves as the E3 ligase for p53 promoting degradation. The work resulted in the identification of cis-imidazolines known as Nutlins, which displace p53 from its complex with MDM2 in the 100-300 nM range. These efforts have spurred an effort to develop structure-activity relationships (SAR) around these and similar structures, resulting in compounds that inhibit the p53-MDM2 interaction with single digit nanomolar potencies and below. Further, there have been several reports of small molecules being used to target E3 ligases including the von Hippel-Lindau ligase to disrupt the VHL-HIF-1α interaction as well as a non-ligase PPI between HIF1α and HIF1α.

The Skp1-Cullin 1-F-Box (SCF) family of E3 ligases are a well characterized family held together through PPI's. The complex consists of the scaffold protein Cullin-1, which binds Roc1 (recruiting the E2) and Skp1 (recruiting the F-Box protein). One particular E3 ligase complex is responsible for p27, the substrate recognition component Skp2 and an adaptor protein Cks1. p27, a CDK inhibitor, is a negative regulator of cell cycle progression. Low levels of p27 have been implicated in a number of cancers, while elevated levels of Cks1 have been associated with low levels of p27 and poor prognosis in cancer patients. There have been several groups that have targeted the SCF ligases with the goal of increasing levels of p27. Molecules have also been identified as disrupting PPI's between Skp1-Skp2 and Skp2-Cks1-p27, and as interacting with alternative E3 ligases in the SCF system including Cdc4, Met30 and βTRCP1. There have not been any reports of compounds targeted to the Cks1-Skp2 PPI.

SUMMARY

The present invention comprises compounds, pharmaceutical compositions and methods of using them to treat and/or prevent disease by inhibiting ubiquitination.

Disclosed herein are compounds having structural formula (I)

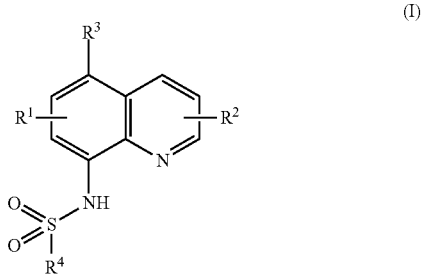

and pharmaceutically acceptable salts, prodrugs and N-oxides thereof (and solvates and hydrates thereof), wherein $R^1$, $R^2$, $R^3$ and $R^4$ are as described herein.

Also disclosed herein are pharmaceutical compositions. Examples of such compositions include those having at least one pharmaceutically acceptable carrier, diluent or excipient; and a compound, pharmaceutically acceptable salt, prodrug or N-oxide (or solvate or hydrate) as described herein.

Another aspect of the present invention comprises methods for treating and/or preventing disease by blocking the degradation of tumor suppressors. Accordingly, the invention also comprises methods for treating disease using the presently disclosed compounds and pharmaceutical compositions.

The compounds of the invention inhibit Cks1-Skp2 PPI and ubiquitination, and they increase levels of p27.

DETAILED DESCRIPTION

In one aspect, the invention comprises compounds that inhibit ubiquitination.

In embodiment $I_1$ of this first aspect, the compounds have structural formula (I):

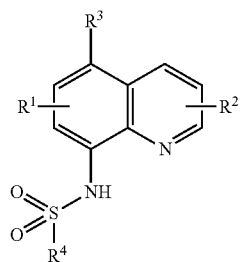

and pharmaceutically acceptable salts, prodrugs and N-oxides thereof, and solvates and hydrates thereof,
wherein
$R^1$ is -hydrogen, —($C_1$-$C_6$ haloalkyl), —Y—($C_1$-$C_6$ haloalkyl), —Y—($C_0$-$C_6$ alkyl)-Ar, —Y—($C_0$-$C_6$ alkyl)-Het, —Y—($C_0$-$C_6$ alkyl)-Cak, —Y—($C_0$-$C_6$ alkyl)-Hca, -halogen, —$NO_2$ or —CN,
wherein Y is O, S, N($R^5$), and $R^5$ is -hydrogen or —($C_1$-$C_6$ alkyl);
$R^2$ is -hydrogen, —($C_1$-$C_6$ alkyl), —($C_1$-$C_6$ haloalkyl), —Y—($C_1$-$C_6$ alkyl), —Y—($C_1$-$C_6$ haloalkyl), -halogen, —$NO_2$ or —CN;
wherein Y is O, S, N($R^5$), and $R^5$ is -hydrogen or —($C_1$-$C_6$ alkyl);
$R^3$ is -hydrogen, —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, -halogen, —$NO_2$ or —CN; and
$R^4$ is —($C_1$-$C_6$ alkyl), —($C_1$-$C_6$ haloalkyl), —($C_0$-$C_6$ alkyl)-Ar, —($C_0$-$C_6$ alkyl)-Het or —($C_0$-$C_6$ alkyl)-Cak,
wherein
each Ar (aryl), Het (heteroaryl), Cak (cycloalkyl), Hca (heterocycloalkyl),
alkyl, and haloalkyl is optionally substituted,
provided that:
at least one of $R^1$ and $R^3$ is not hydrogen.

Embodiment $I_2$ comprises compounds of embodiment $I_1$, provided that the compound is not:
N-(5-bromoquinolin-8-yl)-4-methylbenzenesulfonamide
N-(6-chloroquinolin-8-yl)benzenesulfonamide;
N-(5,7-dichloroquinolin-8-yl)-4-methylbenzenesulfonamide;
N-(5,7-dichloroquinolin-8-yl)-2,4,6-trimethylbenzenesulfonamide;
N-(6-fluoroquinolin-8-yl)benzenesulfonamide;
N-(5-chloro-6-fluoroquinolin-8-yl)benzenesulfonamide;
N-(6-(trifluoromethoxy)quinolin-8-yl)benzenesulfonamide;
2,6-difluoro-N-(6-fluoroquinolin-8-yl)benzenesulfonamide;
4-chloro-2-fluoro-N-(6-fluoroquinolin-8-yl)benzenesulfonamide;
N-(6-fluoroquinolin-8-yl)pyridine-3-sulfonamide;
N-(5,6-difluoroquinolin-8-yl)benzenesulfonamide;
N-(7-chloroquinolin-8-yl)benzenesulfonamide;
N-(6-(trifluoromethoxy)quinolin-8-yl)-6-(trifluoromethyl)pyridine-3-sulfonamide;
N-(6-(trifluoromethoxy)quinolin-8-yl)pyridine-2-sulfonamide;
N-(6-fluoroquinolin-8-yl)pyridine-3-sulfonamide;
N-(6-(trifluoromethoxy)quinolin-8-yl)pyridine-3-sulfonamide;
6-cyano-N-(6-(trifluoromethoxy)quinolin-8-yl)pyridine-3-sulfonamide;
6-cyano-N-(6-fluoroquinolin-8-yl)pyridine-3-sulfonamide;
N-(6-bromoquinolin-8-yl)benzenesulfonamide;
N-(5-chloroquinolin-8-yl)benzenesulfonamide;
N-(5-bromoquinolin-8-yl)benzenesulfonamide;
N-(5,7-dichloroquinolin-8-yl)-4-methylbenzenesulfonamide;
N-(5,7-dichloroquinolin-8-yl)-2,4,6-trimethylbenzenesulfonamide;
2,4-dichloro-N-(5-chloroquinolin-8-yl)benzenesulfonamide;
N-(5-chloroquinolin-8-yl)pyridine-3-sulfonamide;
2-amino-N-(5-chloroquinolin-8-yl)-4-methylbenzenesulfonamide;
N-(5-chloro-6-fluoroquinolin-8-yl)benzenesulfonamide;
N-(5,6-difluoroquinolin-8-yl)benzenesulfonamide;
N-(5-fluoroquinolin-8-yl)benzenesulfonamide;
N-(5-morpholinoquinolin-8-yl)benzenesulfonamide;
N-(5-bromoquinolin-8-yl)-5-(2-(methylthio)pyrimidin-4-yl)thiophene-2-sulfonamide;
N-(5-bromoquinolin-8-yl)-5-(oxazol-5-yl)thiophene-2-sulfonamide; or
N-(5-bromoquinolin-8-yl)-4-(2-methylpyrimidin-4-yl)benzenesulfonamide.

In embodiment $I_3$, the compounds are of embodiment $I_1$ or $I_2$, wherein
$R^1$ is —($C_1$-$C_6$ haloalkyl), —Y—($C_1$-$C_6$ haloalkyl), —Y—($C_0$-$C_6$ alkyl)-Ar, —Y—($C_0$-$C_6$ alkyl)-Het, —Y—($C_0$-$C_6$ alkyl)-Cak, —Y—($C_0$-$C_6$ alkyl)-Hca, -halogen, —$NO_2$ or —CN,
wherein Y is O, S, N($R^5$), and $R^5$ is -hydrogen or —($C_1$-$C_6$ alkyl),
provided that the compound is not:
N-(6-chloroquinolin-8-yl)benzenesulfonamide;
N-(5,7-dichloroquinolin-8-yl)-4-methylbenzenesulfonamide;
N-(5,7-dichloroquinolin-8-yl)-2,4,6-trimethylbenzenesulfonamide;
N-(6-fluoroquinolin-8-yl)benzenesulfonamide;
N-(5-chloro-6-fluoroquinolin-8-yl)benzenesulfonamide;
N-(6-(trifluoromethoxy)quinolin-8-yl)benzenesulfonamide;
2,6-difluoro-N-(6-fluoroquinolin-8-yl)benzenesulfonamide;
4-chloro-2-fluoro-N-(6-fluoroquinolin-8-yl)benzenesulfonamide;
N-(6-fluoroquinolin-8-yl)pyridine-3-sulfonamide;
N-(5,6-difluoroquinolin-8-yl)benzenesulfonamide;
N-(7-chloroquinolin-8-yl)benzenesulfonamide;
N-(6-(trifluoromethoxy)quinolin-8-yl)-6-(trifluoromethyl)pyridine-3-sulfonamide;
N-(6-(trifluoromethoxy)quinolin-8-yl)pyridine-2-sulfonamide;
N-(6-fluoroquinolin-8-yl)pyridine-3-sulfonamide;
N-(6-(trifluoromethoxy)quinolin-8-yl)pyridine-3-sulfonamide;
6-cyano-N-(6-(trifluoromethoxy)quinolin-8-yl)pyridine-3-sulfonamide;
6-cyano-N-(6-fluoroquinolin-8-yl)pyridine-3-sulfonamide; or
N-(6-bromoquinolin-8-yl)benzenesulfonamide.

In embodiment $I_4$, the compounds are of any embodiment $I_1$, $I_2$, or $I_3$, wherein
$R^3$ is —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, -halogen, —$NO_2$ or —CN,
provided that the compound is not:

N-(5-bromoquinolin-8-yl)-4-methylbenzenesulfonamide
N-(5-chloroquinolin-8-yl)benzenesulfonamide;
N-(5-bromoquinolin-8-yl)benzenesulfonamide;
N-(5,7-dichloroquinolin-8-yl)-4-methylbenzenesulfonamide;
N-(5,7-dichloroquinolin-8-yl)-2,4,6-trimethylbenzenesulfonamide;
2,4-dichloro-N-(5-chloroquinolin-8-yl)benzenesulfonamide;
N-(5-chloroquinolin-8-yl)pyridine-3-sulfonamide;
2-amino-N-(5-chloroquinolin-8-yl)-4-methylbenzenesulfonamide;
N-(5-chloro-6-fluoroquinolin-8-yl)benzenesulfonamide;
N-(5,6-difluoroquinolin-8-yl)benzenesulfonamide;
N-(5-fluoroquinolin-8-yl)benzenesulfonamide;
N-(5-morpholinoquinolin-8-yl)benzenesulfonamide;
N-(5-bromoquinolin-8-yl)-5-(2-(methylthio)pyrimidin-4-yl)thiophene-2-sulfonamide;
N-(5-bromoquinolin-8-yl)-5-(oxazol-5-yl)thiophene-2-sulfonamide; or
N-(5-bromoquinolin-8-yl)-4-(2-methylpyrimidin-4-yl)benzenesulfonamide.

In embodiment I$_5$, the compounds are of any embodiment I$_1$, I$_2$, I$_3$ or I$_4$ wherein
R$^1$ is —(C$_1$-C$_6$ haloalkyl), —Y—(C$_1$-C$_6$ haloalkyl), —Y—(C$_0$-C$_6$ alkyl)-Ar, —Y—(C$_0$-C$_6$ alkyl)-Het, —Y—(C$_0$-C$_6$ alkyl)-Cak, —Y—(C$_0$-C$_6$ alkyl)-Hca, —NO$_2$ or —CN,
wherein Y is O, S, N(R$^5$), and R$^5$ is -hydrogen or —(C$_1$-C$_6$ alkyl),
provided that the compound is not:
N-(6-(trifluoromethoxy)quinolin-8-yl)benzenesulfonamide;
N-(6-(trifluoromethoxy)quinolin-8-yl)-6-(trifluoromethyl)pyridine-3-sulfonamide;
N-(6-(trifluoromethoxy)quinolin-8-yl)pyridine-2-sulfonamide;
N-(6-(trifluoromethoxy)quinolin-8-yl)pyridine-3-sulfonamide; or
6-cyano-N-(6-(trifluoromethoxy)quinolin-8-yl)pyridine-3-sulfonamide.

In embodiment I$_6$, the compounds are of embodiment I$_1$, I$_2$, I$_3$, I$_4$ or I$_5$ wherein
R$^3$ is —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —NO$_2$ or —CN,
provided that the compound is not:
N-(5-morpholinoquinolin-8-yl)benzenesulfonamide.

The invention further comprises subgenera of formula (I) in which structural formula (I), R$^1$, R$^2$, R$^3$, and R$^4$ are any combination of groups as defined hereinbelow (e.g., structural formula (I) is formula (If), R$^1$ is group (1k), R$^2$ is group 2(b), R$^3$ is group (3dd) and R$^4$ is group (4q)):

Structural Formula (I) is One of Formulae (Ia)-(Ik):

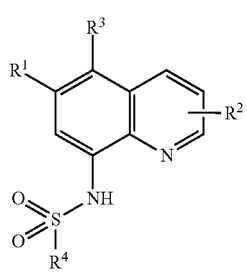
(Ia)

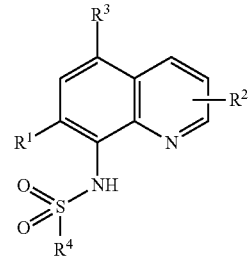
(Ib)

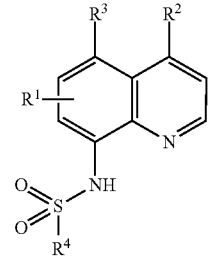
(Ic)

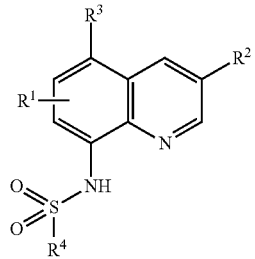
(Id)

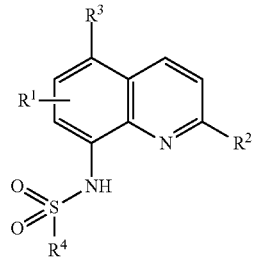
(Ie)

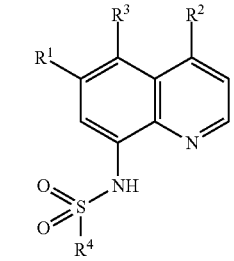
(If)

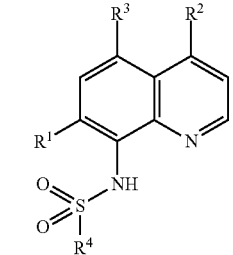
(Ig)

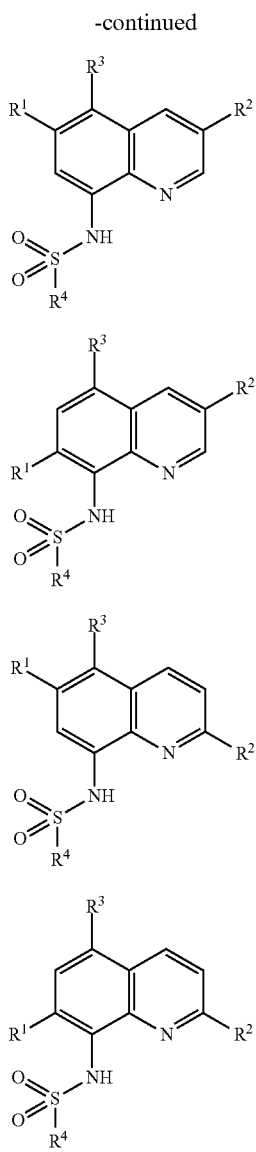

R¹ is selected from one of the following groups (1a)-(1bbb):

(1a) -hydrogen, —($C_1$-$C_6$ haloalkyl), —Y—($C_1$-$C_6$ haloalkyl), —Y—($C_0$-$C_6$ alkyl)-Ar, —Y—($C_0$-$C_6$ alkyl)-Het, —Y—($C_0$-$C_6$ alkyl)-Cak, —Y—($C_0$-$C_6$ alkyl)-Hca, -halogen, —$NO_2$ or —CN, wherein Y is O, S, N($R^5$), and $R^5$ is -hydrogen or —($C_1$-$C_6$ alkyl).
(1b) As in group (1a), wherein Y is O or N($R^5$).
(1c) As in group (1a), wherein Y is N($R^5$).
(1d) As in group (1a), wherein Y is S or N($R^5$).
(1e) As in any of groups (1a)-(1d), wherein $R^5$ is NH.
(1f) As in any of groups (1a)-(1d), wherein $R^5$ is NMe.
(1g) As in any of groups (1a)-(1d), wherein $R^5$ is NEt.
(1h) As in group (1a), wherein Y is O.
(1i) As in group (1a), wherein Y is S.
(1j) -hydrogen, —($C_1$-$C_6$ haloalkyl), —O—($C_1$-$C_6$ haloalkyl), —O—($C_0$-$C_6$ alkyl)-Ar, —O—($C_0$-$C_6$ alkyl)-Het, —O—($C_0$-$C_6$ alkyl)-Cak, —O—($C_0$-$C_6$ alkyl)-Hca, -halogen, —$NO_2$ or —CN.
(1k) -hydrogen, —($C_1$-$C_6$ haloalkyl), —O—($C_1$-$C_6$ haloalkyl), —O—($C_0$-$C_6$ alkyl)-Ar, —O—($C_0$-$C_6$ alkyl)-Het, —O—($C_0$-$C_6$ alkyl)-Cak, —O—($C_0$-$C_6$ alkyl)-Hca, -halogen, —$NO_2$ or —CN, wherein —($C_1$-$C_6$ haloalkyl), —O—($C_1$-$C_6$ haloalkyl), —O—($C_0$-$C_6$ alkyl)-Ar, —O—($C_0$-$C_6$ alkyl)-Het, —O—($C_0$-$C_6$ alkyl)-Cak and —O—($C_0$-$C_6$ alkyl)-Hca are each optionally substituted with one or more substituents selected from the group consisting of —($C_1$-$C_6$ alkyl), —O—($C_1$-$C_6$ alkyl), —($C_1$-$C_6$ haloalkyl), -halogen, —$NO_2$ and —CN.
(1l) -hydrogen, —($C_1$-$C_6$ haloalkyl), —O—($C_0$-$C_6$ alkyl)-Ar, —O—($C_0$-$C_6$ alkyl)-Het, —O—($C_0$-$C_6$ alkyl)-Cak, —O—($C_0$-$C_6$ alkyl)-Hca, —$NO_2$ or —CN.
(1m) —($C_1$-$C_6$ haloalkyl), —O—($C_0$-$C_6$ alkyl)-Ar, —O—($C_0$-$C_6$ alkyl)-Het, —O—($C_0$-$C_6$ alkyl)-Cak, —O—($C_0$-$C_6$ alkyl)-Hca, —$NO_2$ or —CN.
(1n) -hydrogen, —($C_1$-$C_6$ haloalkyl), —O—($C_0$-$C_6$ alkyl)-Ar, —O—($C_0$-$C_6$ alkyl)-Het, —O—($C_0$-$C_6$ alkyl)-Cak, —O—($C_0$-$C_6$ alkyl)-Hca, —$NO_2$ or —CN, wherein —($C_1$-$C_6$ haloalkyl), —O—($C_1$-$C_6$ haloalkyl), —O—($C_0$-$C_6$ alkyl)-Ar, —O—($C_0$-$C_6$ alkyl)-Het, —O—($C_0$-$C_6$ alkyl)-Cak and —O—($C_0$-$C_6$ alkyl)-Hca are each optionally substituted with one or more substituents selected from the group consisting of —($C_1$-$C_6$ alkyl), —O—($C_1$-$C_6$ alkyl), —($C_1$-$C_6$ haloalkyl), -halogen, —$NO_2$ and —CN.
(1o) —($C_1$-$C_6$ haloalkyl), —O—($C_0$-$C_6$ alkyl)-Ar, —O—($C_0$-$C_6$ alkyl)-Het, —O—($C_0$-$C_6$ alkyl)-Cak, —O—($C_0$-$C_6$ alkyl)-Hca, —$NO_2$ or —CN, wherein —($C_1$-$C_6$ haloalkyl), —O—($C_1$-$C_6$ haloalkyl), —O—($C_0$-$C_6$ alkyl)-Ar, —O—($C_0$-$C_6$ alkyl)-Het, —O—($C_0$-$C_6$ alkyl)-Cak and —O—($C_0$-$C_6$ alkyl)-Hca are each optionally substituted with one or more substituents selected from the group consisting of —($C_1$-$C_6$ alkyl), —O—($C_1$-$C_6$ alkyl), —($C_1$-$C_6$ haloalkyl), -halogen, —$NO_2$ and —CN.
(1p) -hydrogen, —($C_1$-$C_6$ haloalkyl), —O—($C_1$-$C_6$ haloalkyl), -halogen, —$NO_2$ or —CN.
(1q) —($C_1$-$C_6$ haloalkyl), —O—($C_1$-$C_6$ haloalkyl), -halogen, —$NO_2$ or —CN.
(1r) -hydrogen, —O—($C_0$-$C_6$ alkyl)-Ar, —O—($C_0$-$C_6$ alkyl)-Het, —O—($C_0$-$C_6$ alkyl)-Cak, —O—($C_0$-$C_6$ alkyl)-Hca, -halogen, —$NO_2$ or —CN.
(1s) —O—($C_0$-$C_6$ alkyl)-Ar, —O—($C_0$-$C_6$ alkyl)-Het, —O—($C_0$-$C_6$ alkyl)-Cak, —O—($C_0$-$C_6$ alkyl)-Hca, -halogen, —$NO_2$ or —CN.
(1t) —O—($C_0$-$C_6$ alkyl)-Ar, —O—($C_0$-$C_6$ alkyl)-Het, —O—($C_0$-$C_6$ alkyl)-Cak, or —O—($C_0$-$C_6$ alkyl)-Hca.
(1u) -hydrogen, —O—($C_1$-$C_6$ haloalkyl), —O—($C_0$-$C_6$ alkyl)-Ar, —O—($C_0$-$C_6$ alkyl)-Het, —O—($C_0$-$C_6$ alkyl)-Cak or —O—($C_0$-$C_6$ alkyl)-Hca.
(1v) —O—($C_1$-$C_6$ haloalkyl), —O—($C_0$-$C_6$ alkyl)-Ar, —O—($C_0$-$C_6$ alkyl)-Het, —O—($C_0$-$C_6$ alkyl)-Cak or —O—($C_0$-$C_6$ alkyl)-Hca.
(1w) —O—($C_1$-$C_6$ haloalkyl).
(1x) -hydrogen.
(1y) —O—($C_1$-$C_6$ haloalkyl).
(1z) —$OCF_3$.
(1aa) —O—($C_0$-$C_6$ alkyl)-Ar or —O—($C_0$-$C_6$ alkyl)-Het.
(1bb) —O—($C_0$-$C_6$ alkyl)-Ar.
(1cc) —O—($C_0$-$C_6$ alkyl)-Het.
(1dd) —O—($C_0$-$C_6$ alkyl)-Cak or —O—($C_0$-$C_6$ alkyl)-Hca.
(1ee) —O—($C_0$-$C_6$ alkyl)-Cak.
(1ff) —O—($C_0$-$C_6$ alkyl)-Hca.
(1gg) -hydrogen, —($C_1$-$C_6$ haloalkyl), —O—($C_1$-$C_6$ haloalkyl), -halogen, —$NO_2$ or —CN, wherein —($C_1$-$C_6$ haloalkyl) and —O—($C_1$-$C_6$ haloalkyl) are each optionally substituted with one or more —($C_1$-$C_6$ alkyl), —O—($C_1$-$C_6$ alkyl), —($C_1$-$C_6$ haloalkyl), -halogen, —$NO_2$ or —CN.

(1hh) —($C_1$-$C_6$ haloalkyl), —O—($C_1$-$C_6$ haloalkyl), -halogen, —$NO_2$ or —CN, wherein —($C_1$-$C_6$ haloalkyl) and —O—($C_1$-$C_6$ haloalkyl) are each optionally substituted with one or more —($C_1$-$C_6$ alkyl), —O—($C_1$-$C_6$ alkyl), —($C_1$-$C_6$ haloalkyl), -halogen, —$NO_2$ or —CN.

(1ii) -hydrogen, —O—($C_0$-$C_6$ alkyl)-Ar, —O—($C_0$-$C_6$ alkyl)-Het, —O—($C_0$-$C_6$ alkyl)-Cak, —O—($C_0$-$C_6$ alkyl)-Hca, -halogen, —$NO_2$ or —CN, wherein —O—($C_0$-$C_6$ alkyl)-Ar, —O—($C_0$-$C_6$ alkyl)-Het, —O—($C_0$-$C_6$ alkyl)-Cak and —O—($C_0$-$C_6$ alkyl)-Hca are each optionally substituted with one or more —($C_1$-$C_6$ alkyl), —O—($C_1$-$C_6$ alkyl), —($C_1$-$C_6$ haloalkyl), -halogen, —$NO_2$ or —CN.

(1jj) —O—($C_0$-$C_6$ alkyl)-Ar, —O—($C_0$-$C_6$ alkyl)-Het, —O—($C_0$-$C_6$ alkyl)-Cak, —O—($C_0$-$C_6$ alkyl)-Hca, -halogen, —$NO_2$ or —CN, wherein —O—($C_0$-$C_6$ alkyl)-Ar, —O—($C_0$-$C_6$ alkyl)-Het, —O—($C_0$-$C_6$ alkyl)-Cak and —O—($C_0$-$C_6$ alkyl)-Hca are each optionally substituted with one or more —($C_1$-$C_6$ alkyl), —O—($C_1$-$C_6$ alkyl), —($C_1$-$C_6$ haloalkyl), -halogen, —$NO_2$ or —CN.

(1kk) -hydrogen, —O—($C_0$-$C_6$ alkyl)-Ar, —O—($C_0$-$C_6$ alkyl)-Het, —O—($C_0$-$C_6$ alkyl)-Cak or —O—($C_0$-$C_6$ alkyl)-Hca, wherein —O—($C_0$-$C_6$ alkyl)-Ar, —O—($C_0$-$C_6$ alkyl)-Het, —O—($C_0$-$C_6$ alkyl)-Cak and —O—($C_0$-$C_6$ alkyl)-Hca are each optionally substituted with one or more —($C_1$-$C_6$ alkyl), —O—($C_1$-$C_6$ alkyl), —($C_1$-$C_6$ haloalkyl), -halogen, —$NO_2$ or —CN.

(1ll) —O—($C_0$-$C_6$ alkyl)-Ar, —O—($C_0$-$C_6$ alkyl)-Het, —O—($C_0$-$C_6$ alkyl)-Cak or —O—($C_0$-$C_6$ alkyl)-Hca, wherein —O—($C_0$-$C_6$ alkyl)-Ar, —O—($C_0$-$C_6$ alkyl)-Het, —O—($C_0$-$C_6$ alkyl)-Cak and —O—($C_0$-$C_6$ alkyl)-Hca are each optionally substituted with one or more —($C_1$-$C_6$ alkyl), —O—($C_1$-$C_6$ alkyl), —($C_1$-$C_6$ haloalkyl), -halogen, —$NO_2$ or —CN.

(1mm) —O—($C_0$-$C_6$ alkyl)-Ar or —O—($C_0$-$C_6$ alkyl)-Het, wherein —O—($C_0$-$C_6$ alkyl)-Ar or —O—($C_0$-$C_6$ alkyl)-Het are each optionally substituted with one or more —($C_1$-$C_6$ alkyl), —O—($C_1$-$C_6$ alkyl), —($C_1$-$C_6$ haloalkyl), -halogen, —$NO_2$ or —CN.

(1nn) —O—($C_0$-$C_6$ alkyl)-Ar, optionally substituted with one or more —($C_1$-$C_6$ alkyl), —O—($C_1$-$C_6$ alkyl), —($C_1$-$C_6$ haloalkyl), -halogen, —$NO_2$ or —CN.

(1oo) —O—($C_0$-$C_6$ alkyl)-Ar, optionally substituted with one or more —O—($C_1$-$C_6$ alkyl), -halogen or —CN.

(1pp) —O—($C_0$-$C_6$ alkyl)-phenyl, optionally substituted with one or more —O—($C_1$-$C_6$ alkyl), -halogen or —CN.

(1qq)

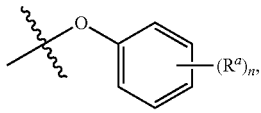

wherein $R^a$ is independently -hydrogen, —($C_1$-$C_6$ alkyl), —O—($C_1$-$C_6$ alkyl), —($C_1$-$C_6$ haloalkyl), -halogen, —$NO_2$ or —CN, and n is 1, 2, 3, 4 or 5.

(1rr) As group (1qq), wherein, $R^a$ is independently —O—($C_1$-$C_6$ alkyl), —($C_1$-$C_6$ haloalkyl), -halogen or —CN, and n is 1, 2, 3 or 4.

(1ss) As group (1qq), wherein $R^a$ is independently —O—($C_1$-$C_6$ alkyl), -halogen or —CN, and n is 1 or 2.

(1tt) As group (1qq), wherein $R^a$ is independently —OMe, fluoro, chloro, bromo, iodo or —CN, and n is 1 or 2.

(1uu) As group (1qq), wherein $R^a$ is independently —OMe, fluoro, chloro, bromo or —CN, and n is 1 or 2.

(1vv)

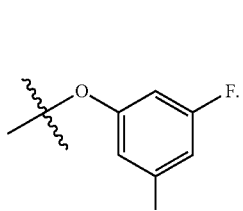

(1ww)

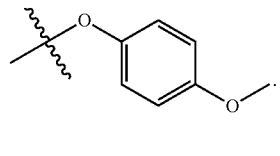

(1xx)

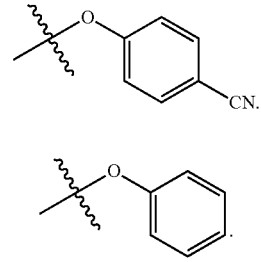

(1yy)

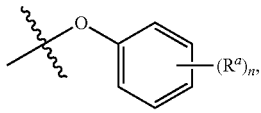

(1zz) —O—($C_0$-$C_6$ alkyl)-Het, optionally substituted with one or more —($C_1$-$C_6$ alkyl), —O—($C_1$-$C_6$ alkyl), —($C_1$-$C_6$ haloalkyl), -halogen, —$NO_2$ or —CN.

(1aaa) —O—($C_0$-$C_6$ alkyl)-pyridyl, optionally substituted with one or more —($C_1$-$C_6$ alkyl), —O—($C_1$-$C_6$ alkyl), —($C_1$-$C_6$ haloalkyl), -halogen, —$NO_2$ or —CN.

(1bbb) —O—($C_0$-$C_6$ alkyl)-Ar or —O—($C_0$-$C_6$ alkyl)-Het, wherein —O—($C_0$-$C_6$ alkyl)-Ar or —O—($C_0$-$C_6$ alkyl)-Het are each optionally substituted with one or more —($C_1$-$C_6$ alkyl), —O—($C_1$-$C_6$ alkyl), —($C_1$-$C_6$ haloalkyl), -halogen, —$NO_2$ or —CN.

$R^2$ is selected from one of the following groups (2a)-(2xx):

(2a) -hydrogen, —($C_1$-$C_6$ alkyl), —($C_1$-$C_6$ haloalkyl), —Y—($C_1$-$C_6$ alkyl), —Y—($C_1$-$C_6$ haloalkyl), -halogen, —$NO_2$ or —CN, wherein Y is O, S, N($R^5$), and $R^5$ is -hydrogen or —($C_1$-$C_6$ alkyl).

(2b) As in group (2a), wherein Y is O or N($R^5$).

(2c) As in group (2a), wherein Y is N($R^5$).

(2d) As in group (2a), wherein Y is S or N($R^5$).

(2e) As in any of groups (2a)-(2d), wherein $R^5$ is NH.

(2f) As in any of groups (2a)-(2d), wherein $R^5$ is NMe.

(2g) As in any of groups (2a)-(2d), wherein $R^5$ is NEt.

(2h) As in group (2a), wherein Y is O.

(2i) As in group (2a), wherein Y is S.

(2j) -hydrogen, —($C_1$-$C_6$ alkyl), —($C_1$-$C_6$ haloalkyl), —O—($C_1$-$C_6$ alkyl), —O—($C_1$-$C_6$ haloalkyl), -halogen, —$NO_2$ or —CN.

(2k) -hydrogen, —($C_1$-$C_6$ alkyl), —($C_1$-$C_6$ haloalkyl), —O—($C_1$-$C_6$ alkyl), —O—($C_1$-$C_6$ haloalkyl), -halogen, —$NO_2$ or —CN, wherein —($C_1$-$C_6$ alkyl), —($C_1$-$C_6$ haloalkyl), —O—($C_1$-$C_6$ alkyl) and —O—($C_1$-$C_6$ haloalkyl) are each optionally substituted with one or more —($C_1$-$C_6$ alkyl), —($C_1$-$C_6$ haloalkyl), -halogen, —$NO_2$ or —CN.

(2l) —($C_1$-$C_6$ alkyl), —($C_1$-$C_6$ haloalkyl), —O—($C_1$-$C_6$ alkyl), —O—($C_1$-$C_6$ haloalkyl), -halogen, —$NO_2$ or —CN.

(2m) -hydrogen, —($C_1$-$C_6$ alkyl), —($C_1$-$C_6$ haloalkyl), —O—($C_1$-$C_6$ alkyl) or —O—($C_1$-$C_6$ haloalkyl).

(2n) -hydrogen, —($C_1$-$C_6$ haloalkyl), —O—($C_1$-$C_6$ haloalkyl), -halogen, —$NO_2$ or —CN.
(2o) —($C_1$-$C_6$ haloalkyl), —O—($C_1$-$C_6$ haloalkyl), -halogen, —$NO_2$ or —CN.
(2p) -hydrogen, -halogen, —$NO_2$ or —CN.
(2q) -hydrogen, —$NO_2$ or —CN.
(2r) -hydrogen, -halogen or —CN.
(2s) -hydrogen or -halogen.
(2t) -hydrogen or —CN.
(2u) -hydrogen.
(2v) -halogen.
(2w) -fluoro, -chloro, -bromo or -iodo.
(2x) -fluoro, -chloro or -bromo.
(2y) -chloro or -bromo.
(2z) -fluoro or -bromo.
(2aa) -fluoro or -chloro.
(2bb) -fluoro.
(2cc) -chloro.
(2dd) -bromo.
(2ee) -hydrogen, —($C_1$-$C_6$ alkyl) or —($C_1$-$C_6$ haloalkyl).
(2ff) -hydrogen, —O—($C_1$-$C_6$ alkyl) or —O—($C_1$-$C_6$ haloalkyl).
(2gg) -hydrogen, —($C_1$-$C_6$ alkyl) or —O—($C_1$-$C_6$ alkyl).
(2hh) -hydrogen or —($C_1$-$C_6$ alkyl).
(2ii) -hydrogen or —O—($C_1$-$C_6$ alkyl).
(2jj) —($C_1$-$C_6$ alkyl).
(2kk) -methyl.
(2ll) -ethyl.
(2mm) -n-propyl.
(2nn) -i-propyl.
(2oo) —O—($C_1$-$C_6$ alkyl).
(2pp) —OMe.
(2qq) —OEt.
(2rr) —O-n-Pr.
(2ss) —O-i-Pr.
(2tt) —O—($C_1$-$C_6$ haloalkyl).
(2uu) —$OCF_3$.
(2vv) —($C_1$-$C_6$ alkyl) or —($C_1$-$C_6$ haloalkyl).
(2ww) —O—($C_1$-$C_6$ alkyl) or —O—($C_1$-$C_6$ haloalkyl).
(2xx) —($C_1$-$C_6$ alkyl) or —O—($C_1$-$C_6$ alkyl).

$R^3$ is selected from one of the following groups (3a)-(3ssss):

(3a) -hydrogen, —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, -halogen, —$NO_2$ or —CN.
(3b) -hydrogen, —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, -halogen, —$NO_2$ or —CN, wherein —($C_0$-$C_6$ alkyl)-Ar, —($C_0$-$C_6$ alkyl)-Het, —($C_0$-$C_6$ alkyl)-Cak and —($C_0$-$C_6$ alkyl)-Hca are each optionally substituted with one or more —($C_1$-$C_6$ alkyl), —($C_1$-$C_6$ haloalkyl), —($C_1$-$C_6$ alkyl)-Ar, -halogen, —$NO_2$ or —CN.
(3c) -hydrogen, —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, -halogen, —$NO_2$ or —CN.
(3d) -hydrogen, —($C_0$-$C_6$ alkyl)-Ar, —($C_0$-$C_6$ alkyl)-Het, —($C_0$-$C_6$ alkyl)-Cak, —$NO_2$ or CN.
(3e) —($C_0$-$C_6$ alkyl)-Ar, —($C_0$-$C_6$ alkyl)-Het, —($C_0$-$C_6$ alkyl)-Cak, —$NO_2$ or CN.
(3f) -hydrogen, —($C_0$-$C_6$ alkyl)-Ar, —($C_0$-$C_6$ alkyl)-Het, —($C_0$-$C_6$ alkyl)-Cak, —$NO_2$ or CN, wherein —($C_0$-$C_6$ alkyl)-Ar, —($C_0$-$C_6$ alkyl)-Het, —($C_0$-$C_6$ alkyl)-Cak and —($C_0$-$C_6$ alkyl)-Hca are each optionally substituted with one or more —($C_1$-$C_6$ alkyl), —($C_1$-$C_6$ haloalkyl), —($C_1$-$C_6$ alkyl)-Ar, -halogen, —$NO_2$ or —CN.
(3g) —($C_0$-$C_6$ alkyl)-Ar, —($C_0$-$C_6$ alkyl)-Het, —($C_0$-$C_6$ alkyl)-Cak, —$NO_2$ or CN, wherein —($C_0$-$C_6$ alkyl)-Ar, —($C_0$-$C_6$ alkyl)-Het, —($C_0$-$C_6$ alkyl)-Cak and —($C_0$-$C_6$ alkyl)-Hca are each optionally substituted with one or more —($C_1$-$C_6$ alkyl), —($C_1$-$C_6$ haloalkyl), —($C_1$-$C_6$ alkyl)-Ar, -halogen, —$NO_2$ or —CN.
(3h) -hydrogen, —($C_0$-$C_6$ alkyl)-Ar, —($C_0$-$C_6$ alkyl)-Het, —($C_0$-$C_6$ alkyl)-Cak or —($C_0$-$C_6$ alkyl)-Hca.
(3i) -hydrogen, -halogen, —$NO_2$ or —CN.
(3j) —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, -halogen, —$NO_2$ or —CN.
(3k) -halogen, —$NO_2$ or —CN.
(3l) -hydrogen or -halogen.
(3m) -hydrogen.
(3n) -halogen.
(3o) -fluoro, -chloro, -bromo or -iodo.
(3p) -fluoro, -chloro or -bromo.
(3q) -chloro or -bromo.
(3r) -fluoro or -bromo.
(3s) -fluoro or -chloro.
(3t) -fluoro.
(3u) -chloro.
(3v) -bromo.
(3w) —($C_0$-$C_6$ alkyl)-Ar, —($C_0$-$C_6$ alkyl)-Het, —($C_0$-$C_6$ alkyl)-Cak or —($C_0$-$C_6$ alkyl)-Hca.
(3x) —($C_0$-$C_6$ alkyl)-Ar or —($C_0$-$C_6$ alkyl)-Het.
(3y) —($C_0$-$C_6$ alkyl)-Cak or —($C_0$-$C_6$ alkyl)-Hca.
(3z) —($C_0$-$C_6$ alkyl)-Ar.
(3aa) —($C_0$-$C_6$ alkyl)-phenyl optionally substituted with one or more —($C_1$-$C_6$ alkyl), —($C_1$-$C_6$ haloalkyl), —($C_1$-$C_6$ alkyl)-Ar, -halogen, —$NO_2$ or —CN.
(3bb) —Ar.
(3cc) -phenyl optionally substituted with one or more —($C_1$-$C_6$ alkyl), —($C_1$-$C_6$ haloalkyl), —($C_1$-$C_6$ alkyl)-Ar, -halogen, —$NO_2$ or —CN.
(3dd) -phenyl optionally substituted with one or more —($C_1$-$C_6$ alkyl), —($C_1$-$C_6$ haloalkyl), -halogen, —$NO_2$ or —CN.
(3ee) -phenyl optionally substituted with one or more —($C_1$-$C_6$ alkyl), -halogen, —$NO_2$ or —CN.
(3ff) -phenyl optionally substituted with one or more —($C_1$-$C_6$ alkyl), -halogen, or —CN.
(3gg) -phenyl optionally substituted with one or more —($C_1$-$C_6$ alkyl) or -halogen.
(3hh) -phenyl optionally substituted with one or more —($C_1$-$C_6$ alkyl).
(3ii) -phenyl optionally substituted with one or more -halogen.

(3jj)

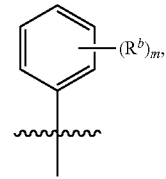

wherein $R^b$ is independently hydrogen, —($C_1$-$C_6$ alkyl), —O—($C_1$-$C_6$ alkyl), —($C_1$-$C_6$ haloalkyl), -halogen, —$NO_2$ or —CN, and m is 1, 2, 3, 4 or 5.

(3kk) As group (3jj), wherein, $R^b$ is independently —O—($C_1$-$C_6$ alkyl), —($C_1$-$C_6$ haloalkyl), -halogen or —CN, and m is 1, 2, 3 or 4.

(3ll) As group (3jj), wherein, $R^b$ is independently —O—($C_1$-$C_6$ alkyl), -halogen or —CN, and m is 1 or 2.

(3mm) As group (3jj), wherein, $R^b$ is independently —OMe, fluoro, chloro, bromo, iodo or —CN, and m is 1 or 2.

(3nn) As group (3jj), wherein, $R^b$ is independently —OMe, fluoro, chloro, bromo or —CN, and m is 1 or 2.

(3oo)

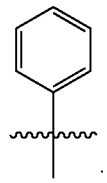

(3pp) —($C_0$-$C_6$ alkyl)-Het.

(3qq) —($C_0$-$C_6$ alkyl)-pyridyl optionally substituted with one or more —($C_1$-$C_6$ alkyl), —($C_1$-$C_6$ haloalkyl), —($C_1$-$C_6$ alkyl)-Ar, -halogen, —$NO_2$ or —CN.

(3rr) —($C_0$-$C_6$ alkyl)-furanyl optionally substituted with one or more —($C_1$-$C_6$ alkyl), —($C_1$-$C_6$ haloalkyl), —($C_1$-$C_6$ alkyl)-Ar, -halogen, —$NO_2$ or —CN.

(3ss) —($C_0$-$C_6$ alkyl)-thiophenyl optionally substituted with one or more —($C_1$-$C_6$ alkyl), —($C_1$-$C_6$ haloalkyl), —($C_1$-$C_6$ alkyl)-Ar, -halogen, —$NO_2$ or —CN.

(3tt) —($C_0$-$C_6$ alkyl)-benzofuranyl optionally substituted with one or more —($C_1$-$C_6$ alkyl), —($C_1$-$C_6$ haloalkyl), —($C_1$-$C_6$ alkyl)-Ar, -halogen, —$NO_2$ or —CN.

(3uu) —($C_0$-$C_6$ alkyl)-benzothiaphenyl optionally substituted with one or more —($C_1$-$C_6$ alkyl), —($C_1$-$C_6$ haloalkyl), —($C_1$-$C_6$ alkyl)-Ar, -halogen, —$NO_2$ or —CN.

(3vv) -Het.

(3ww) -pyridyl optionally substituted with one or more —($C_1$-$C_6$ alkyl), —($C_1$-$C_6$ haloalkyl), —($C_1$-$C_6$ alkyl)-Ar, -halogen, —$NO_2$ or —CN.

(3xx) -pyridyl optionally substituted with one or more —($C_1$-$C_6$ alkyl), —($C_1$-$C_6$ haloalkyl), -halogen, —$NO_2$ or —CN.

(3yy) -pyridyl optionally substituted with one or more —($C_1$-$C_6$ alkyl), -halogen, —$NO_2$ or —CN.

(3zz) -pyridyl optionally substituted with one or more —($C_1$-$C_6$ alkyl), -halogen, or —CN.

(3aaa) -pyridyl optionally substituted with one or more —($C_1$-$C_6$ alkyl) or -halogen.

(3bbb) -pyridyl optionally substituted with one or more —($C_1$-$C_6$ alkyl).

(3ccc) -pyridyl optionally substituted with one or more -halogen.

(3ddd)

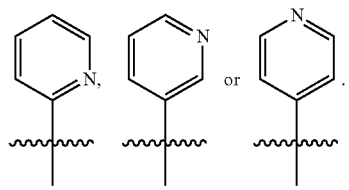

wherein $R^d$ is independently —($C_1$-$C_6$ alkyl), —O—($C_1$-$C_6$ alkyl), —($C_1$-$C_6$ haloalkyl), -halogen, —$NO_2$ or —CN, x is 1, 2, 3, 4 or 5, and one of $X^1$, $X^2$ and $X^3$ is N.

(3eee) As group (3ddd), wherein $R^d$ is independently —O—($C_1$-$C_6$ alkyl), —($C_1$-$C_6$ haloalkyl), -halogen or —CN, x is 1, 2, 3 or 4, and one of $X^1$, $X^2$ and $X^3$ is N.

(3fff) As group (3ddd), wherein $R^d$ is independently —O—($C_1$-$C_6$ alkyl), -halogen or —CN, x is 1 or 2, and one of $X^1$, $X^2$ and $X^3$ is N.

(3ggg) As group (3ddd), wherein $R^d$ is independently —OMe, fluoro, chloro, bromo, iodo or —CN, x is 1 or 2, and $X^2$ or $X^3$ is N.

(3hhh) As group (3ddd), wherein $R^d$ is independently —OMe, fluoro, chloro, bromo or —CN, x is 1 or 2, and one of $X^2$ is N.

(3iii) As group (3ddd), wherein $R^d$ is independently —OMe, fluoro, chloro, bromo or —CN, x is 1 or 2, and one of $X^3$ is N.

(3jjj)

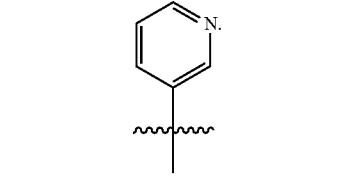

(3kkk)

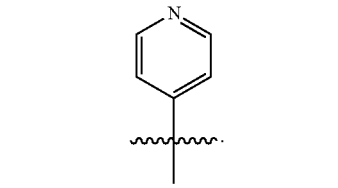

(3lll)

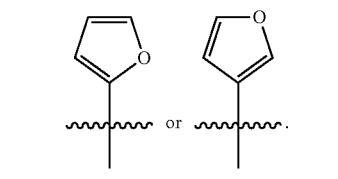

(3mmm)

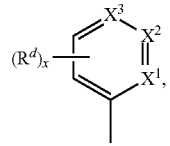

(3nnn)

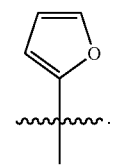

(3ooo) 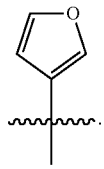

(3ppp) 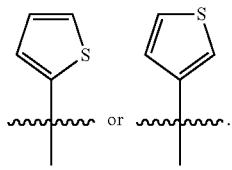 or (3qqq) 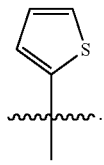

(3rrr) 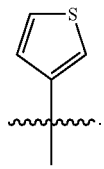

(3sss) 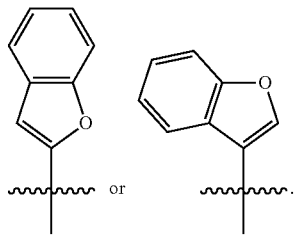 or (3ttt) 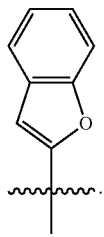

(3uuu) 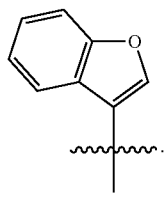

(3vvv) 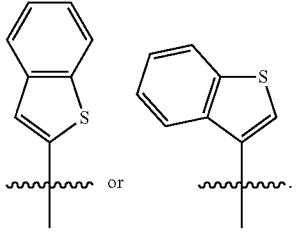 or (3www) 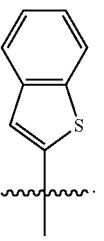

(3xxx) 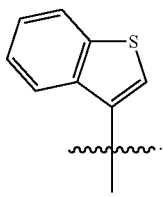

(3yyy) —($C_0$-$C_6$ alkyl)-Cak.

(3zzz) -Cak.

(3aaaa) -cyclopropyl, -cyclobutyl, -cyclopentyl or -cyclohexyl.

(3bbbb) -cyclopropyl, -cyclopentyl or -cyclohexyl.

(3cccc) -cyclopentyl or -cyclohexyl.

(3dddd) -cyclopentyl.

(3eeee) -cyclohexyl.

(3ffff) —($C_0$-$C_6$ alkyl)-Hca.

(3gggg) -Hca.

(3hhhh)

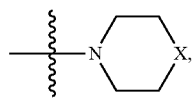

wherein X is —O—, —S—, N($R^5$) or —C(H)—$CH_2$—Ar; and the

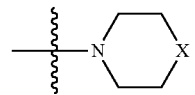

group is optionally substituted with one or more —($C_1$-$C_6$ alkyl), —($C_1$-$C_6$ haloalkyl), —($C_1$-$C_6$ alkyl)-Ar, -halogen, —$NO_2$ or —CN.

(3iiii) As group (3hhhh), wherein X is —O—, N(R$^5$) or —C(H)—CH$_2$—Ar.
(3jjjj) As group (3hhhh), wherein X is —O— or —C(H)—CH$_2$—Ar.
(3kkkk) As group (3hhhh), wherein X is —O— or N(R$^5$).
(3llll) As group (3hhhh), wherein X is N(R$^5$) or —C(H)—CH$_2$—Ar.
(3mmmm) As group (3hhhh), wherein X is —O—.
(3nnnn) As group (3hhhh), wherein X is N(R$^5$).
(3oooo) As group (3hhhh), wherein X is —C(H)—CH$_2$—Ar.

(3pppp) 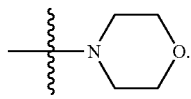

(3qqqq) 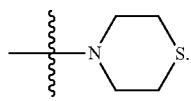

(3rrrr) 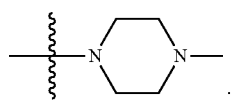

(3ssss) 

R$^4$ is selected from one of the following groups (4a)-(4yyy):
(4a) —(C$_1$-C$_6$ alkyl), —(C$_1$-C$_6$ haloalkyl), —(C$_0$-C$_6$ alkyl)-Ar, —(C$_0$-C$_6$ alkyl)-Het or —(C$_0$-C$_6$ alkyl)-Cak.
(4b) —(C$_1$-C$_6$ alkyl), —(C$_1$-C$_6$ haloalkyl), —(C$_0$-C$_6$ alkyl)-Ar, —(C$_0$-C$_6$ alkyl)-Het or —(C$_0$-C$_6$ alkyl)-Cak, wherein —(C$_1$-C$_6$ haloalkyl), —(C$_0$-C$_6$ alkyl)-Ar, —(C$_0$-C$_6$ alkyl)-Het and —(C$_0$-C$_6$ alkyl)-Cak are each optionally substituted with one or more —(C$_1$-C$_6$ alkyl), —(C$_1$-C$_6$ haloalkyl), —O—(C$_1$-C$_6$ alkyl), N(R$^5$)(R$^6$), -halogen, —NO$_2$ or —CN, wherein R$^5$ and R$^6$ are independently -hydrogen, —(C$_1$-C$_6$ alkyl) or —C(O)—(C$_1$-C$_6$ alkyl).
(4c) —(C$_1$-C$_6$ alkyl) or —(C$_1$-C$_6$ haloalkyl).
(4d) —(C$_1$-C$_6$ alkyl).
(4e) -methyl.
(4f) -ethyl.
(4g) -n-propyl.
(4h) -i-propyl.
(4i) —(C$_1$-C$_6$ haloalkyl).
(4j) —CF$_3$.
(4k) —(C$_0$-C$_6$ alkyl)-Ar, —(C$_0$-C$_6$ alkyl)-Het or —(C$_0$-C$_6$ alkyl)-Cak.
(4l) —(C$_0$-C$_6$ alkyl)-Ar or —(C$_0$-C$_6$ alkyl)-Het.
(4m) —(C$_0$-C$_6$ alkyl)-Cak or —(C$_0$-C$_6$ alkyl)-Het.
(4n) —(C$_0$-C$_6$ alkyl)-Ar, or —(C$_0$-C$_6$ alkyl)-Cak.
(4o) —(C$_0$-C$_6$ alkyl)-Ar.
(4p) —Ar.
(4q) -phenyl.

(4r) 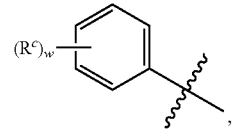

wherein R$^c$ is independently —(C$_1$-C$_6$ alkyl), —O—(C$_1$-C$_6$ alkyl), —(C$_1$-C$_6$ haloalkyl), -halogen, —NO$_2$ or —CN, and w is 1, 2, 3, 4 or 5.
(4s) As group (4r), wherein, R$^c$ is independently —O—(C$_1$-C$_6$ alkyl), —(C$_1$-C$_6$ haloalkyl), -halogen or —CN, and w is 1, 2, 3 or 4.
(4t) As group (4r), wherein, R$^c$ is independently —O—(C$_1$-C$_6$ alkyl), -halogen or —CN, and w is 1 or 2.
(4u) As group (4r), wherein, R$^c$ is independently —OMe, fluoro, chloro, bromo, iodo or —CN, and w is 1 or 2.
(4v) As group (4r), wherein, R$^c$ is independently —OMe, fluoro, chloro, bromo or —CN, and w is 1 or 2.
(4w) As group (4r), wherein, R$^c$ is -Me, and w is 1, 2 or 3.
(4x) —Ar, substituted with one or more of —(C$_1$-C$_6$ alkyl), —(C$_1$-C$_6$ haloalkyl), —O—(C$_1$-C$_6$ alkyl), N(R$^5$)(R$^6$), -halogen, —NO$_2$ or —CN, wherein R$^5$ and R$^6$ are independently -hydrogen, —(C$_1$-C$_6$ alkyl) or —C(O)—(C$_1$-C$_6$ alkyl).
(4y) -phenyl, substituted with one or more of —(C$_1$-C$_6$ alkyl), —(C$_1$-C$_6$ haloalkyl), —O—(C$_1$-C$_6$ alkyl), N(R$^5$)(R$^6$), -halogen, —NO$_2$ or —CN, wherein R$^5$ and R$^6$ are independently -hydrogen, —(C$_1$-C$_6$ alkyl) or —C(O)—(C$_1$-C$_6$ alkyl).
(4z) -phenyl, substituted with one or more of —(C$_1$-C$_6$ alkyl), —(C$_1$-C$_6$ haloalkyl), —O—(C$_1$-C$_6$ alkyl) or N(R$^5$)(R$^6$), wherein R$^5$ and R$^6$ are independently -hydrogen, —(C$_1$-C$_6$ alkyl) or —C(O)—(C$_1$-C$_6$ alkyl).
(4aa) -phenyl, substituted with one or more of —(C$_1$-C$_6$ alkyl), —(C$_1$-C$_6$ haloalkyl) or —O—(C$_1$-C$_6$ alkyl).
(4bb) -phenyl, substituted with one or more —(C$_1$-C$_6$ alkyl).

(4cc) 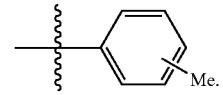

(4dd) 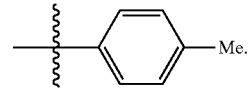

(4ee) -phenyl, substituted with one or more —(C$_1$-C$_6$ haloalkyl.

(4ff) 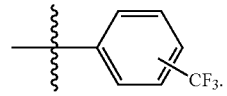

(4gg) 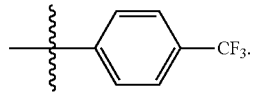

(4hh) 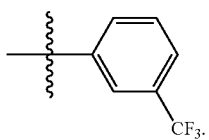

(4ii) -phenyl, substituted with one or more —O—(C$_1$-C$_6$ alkyl).

(4jj) 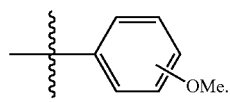

(4kk) 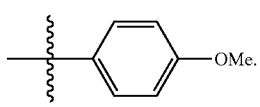

(4ll) -phenyl, substituted with one or more N(R$^5$)(R$^6$), wherein R$^5$ and R$^6$ are independently -hydrogen, —(C$_1$-C$_6$ alkyl) or —C(O)—(C$_1$-C$_6$ alkyl).

(4mm) -phenyl, substituted with one or more N(R$^5$)(R$^6$), wherein R$^5$ and R$^6$ are independently -hydrogen or —(C$_1$-C$_6$ alkyl).

(4nn) -phenyl, substituted with one or more N(R$^5$)(R$^6$), wherein R$^5$ and R$^6$ are independently -hydrogen or —C(O)—(C$_1$-C$_6$ alkyl).

(4oo) -phenyl, substituted with one N(R$^5$)(R$^6$), wherein R$^5$ is -hydrogen and R$^6$ is —C(O)—(C$_1$-C$_6$ alkyl).

(4pp) -phenyl, substituted with one N(R$^5$)(R$^6$), wherein R$^5$ is -hydrogen and R$^6$ is —C(O)-methyl.

(4qq) 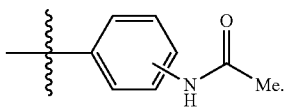

(4rr) 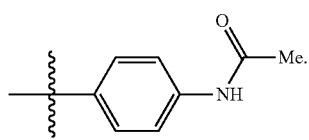

(4ss) —(C$_0$-C$_6$ alkyl)-Het.

(4tt) —(C$_0$-C$_6$ alkyl)-pyridyl optionally substituted with one or more —(C$_1$-C$_6$ alkyl), —(C$_1$-C$_6$ haloalkyl), —(C$_1$-C$_6$ alkyl)-Ar, -halogen, —NO$_2$ or —CN.

(4uu) —(C$_0$-C$_6$ alkyl)-furanyl optionally substituted with one or more —(C$_1$-C$_6$ alkyl), —(C$_1$-C$_6$ haloalkyl), —(C$_1$-C$_6$ alkyl)-Ar, -halogen, —NO$_2$ or —CN.

(4vv) —(C$_0$-C$_6$ alkyl)-thiophenyl optionally substituted with one or more —(C$_1$-C$_6$ alkyl), —(C$_1$-C$_6$ haloalkyl), —(C$_1$-C$_6$ alkyl)-Ar, -halogen, —NO$_2$ or —CN.

(4ww) —(C$_0$-C$_6$ alkyl)-benzofuranyl optionally substituted with one or more —(C$_1$-C$_6$ alkyl), —(C$_1$-C$_6$ haloalkyl), —(C$_1$-C$_6$ alkyl)-Ar, -halogen, —NO$_2$ or —CN.

(4xx) —(C$_0$-C$_6$ alkyl)-benzothiaphenyl optionally substituted with one or more —(C$_1$-C$_6$ alkyl), —(C$_1$-C$_6$ haloalkyl), —(C$_1$-C$_6$ alkyl)-Ar, -halogen, —NO$_2$ or —CN.

(4yy) -Het.

(4zz) -pyridyl optionally substituted with one or more —(C$_1$-C$_6$ alkyl), —(C$_1$-C$_6$ haloalkyl), —(C$_1$-C$_6$ alkyl)-Ar, -halogen, —NO$_2$ or —CN.

(4aaa) -pyridyl optionally substituted with one or more —(C$_1$-C$_6$ alkyl), —(C$_1$-C$_6$ haloalkyl), -halogen, —NO$_2$ or —CN.

(4bbb) -pyridyl optionally substituted with one or more —(C$_1$-C$_6$ alkyl), -halogen, —NO$_2$ or —CN.

(4ccc) -pyridyl optionally substituted with one or more —(C$_1$-C$_6$ alkyl), -halogen, or —CN.

(4ddd) -pyridyl optionally substituted with one or more —(C$_1$-C$_6$ alkyl) or -halogen.

(4eee) -pyridyl optionally substituted with one or more —(C$_1$-C$_6$ alkyl).

(4fff) -pyridyl optionally substituted with one or more -halogen.

(4ggg) 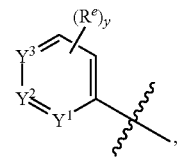

wherein R$^e$ is independently —(C$_1$-C$_6$ alkyl), —O—(C$_1$-C$_6$ alkyl), —(C$_1$-C$_6$ haloalkyl), -halogen, —NO$_2$ or —CN, y is 1, 2, 3, 4 or 5, and Y$^1$, Y$^2$, and Y$^3$ are independently C or N, provided one of Y$^1$, Y$^2$, and Y$^3$ is N.

(4hhh) As group (4ggg), wherein, R$^e$ is independently —O—(C$_1$-C$_6$ alkyl), —(C$_1$-C$_6$ haloalkyl), -halogen or —CN, y is 1, 2, 3 or 4.

(4iii) As group (4ggg), wherein, R$^e$ is independently —O—(C$_1$-C$_6$ alkyl), -halogen or —CN, y is 1 or 2, and one of Y$^1$, Y$^2$ and Y$^3$ is N.

(4jjj) As group (4ggg), wherein, R$^e$ is independently —OMe, fluoro, chloro, bromo, iodo or —CN, y is 1 or 2, and Y$^2$ or Y$^3$ is N.

(4kkk) As group (4ggg), wherein, R$^e$ is independently —OMe, fluoro, chloro, bromo or —CN, y is 1 or 2, and Y$^2$ is N.

(4lll) As group (4ggg), wherein, R$^e$ is independently —OMe, fluoro, chloro, bromo or —CN, y is 1 or 2, and Y$^3$ is N.

(4mmm) 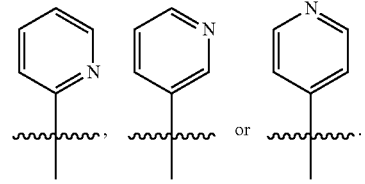

(4nnn) 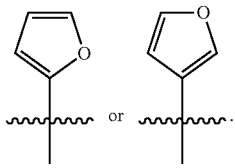 or .

(4ooo) 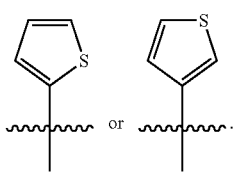 or .

(4ppp) 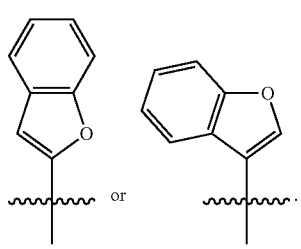 or .

(4qqq) 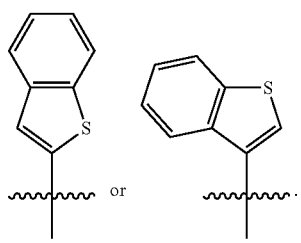 or .

(4rrr) —($C_0$-$C_6$ alkyl)-Cak.
(4sss) -Cak.
(4ttt) -cyclopropyl, -cyclobutyl, -cyclopentyl or -cyclohexyl.
(4uuu) -cyclopropyl, -cyclopentyl or -cyclohexyl.
(4vvv) -cyclopentyl or -cyclohexyl.
(4www) -cyclopropyl.
(4xxx) -cyclopentyl.
(4yyy) -cyclohexyl.

Particular embodiments of this aspect of the invention comprise compounds of any one of the formulae (I), and (Ia)-(Ik), each as defined in each of the following rows, wherein each entry is a group number as defined above (e.g., (1x) refers to $R^1$ is -hydrogen), and a dash "—" indicates that the variable is as defined in embodiment $I_1$ or defined according to any one of the applicable variable definitions (1a)-(4yyy) [e.g., when $R^3$ is a dash, it can be either as defined in embodiment $I_1$ or any one of definitions (3a)-(3ssss)]:

| | (I) | $R^1$ | $R^2$ | $R^3$ | $R^4$ |
|---|---|---|---|---|---|
| (1)-1 | Ia | 1a | 2u | 3a | 4a |
| (1)-2 | Ic | 1h | 2s | 3d | 4d |
| (1)-3 | Id | 1l | 2u | 3e | 4i |
| (1)-4 | Ie | 1m | 2ee | 3f | 4p |
| (1)-5 | Ia | 1n | 2jj | 3g | 4q |
| (1)-6 | Ic | 1o | 2oo | 3m | 4r |
| (1)-7 | Id | 1u | 2tt | 3n | 4s |
| (1)-8 | Ie | 1x | 2a | 3w | 4t |
| (1)-9 | Ia | 1bb | 2s | 3x | 4u |
| (1)-10 | Ia | 1nn | 2u | 3jj | 4v |
| (1)-11 | Ic | 1qq | 2ee | 3kk | 4w |
| (1)-12 | Id | 1rr | 2jj | 3ll | 4cc |
| (1)-13 | Ie | 1ss | 2oo | 3mm | 4dd |
| (1)-14 | Ia | 1tt | 2tt | 3nn | 4ff |
| (1)-15 | Ia | 1uu | 2a | 3oo | 4ll |
| (1)-16 | Ic | — | 2u | 3pp | 4qq |
| (1)-17 | Id | 1ww | 2u | 3ddd | 4rr |
| (1)-18 | Ie | 1yy | 2u | 3hhh | 4ggg |
| (1)-19 | Ia | 1l | 2u | 3a | 4sss |
| (1)-20 | Ic | 1a | 2s | 3d | 4www |
| (1)-21 | — | 1h | 2u | 3e | 4a |
| (1)-22 | Ie | 1l | 2ee | 3f | 4d |
| (1)-23 | Ia | 1m | 2jj | 3g | 4i |
| (1)-24 | Ic | 1n | 2oo | 3m | 4p |
| (1)-25 | Ia | 1o | 2tt | 3n | 4q |
| (1)-26 | Ic | 1u | 2a | 3w | 4r |
| (1)-27 | Id | 1x | 2s | 3x | 4s |
| (1)-28 | Ie | 1bb | 2u | 3jj | 4t |
| (1)-29 | Ia | 1nn | 2ee | 3kk | 4u |
| (1)-30 | Ic | 1qq | 2jj | 3ll | 4v |
| (1)-31 | Id | 1rr | 2oo | 3mm | 4w |
| (1)-32 | — | 1ss | 2tt | 3nn | 4cc |
| (1)-33 | Ia | 1tt | 2a | 3oo | 4dd |
| (1)-34 | Ic | — | 2u | 3pp | 4ff |
| (1)-35 | Id | 1vv | 2u | 3ddd | 4ll |
| (1)-36 | Ie | 1ww | 2u | 3hhh | 4qq |
| (1)-37 | Ia | 1yy | 2u | 3a | 4rr |
| (1)-38 | Ic | 1nn | 2s | 3d | 4ggg |
| (1)-39 | — | 1qq | 2u | 3e | 4sss |
| (1)-40 | Ie | 1rr | 2ee | 3f | 4www |
| (1)-41 | Ia | 1ss | 2u | 3g | 4a |
| (1)-42 | Ic | 1a | 2s | 3m | 4d |
| (1)-43 | Id | 1h | 2u | 3n | 4i |
| (1)-44 | Ie | 1l | 2ee | 3w | 4p |
| (1)-45 | Ia | 1m | 2jj | 3x | 4q |
| (1)-46 | Ic | 1n | 2oo | 3a | 4r |
| (1)-47 | Id | 1o | 2u | 3d | 4s |
| (1)-48 | Ie | 1u | 2s | 3e | 4t |
| (1)-49 | Ia | 1x | 2u | 3f | 4u |
| (1)-50 | Ic | 1bb | 2ee | 3g | 4v |
| (1)-51 | Id | 1nn | — | 3m | 4w |
| (1)-52 | Ia | 1qq | 2oo | 3n | 4a |
| (1)-53 | Ic | 1rr | 2tt | 3w | 4d |
| (1)-54 | — | 1ss | 2a | 3x | 4i |
| (1)-55 | Ia | 1tt | 2s | 3jj | 4p |
| (1)-56 | Ic | 1uu | 2u | 3kk | 4q |
| (1)-57 | Id | 1a | 2ee | 3ll | 4r |
| (1)-58 | Ie | 1h | 2jj | 3mm | 4s |
| (1)-59 | Ia | 1l | 2oo | 3nn | 4t |
| (1)-60 | — | 1m | 2tt | 3oo | 4u |
| (1)-61 | Id | 1n | 2a | 3pp | 4v |
| (1)-62 | Ie | 1o | 2u | 3ddd | 4w |
| (1)-63 | Ia | 1u | 2u | 3hhh | 4cc |
| (1)-64 | Ic | 1x | 2u | 3a | 4dd |
| (1)-65 | Id | 1bb | 2u | 3d | 4ff |
| (1)-66 | Ia | 1nn | 2s | 3a | 4ll |
| (1)-67 | Ic | 1qq | 2u | 3d | 4qq |
| (1)-68 | Id | 1rr | 2ee | 3e | 4rr |
| (1)-69 | Ie | 1ss | 2jj | 3f | 4ggg |
| (1)-70 | Ia | 1tt | 2oo | 3g | 4sss |
| (1)-71 | Ic | 1uu | 2tt | 3m | 4www |
| (1)-72 | Id | 1vv | 2a | 3n | 4a |
| (1)-73 | Ie | 1ww | 2s | 3w | 4d |
| (1)-74 | Ia | 1yy | 2u | 3x | 4i |
| (1)-75 | Ic | 1a | 2ee | 3jj | 4p |
| (1)-76 | Id | 1h | 2jj | 3kk | 4a |
| (1)-77 | Ie | 1l | 2oo | 3a | 4d |
| (1)-78 | Ia | 1m | 2tt | 3d | 4i |
| (1)-79 | Ic | 1n | 2a | 3e | 4p |
| (1)-80 | Id | 1o | 2u | 3f | 4q |
| (1)-81 | Ie | 1u | 2u | 3g | 4a |
| (1)-82 | Ia | 1x | 2u | 3m | 4d |
| (1)-83 | Ic | 1bb | 2u | 3n | 4i |
| (1)-84 | Id | 1nn | 2s | 3a | 4p |

-continued

| (I) | R¹ | R² | R³ | R⁴ |
|---|---|---|---|---|
| (1)-85 | Ie | 1qq | 2u | 3d | 4q |
| (1)-86 | Ia | 1n | 2ee | 3e | 4r |
| (1)-87 | Ic | 1ss | 2jj | 3f | 4s |
| (1)-88 | Id | 1tt | 2oo | 3g | 4t |
| (1)-89 | — | 1uu | 2tt | 3m | 4u |
| (1)-90 | Ia | 1vv | 2a | 3n | 4v |
| (1)-91 | Ic | 1ww | 2s | 3w | 4w |
| (1)-92 | Id | 1yy | 2u | 3x | 4cc |
| (1)-93 | Ie | 1a | 2ee | 3jj | 4dd |
| (1)-94 | Ia | 1h | 2jj | 3kk | 4ff |
| (1)-95 | Ia | 1l | 2oo | 3ll | 4ll |
| (1)-96 | Ic | 1m | 2tt | 3mm | 4qq |
| (1)-97 | — | 1a | 2a | 3a | 4rr |
| (1)-98 | Ie | 1h | 2u | 3d | 4ggg |
| (1)-99 | Ia | 1l | 2u | 3e | 4sss |
| (1)-100 | Ic | 1m | 2u | 3f | 4www |
| (1)-101 | Id | 1n | 2u | 3g | 4a |
| (1)-102 | Ie | 1o | 2s | 3m | 4d |
| (1)-103 | Ia | 1u | 2u | 3n | 4i |
| (1)-104 | Ic | 1x | 2ee | 3w | 4p |
| (1)-105 | Id | 1bb | 2jj | 3x | 4q |
| (1)-106 | Ie | 1nn | 2oo | 3jj | 4r |
| (1)-107 | Ia | 1qq | 2tt | 3kk | 4s |
| (1)-108 | Ic | 1rr | 2a | 3ll | 4t |
| (1)-109 | Ia | 1ss | 2s | 3mm | 4a |
| (1)-110 | Ic | 1tt | 2u | 3nn | 4d |
| (1)-111 | Id | 1uu | 2ee | 3oo | 4i |
| (1)-112 | Ie | 1vv | 2u | 3pp | 4p |
| (1)-113 | Ia | 1ww | 2s | 3ddd | 4q |
| (1)-114 | Ic | 1yy | 2u | 3hhh | 4r |
| (1)-115 | — | 1a | 2s | 3a | 4s |
| (1)-116 | — | 1h | 2u | 3d | 4t |
| (1)-117 | Id | 1l | 2ee | 3e | 4u |
| (1)-118 | Ie | 1m | 2jj | 3f | 4v |
| (1)-119 | Ia | 1n | 2oo | 3g | 4w |
| (1)-120 | Ic | 1o | 2tt | 3m | 4cc |
| (1)-121 | Id | 1u | 2a | 3n | 4dd |
| (1)-122 | Ie | 1x | 2s | 3w | 4ff |
| (1)-123 | Ia | 1bb | 2u | 3x | 4ll |
| (1)-124 | Ic | — | 2s | 3jj | 4qq |
| (1)-125 | Id | 1qq | 2u | 3kk | 4a |
| (1)-126 | Ie | 1n | 2ee | 3ll | 4d |
| (1)-127 | Ia | 1ss | 2jj | 3mm | 4i |
| (1)-128 | Ia | 1tt | 2oo | 3nn | 4p |
| (1)-129 | — | 1uu | 2tt | 3oo | 4q |
| (1)-130 | Id | — | 2a | 3pp | 4r |
| (1)-131 | Ie | 1ww | 2s | 3ddd | 4s |
| (1)-132 | Ia | 1yy | 2u | 3hhh | 4t |
| (1)-133 | Ic | — | 2ee | 3a | 4u |
| (1)-134 | Id | 1h | 2jj | 3d | 4v |
| (1)-135 | Ie | 1l | 2oo | 3e | 4w |
| (1)-136 | Ia | 1m | 2tt | 3f | 4cc |
| (1)-137 | Ic | 1n | 2a | 3g | 4dd |
| (1)-138 | Id | 1o | 2u | — | 4ff |
| (1)-139 | Ie | 1u | 2u | 3n | 4ll |
| (1)-140 | Ia | 1x | 2u | 3w | — |
| (1)-141 | Ic | 1bb | 2u | 3x | 4rr |
| (1)-142 | — | 1nn | 2s | 3jj | 4ggg |
| (1)-143 | Ie | 1qq | 2u | 3kk | 4sss |
| (1)-144 | Ia | 1rr | 2ee | 3ll | 4www |
| (1)-145 | Ic | 1ss | — | 3mm | 4a |
| (1)-146 | Id | 1tt | 2oo | 3nn | 4d |
| (1)-147 | Ie | 1uu | 2tt | 3oo | 4i |
| (1)-148 | Ia | 1vv | 2a | 3pp | 4p |
| (1)-149 | Ic | 1ww | 2s | 3ddd | 4q |
| (1)-150 | Id | 1yy | 2u | 3hhh | 4r |
| (1)-151 | Ie | 1a | 2ee | 3a | 4s |
| (1)-152 | Ia | 1h | 2jj | 3d | 4t |
| (1)-153 | Ic | 1l | 2oo | 3e | 4u |
| (1)-154 | Id | 1m | — | 3f | 4v |
| (1)-155 | Ie | 1n | 2a | 3g | 4w |
| (1)-156 | Ia | 1o | 2u | 3m | 4a |
| (1)-157 | Ic | 1u | 2u | 3n | 4d |
| (1)-158 | Id | 1x | 2u | 3w | 4i |
| (1)-159 | Ie | 1bb | 2u | 3x | 4p |
| (1)-160 | Ia | — | 2s | 3jj | 4q |
| (1)-161 | Ic | 1qq | 2u | 3kk | 4r |
| (1)-162 | Id | 1rr | 2ee | 3ll | 4s |
| (1)-163 | Ie | 1ss | — | 3mm | 4t |
| (1)-164 | Ia | 1tt | 2oo | 3nn | 4u |
| (1)-165 | Ic | — | 2tt | 3oo | 4v |
| (1)-166 | Id | 1vv | 2a | 3pp | 4a |
| (1)-167 | — | 1ww | 2s | 3ddd | 4d |
| (1)-168 | Ia | 1yy | 2u | 3hhh | 4i |
| (1)-169 | Ic | 1a | 2ee | 3a | 4p |
| (1)-170 | Id | 1h | 2jj | 3d | 4q |
| (1)-171 | Ie | 1l | 2oo | 3e | 4r |
| (1)-172 | Ia | 1m | 2tt | 3f | 4s |
| (1)-173 | Ic | 1n | 2a | 3g | 4t |
| (1)-174 | Id | 1o | 2u | 3m | 4u |
| (1)-175 | Ie | 1u | 2u | 3n | 4v |
| (1)-176 | Ia | 1x | 2u | 3a | 4w |
| (1)-177 | Ic | 1bb | 2u | 3d | 4cc |
| (1)-178 | Id | 1nn | 2s | 3e | 4dd |
| (1)-179 | Ie | 1qq | 2u | 3f | 4ff |
| (1)-180 | Ia | 1n | 2ee | 3g | 4ll |
| (1)-181 | Ic | 1ss | — | 3m | 4qq |
| (1)-182 | — | 1tt | 2oo | 3n | 4rr |
| (1)-183 | Ie | 1uu | 2tt | 3w | 4ggg |
| (1)-184 | Ia | 1vv | 2a | 3x | 4sss |
| (1)-185 | Ic | 1ww | 2s | 3jj | 4www |
| (1)-186 | — | 1yy | 2u | 3kk | 4a |
| (1)-187 | Ie | 1a | 2ee | 3ll | 4d |
| (1)-188 | Ia | 1h | 2jj | 3mm | 4i |
| (1)-189 | Ic | 1l | 2oo | 3nn | 4p |
| (1)-190 | Id | 1a | 2u | 3oo | 4q |
| (1)-191 | — | 1h | 2s | 3pp | 4r |
| (1)-192 | Ia | 1l | 2u | 3ddd | 4s |
| (1)-193 | Ic | 1m | 2ee | — | 4t |
| (1)-194 | Id | 1n | 2jj | 3a | 4u |
| (1)-195 | Ie | 1o | 2oo | 3d | 4v |
| (1)-196 | Ia | 1u | 2tt | 3e | — |
| (1)-197 | Ic | 1x | 2a | 3f | 4a |
| (1)-198 | Id | 1bb | 2s | 3g | 4d |
| (1)-199 | Ie | 1l | 2u | — | 4i |
| (1)-200 | Ia | 1m | 2ee | 3n | 4p |
| (1)-201 | Ic | 1n | 2u | 3w | 4q |
| (1)-202 | Id | 1o | 2s | 3x | 4r |
| (1)-203 | Ie | 1u | 2u | 3jj | 4s |
| (1)-204 | Ia | 1x | 2s | 3kk | 4t |
| (1)-205 | Ic | 1bb | 2u | 3a | 4u |
| (1)-206 | Id | 1nn | 2ee | 3d | 4v |
| (1)-207 | Ie | 1qq | 2jj | 3e | 4w |
| (1)-208 | Ia | 1rr | 2oo | 3f | 4cc |
| (1)-209 | Ic | 1ss | 2tt | 3g | 4dd |
| (1)-210 | Id | 1tt | 2a | 3m | 4ff |
| (1)-211 | Ie | 1a | 2s | 3n | 4ll |
| (1)-212 | Ia | 1h | 2u | 3w | 4qq |
| (1)-213 | Ic | 1l | 2ee | 3a | 4a |
| (1)-214 | — | 1m | 2jj | 3d | 4d |
| (1)-215 | Ie | 1n | 2oo | 3e | 4i |
| (1)-216 | Ia | 1o | 2tt | 3f | 4p |
| (1)-217 | Ic | — | 2a | 3g | 4q |
| (1)-218 | Id | 1x | 2u | 3m | 4r |
| (1)-219 | Ie | 1bb | 2u | 3n | 4s |
| (1)-220 | Ia | 1nn | 2u | 3w | 4t |
| (1)-221 | Ic | 1a | 2u | 3x | 4u |
| (1)-222 | — | 1h | 2s | 3jj | 4v |
| (1)-223 | Ie | 1l | 2u | 3kk | 4w |
| (1)-224 | Ia | 1m | 2ee | 3ll | 4cc |
| (1)-225 | Ic | 1n | 2jj | 3mm | 4dd |
| (1)-226 | Id | 1o | 2oo | 3nn | 4ff |
| (1)-227 | Ie | 1u | 2tt | 3oo | 4ll |
| (1)-228 | Ia | 1x | 2a | 3pp | — |
| (1)-229 | Ic | 1bb | 2s | 3ddd | 4rr |
| (1)-230 | Id | 1nn | 2u | 3hhh | 4ggg |
| (1)-231 | Ie | 1qq | 2ee | 3a | 4sss |
| (1)-232 | Ia | 1rr | 2jj | 3d | 4www |
| (1)-233 | Ic | 1ss | — | 3e | 4a |
| (1)-234 | — | 1tt | 2tt | 3f | 4d |
| (1)-235 | Ie | 1uu | 2a | 3g | 4i |
| (1)-236 | Ia | 1vv | 2s | 3m | 4p |
| (1)-237 | Ic | — | 2u | 3n | 4q |
| (1)-238 | Id | 1a | 2ee | 3w | 4r |

| (I) | R¹ | R² | R³ | R⁴ |
|---|---|---|---|---|
| (1)-239 | Ie | 1h | 2jj | 3x | 4s |
| (1)-240 | Ia | 1l | 2oo | 3jj | 4t |
| (1)-241 | Ic | 1m | 2tt | 3kk | 4u |
| (1)-242 | Id | 1n | 2a | 3ll | 4v |
| (1)-243 | Ie | 1o | 2s | 3mm | 4w |
| (1)-244 | Ia | 1u | 2oo | 3nn | 4cc |
| (1)-245 | Ic | 1x | 2tt | 3oo | 4dd |
| (1)-246 | Id | 1bb | 2a | 3pp | 4a |
| (1)-247 | — | 1nn | 2s | 3ddd | 4d |
| (1)-248 | Ia | 1qq | 2u | 3hhh | 4i |
| (1)-249 | Ic | 1n | 2ee | 3a | 4p |
| (1)-250 | — | 1ss | 2jj | 3d | 4q |
| (1)-251 | Ie | 1tt | 2oo | 3e | 4r |
| (1)-252 | Ia | 1uu | 2tt | 3f | 4s |
| (1)-253 | Ic | — | 2a | 3g | 4t |
| (1)-254 | Id | 1ww | 2u | — | 4u |
| (1)-255 | Ie | 1yy | 2u | 3n | 4v |
| (1)-256 | Ia | 1a | 2u | 3w | 4w |
| (1)-257 | Ic | 1h | 2u | 3x | 4cc |
| (1)-258 | Id | 1l | — | 3jj | 4dd |
| (1)-259 | Ie | 1m | 2u | 3kk | — |
| (1)-260 | Ia | 1n | 2ee | 3ll | 4ll |
| (1)-261 | Ic | 1o | 2jj | 3mm | 4qq |
| (1)-262 | Id | — | 2oo | 3nn | 4rr |
| (1)-263 | Ie | 1x | 2tt | 3oo | 4ggg |
| (1)-264 | Ia | 1bb | 2a | 3pp | 4sss |
| (1)-265 | Ic | 1nn | 2s | 3ddd | 4www |
| (1)-266 | Id | 1qq | 2u | 3hhh | 4a |
| (1)-267 | — | 1rr | 2ee | 3a | 4d |
| (1)-268 | Ia | 1ss | 2jj | 3d | — |
| (1)-269 | Ic | 1tt | 2oo | 3e | 4p |
| (1)-270 | — | 1uu | 2tt | 3f | 4q |
| (1)-271 | Ie | 1vv | 2a | 3g | 4r |
| (1)-272 | Ia | 1ww | 2u | 3m | 4s |
| (1)-273 | Ic | — | 2u | 3n | 4t |
| (1)-274 | Id | 1a | 2u | 3w | 4u |

In embodiment II$_1$ of this aspect, the invention comprises compounds according to formula (II),

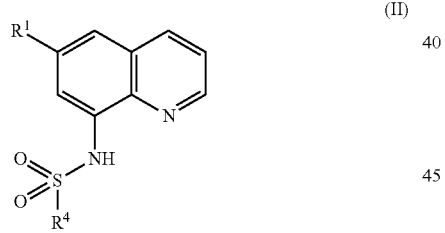

(II)

wherein
R¹ is as described above in groups (1a)-(1bbb), provided that R¹ is not hydrogen; and
R⁴ is as described above in groups (4a)-(4yyy).

In embodiment II$_2$, the compounds are of embodiment II$_1$, provided that the compound is not:
N-(6-chloroquinolin-8-yl)benzenesulfonamide;
N-(6-fluoroquinolin-8-yl)benzenesulfonamide;
N-(5-chloro-6-fluoroquinolin-8-yl)benzenesulfonamide;
N-(6-(trifluoromethoxy)quinolin-8-yl)benzenesulfonamide;
2,6-difluoro-N-(6-fluoroquinolin-8-yl)benzenesulfonamide;
4-chloro-2-fluoro-N-(6-fluoroquinolin-8-yl)benzenesulfonamide;
N-(6-fluoroquinolin-8-yl)pyridine-3-sulfonamide;
N-(5,6-difluoroquinolin-8-yl)benzenesulfonamide;
N-(6-(trifluoromethoxy)quinolin-8-yl)-6-(trifluoromethyl)pyridine-3-sulfonamide;
N-(6-(trifluoromethoxy)quinolin-8-yl)pyridine-2-sulfonamide;
N-(6-fluoroquinolin-8-yl)pyridine-3-sulfonamide;
N-(6-(trifluoromethoxy)quinolin-8-yl)pyridine-3-sulfonamide;
6-cyano-N-(6-(trifluoromethoxy)quinolin-8-yl)pyridine-3-sulfonamide;
6-cyano-N-(6-fluoroquinolin-8-yl)pyridine-3-sulfonamide;
N-(6-bromoquinolin-8-yl)benzenesulfonamide;
N-(5-chloro-6-fluoroquinolin-8-yl)benzenesulfonamide; or
N-(5,6-difluoroquinolin-8-yl)benzenesulfonamide.

In embodiment II$_3$, the compound is of embodiment II$_1$ or II$_2$, wherein
R¹ is —(C$_1$-C$_6$ haloalkyl), —Y—(C$_1$-C$_6$ haloalkyl), —Y—(C$_0$-C$_6$ alkyl)-Ar, —Y—(C$_0$-C$_6$ alkyl)-Het, —Y—(C$_0$-C$_6$ alkyl)-Cak, —Y—(C$_0$-C$_6$ alkyl)-Hca, —NO$_2$ or —CN,
wherein Y is O, S, N(R⁵), and R⁵ is -hydrogen or —(C$_1$-C$_6$ alkyl),
provided that the compound is not:
N-(6-(trifluoromethoxy)quinolin-8-yl)benzenesulfonamide;
N-(6-(trifluoromethoxy)quinolin-8-yl)-6-(trifluoromethyl)pyridine-3-sulfonamide;
N-(6-(trifluoromethoxy)quinolin-8-yl)pyridine-2-sulfonamide;
N-(6-(trifluoromethoxy)quinolin-8-yl)pyridine-3-sulfonamide; or
6-cyano-N-(6-(trifluoromethoxy)quinolin-8-yl)pyridine-3-sulfonamide.

In embodiment II$_4$, the compounds of the invention are one of formulae (IIa)-(IIh), wherein R⁴ is as defined in any embodiment hereinabove:

Structural Formula (II) is One of Formulae (IIa)-(IIh):

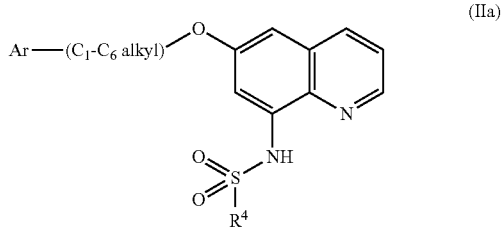

(IIa)

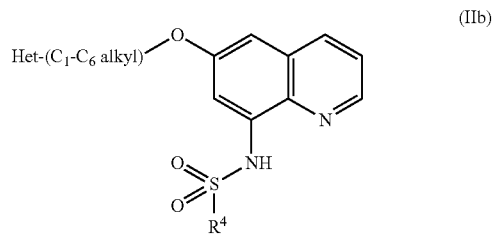

(IIb)

-continued (IIc) 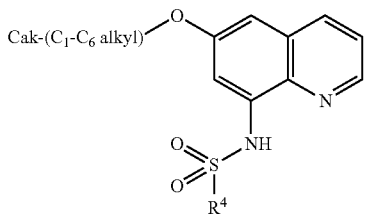

(IId) 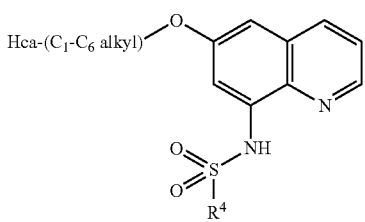

(IIe) 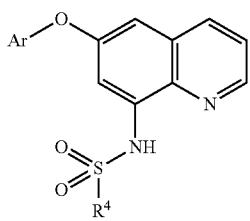

(IIf) 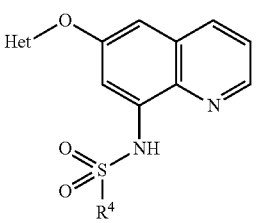

(IIg) 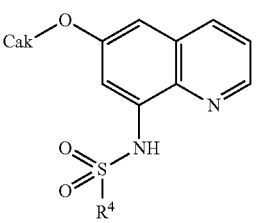

(IIh) 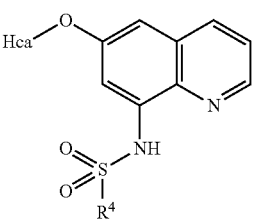

In embodiment III$_1$, the invention comprises compounds according to formula (III),

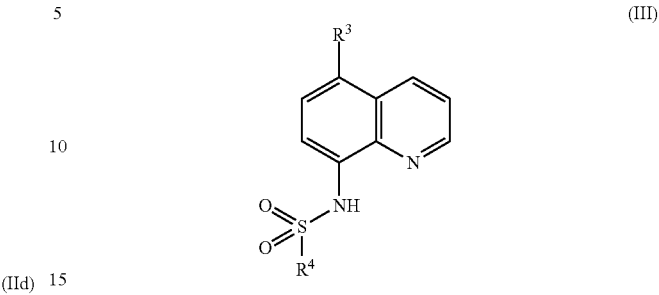

wherein

R$^3$ is as described above in groups (3a)-(3ssss), provided that R$^3$ is not hydrogen; and R$^4$ is as described above in groups (4a)-(4yyy).

In embodiment III$_2$, the compounds are of embodiment III$_c$, provided that the compound is not:

N-(5-bromoquinolin-8-yl)-4-methylbenzenesulfonamide

N-(5-chloroquinolin-8-yl)benzenesulfonamide;

N-(5-bromoquinolin-8-yl)benzenesulfonamide;

N-(5,7-dichloroquinolin-8-yl)-4-methylbenzenesulfonamide;

N-(5,7-dichloroquinolin-8-yl)-2,4,6-trimethylbenzenesulfonamide;

2,4-dichloro-N-(5-chloroquinolin-8-yl)benzenesulfonamide;

N-(5-chloroquinolin-8-yl)pyridine-3-sulfonamide;

2-amino-N-(5-chloroquinolin-8-yl)-4-methylbenzenesulfonamide;

N-(5-chloro-6-fluoroquinolin-8-yl)benzenesulfonamide;

N-(5,6-difluoroquinolin-8-yl)benzenesulfonamide;

N-(5-fluoroquinolin-8-yl)benzenesulfonamide;

N-(5-morpholinoquinolin-8-yl)benzenesulfonamide;

N-(5-bromoquinolin-8-yl)-5-(2-(methylthio)pyrimidin-4-yl)thiophene-2-sulfonamide;

N-(5-bromoquinolin-8-yl)-5-(oxazol-5-yl)thiophene-2-sulfonamide; or

N-(5-bromoquinolin-8-yl)-4-(2-methylpyrimidin-4-yl)benzenesulfonamide.

In embodiment III$_3$, the compounds are of embodiment III$_1$ or III$_2$, wherein R$^3$ is —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —NO$_2$ or —CN, provided that the compound is not:

N-(5-morpholinoquinolin-8-yl)benzenesulfonamide.

The invention further comprises subgenera of embodiments III$_1$, III$_2$, or III$_3$, in which structural formula (III), R$^3$ and R$^4$ are any combination of groups as defined hereinabove, including without limitation, the following (e.g., structural formula (III) is formula (Me), R$^3$ is group (3jj), and R$^4$ is group (4q)):

Structural Formula (III) is One of Formulae (IIIa)-(IIIk):

(IIIa) (C₁-C₆ alkyl)—Ar
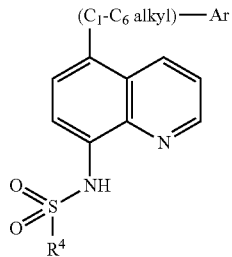

(IIIb) (C₁-C₆ alkyl)-Het
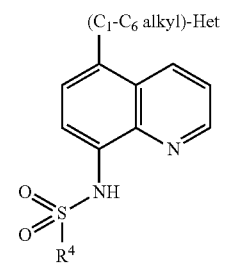

(IIIc) (C₁-C₆ alkyl)-Cak
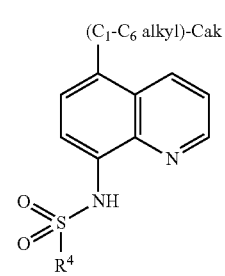

(IIId) (C₁-C₆ alkyl)-Hca
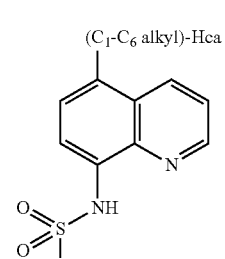

(IIIe) (C₀-C₆ alkyl)—Ar
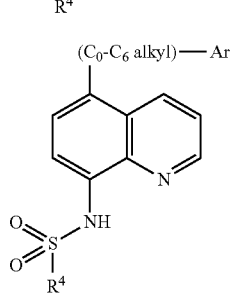

(IIIf) (C₀-C₆ alkyl)-Het
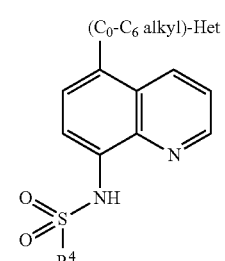
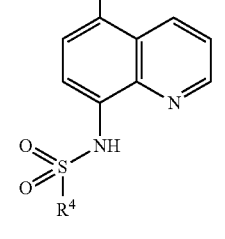

-continued (IIIg) (C₀-C₆ alkyl)-Hca
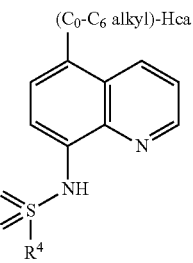

(IIIh) Ar
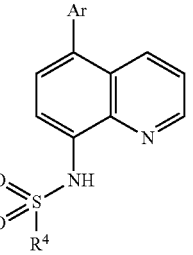

(IIIi) Het
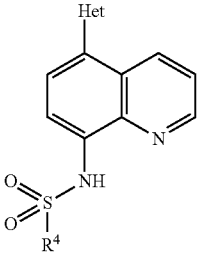

(IIIj) Cak
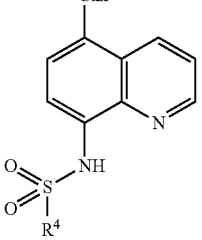

(IIIk) Hca

In some embodiments, where the compound has a structure according to formula (I), (III), (III) or (IIIk), when $R^3$ is Hca, Hca is not -morpholinyl. In other embodiments, where the compound has a structure according to formula (I), (III), (IIIg) or (IIIk), the compound is not N-(5-morpholinoquinolin-8-yl)benzenesulfonamide.

Particular embodiments of this aspect of the invention comprise compounds of any one of the formulae (III), and (IIIa)-(IIIk), each as defined in each of the following rows, wherein each entry is a group number as defined above (e.g., (3v) refers to $R^3$ is -bromo), and a dash "—" indicates that the variable is as defined in embodiment $I_1$ or defined according to any one of the applicable variable definitions (3a)-(3ssss) and (4a)-(4yyy) [e.g., when $R^4$ is a dash, it can be either as defined in embodiment $I_1$ or any one of definitions (4a)-(4yyy)]:

|  | (III) | $R^3$ | $R^4$ |
|---|---|---|---|
| (3)-1 | IIIe | 3aa | 4a |
| (3)-2 | IIIe | 3bb | 4d |
| (3)-3 | IIIe | 3cc | 4i |
| (3)-4 | IIIe | 3dd | 4p |
| (3)-5 | IIIe | 3ee | 4q |
| (3)-6 | IIIe | 3ff | 4r |
| (3)-7 | IIIe | 3gg | 4s |
| (3)-8 | IIIe | 3hh | 4t |
| (3)-9 | IIIe | 3ii | 4u |
| (3)-10 | IIIe | 3jj | 4v |
| (3)-11 | IIIe | 3kk | 4w |
| (3)-12 | IIIe | 3ll | 4cc |
| (3)-13 | IIIe | 3mm | 4dd |
| (3)-14 | IIIe | 3nn | 4ff |
| (3)-15 | IIIe | 3oo | 4ll |
| (3)-16 | IIIh | 3aa | 4qq |
| (3)-17 | IIIh | 3bb | 4rr |
| (3)-18 | IIIh | 3cc | 4ggg |
| (3)-19 | IIIh | 3dd | 4sss |
| (3)-20 | IIIh | 3ee | 4www |
| (3)-21 | IIIh | 3ff | 4a |
| (3)-22 | IIIh | 3gg | 4d |
| (3)-23 | IIIh | 3hh | 4i |
| (3)-24 | IIIh | 3ii | 4p |
| (3)-25 | IIIh | 3jj | 4q |
| (3)-26 | IIIh | 3kk | 4r |
| (3)-27 | IIIh | 3ll | 4s |
| (3)-28 | IIIh | 3mm | 4t |
| (3)-29 | IIIh | 3nn | 4u |
| (3)-30 | IIIh | 3oo | 4v |
| (3)-31 | IIIe | 3jj | 4a |
| (3)-32 | IIIe | 3jj | 4d |
| (3)-33 | IIIe | 3jj | 4i |
| (3)-34 | IIIe | 3jj | 4p |
| (3)-35 | IIIe | 3jj | 4q |
| (3)-36 | IIIe | 3jj | 4r |
| (3)-37 | IIIe | 3jj | 4s |
| (3)-38 | IIIe | 3jj | 4t |
| (3)-39 | IIIe | 3jj | 4u |
| (3)-40 | IIIe | 3jj | 4v |
| (3)-41 | IIIe | 3jj | 4w |
| (3)-42 | IIIe | 3jj | 4cc |
| (3)-43 | IIIe | 3jj | 4dd |
| (3)-44 | IIIe | 3jj | 4ff |
| (3)-45 | IIIe | 3jj | 4ll |
| (3)-46 | IIIe | 3jj | 4qq |
| (3)-47 | IIIe | 3jj | 4rr |
| (3)-48 | IIIe | 3jj | 4ggg |
| (3)-49 | IIIe | 3jj | 4sss |
| (3)-50 | IIIe | 3jj | 4www |
| (3)-51 | IIIf | 3qq | 4a |
| (3)-52 | IIIf | 3rr | 4d |
| (3)-53 | IIIf | 3ss | 4i |
| (3)-54 | IIIf | 3tt | 4p |
| (3)-55 | IIIf | 3uu | 4q |
| (3)-56 | IIIf | 3ww | 4r |
| (3)-57 | IIIf | 3xx | 4s |
| (3)-58 | IIIf | 3yy | 4t |
| (3)-59 | IIIf | 3zz | 4u |
| (3)-60 | IIIf | 3aaa | 4v |
| (3)-61 | IIIf | 3bbb | 4w |
| (3)-62 | IIIf | 3ccc | 4cc |
| (3)-63 | IIIf | 3ddd | 4dd |
| (3)-64 | IIIf | 3eee | 4ff |
| (3)-65 | IIIf | 3fff | 4ll |
| (3)-66 | IIIf | 3ggg | 4qq |
| (3)-67 | IIIf | 3hhh | 4rr |
| (3)-68 | IIIf | 3iii | 4ggg |
| (3)-69 | IIIf | 3jjj | 4sss |
| (3)-70 | IIIf | 3mmm | 4www |
| (3)-71 | IIIf | 3ppp | 4w |
| (3)-72 | IIIf | 3sss | 4cc |
| (3)-73 | IIIf | 3vvv | 4dd |
| (3)-74 | IIIi | 3qq | 4a |
| (3)-75 | IIIi | 3rr | 4d |
| (3)-76 | IIIi | 3ss | 4i |
| (3)-77 | IIIi | 3tt | 4p |
| (3)-78 | IIIi | 3uu | 4q |
| (3)-79 | IIIi | 3ww | 4r |
| (3)-80 | IIIi | 3xx | 4s |
| (3)-81 | IIIi | 3yy | 4t |
| (3)-82 | IIIi | 3zz | 4u |
| (3)-83 | IIIi | 3aaa | 4v |
| (3)-84 | IIIi | 3bbb | 4w |
| (3)-85 | IIIi | 3ccc | 4cc |
| (3)-86 | IIIi | 3ddd | 4dd |
| (3)-87 | IIIi | 3eee | 4ff |
| (3)-88 | IIIi | 3fff | 4ll |
| (3)-89 | IIIi | 3ggg | 4qq |
| (3)-90 | IIIi | 3hhh | 4rr |
| (3)-91 | IIIi | 3iii | 4ggg |
| (3)-92 | IIIi | 3jjj | 4sss |
| (3)-93 | IIIi | 3mmm | 4www |
| (3)-94 | IIIi | 3ppp | 4ff |
| (3)-95 | IIIi | 3sss | 4ll |
| (3)-96 | IIIi | 3vvv | 4qq |
| (3)-97 | IIIf | 3ddd | 4a |
| (3)-98 | IIIf | 3ddd | 4d |
| (3)-99 | IIIf | 3ddd | 4i |
| (3)-100 | IIIf | 3ddd | 4p |
| (3)-101 | IIIf | 3ddd | 4q |
| (3)-102 | IIIf | 3ddd | 4r |
| (3)-103 | IIIf | 3ddd | 4s |
| (3)-104 | IIIf | 3ddd | 4t |
| (3)-105 | IIIf | 3ddd | 4u |
| (3)-106 | IIIf | 3ddd | 4v |
| (3)-107 | IIIf | 3ddd | 4w |
| (3)-108 | IIIf | 3ddd | 4cc |
| (3)-109 | IIIf | 3ddd | 4dd |
| (3)-110 | IIIf | 3ddd | 4ff |
| (3)-111 | IIIf | 3ddd | 4ll |
| (3)-112 | IIIf | 3ddd | 4qq |
| (3)-113 | IIIf | 3ddd | 4rr |
| (3)-114 | IIIf | 3ddd | 4ggg |
| (3)-115 | IIIf | 3ddd | 4sss |
| (3)-116 | IIIf | 3ddd | 4www |
| (3)-117 | IIIj | 3aaaa | 4a |
| (3)-118 | IIIj | 3bbbb | 4d |
| (3)-119 | IIIj | 3cccc | 4i |
| (3)-120 | IIIj | 3dddd | 4p |
| (3)-121 | IIIj | 3eeee | 4q |
| (3)-122 | IIIj | 3aaaa | 4r |
| (3)-123 | IIIj | 3bbbb | 4s |
| (3)-124 | IIIj | 3cccc | 4t |
| (3)-125 | IIIj | 3dddd | 4u |
| (3)-126 | IIIj | 3eeee | 4v |
| (3)-127 | IIIj | 3aaaa | 4w |
| (3)-128 | IIIj | 3bbbb | 4cc |
| (3)-129 | IIIj | 3cccc | 4dd |
| (3)-130 | IIIj | 3dddd | 4ff |
| (3)-131 | IIIj | 3eeee | 4ll |
| (3)-132 | IIIj | 3aaaa | 4qq |
| (3)-133 | IIIj | 3bbbb | 4rr |
| (3)-134 | IIIj | 3cccc | 4ggg |
| (3)-135 | IIIj | 3dddd | 4sss |
| (3)-136 | IIIj | 3eeee | 4www |
| (3)-137 | IIIg | 3hhhh | 4a |
| (3)-138 | IIIg | 3iiii | 4d |
| (3)-139 | IIIg | 3jjjj | 4i |
| (3)-140 | IIIg | 3kkkk | 4p |
| (3)-141 | IIIg | 3llll | 4q |
| (3)-142 | IIIg | 3nnnn | 4r |
| (3)-143 | IIIg | 3oooo | 4s |
| (3)-144 | IIIg | 3pppp | 4t |
| (3)-145 | IIIg | 3ssss | 4u |
| (3)-146 | IIIg | 3hhhh | 4v |
| (3)-147 | IIIg | 3iiii | 4w |
| (3)-148 | IIIg | 3jjjj | 4cc |
| (3)-149 | IIIg | 3kkkk | 4dd |
| (3)-150 | IIIg | 3llll | 4ff |

-continued

|  | (III) | R³ | R⁴ |
|---|---|---|---|
| (3)-151 | IIIg | 3nnnn | 4ll |
| (3)-152 | IIIg | 3oooo | 4qq |
| (3)-153 | IIIg | 3pppp | 4rr |
| (3)-154 | IIIg | 3ssss | 4ggg |
| (3)-155 | IIIk | 3hhhh | 4a |
| (3)-156 | IIIk | 3iiii | 4d |
| (3)-157 | IIIk | 3jjjj | 4i |
| (3)-158 | IIIk | 3kkkk | 4p |
| (3)-159 | IIIk | 3llll | 4q |
| (3)-160 | IIIk | 3nnnn | 4r |
| (3)-161 | IIIk | 3oooo | 4s |
| (3)-162 | IIIk | 3pppp | 4t |
| (3)-163 | IIIk | 3ssss | 4u |
| (3)-164 | IIIk | 3hhhh | 4v |
| (3)-165 | IIIk | 3iiii | 4w |
| (3)-166 | IIIk | 3jjjj | 4cc |
| (3)-167 | IIIk | 3kkkk | 4dd |
| (3)-168 | IIIk | 3llll | 4ff |
| (3)-169 | IIIk | 3nnnn | 4ll |
| (3)-170 | IIIk | 3oooo | 4qq |
| (3)-171 | IIIk | 3pppp | 4rr |
| (3)-172 | IIIk | 3ssss | 4ggg |
| (3)-173 | IIIg | 3hhhh | 4a |

-continued

|  | (III) | R³ | R⁴ |
|---|---|---|---|
| (3)-174 | IIIg | 3hhhh | 4d |
| (3)-175 | IIIg | 3hhhh | 4i |
| (3)-176 | IIIg | 3hhhh | 4p |
| (3)-177 | IIIg | 3hhhh | 4q |
| (3)-178 | IIIg | 3hhhh | 4r |
| (3)-179 | IIIg | 3hhhh | 4s |
| (3)-180 | IIIg | 3hhhh | 4t |
| (3)-181 | IIIg | 3hhhh | 4u |
| (3)-182 | IIIg | 3hhhh | 4v |
| (3)-183 | IIIg | 3hhhh | 4w |
| (3)-184 | IIIg | 3hhhh | 4cc |
| (3)-185 | IIIg | 3hhhh | 4dd |
| (3)-186 | IIIg | 3hhhh | 4ff |
| (3)-187 | IIIg | 3hhhh | 4ll |
| (3)-188 | IIIg | 3hhhh | 4qq |
| (3)-189 | IIIg | 3hhhh | 4rr |
| (3)-190 | IIIg | 3hhhh | 4ggg |
| (3)-191 | IIIg | 3hhhh | 4sss |
| (3)-192 | IIIg | 3hhhh | 4www |

In some embodiments, the compound of formulae (I), (Ia-k), (II), (IIa-h), (III) or (IIIa-k) is:

| No. | Structure | Name |
|---|---|---|
| 1 | [5-bromoquinolin-8-yl with N-tosylsulfonamide structure] | N-(5-bromoquinolin-8-yl)-4-methylbenzenesulfonamide |
| 2 | [5-bromoquinolin-8-yl with N-phenylsulfonamide structure] | N-(5-bromoquinolin-8-yl)benzenesulfonamide |
| 4 | [5-phenylquinolin-8-yl with N-tosylsulfonamide structure] | 4-methyl-N-(5-phenylquinolin-8-yl)benzenesulfonamide |

-continued
| No. | Structure | Name |
|---|---|---|
| 5 | 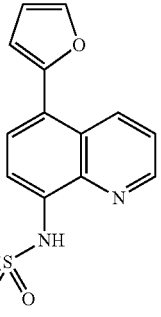 | N-(5-(furan-2-yl)quinolin-8-yl)-4-methylbenzenesulfonamide |
| 6 | 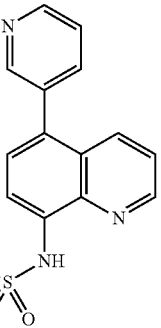 | 4-methyl-N-(5-(pyridin-3-yl)quinolin-8-yl)benzenesulfonamide |
| 7 | 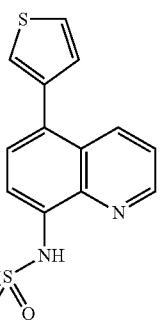 | 4-methyl-N-(5-(thiophen-3-yl)quinolin-8-yl)benzenesulfonamide |
| 8 | 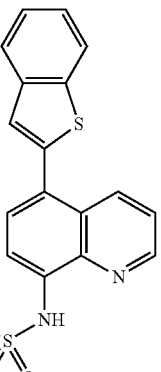 | N-(5-(benzo[b]thiophen-2-yl)quinolin-8-yl)-4-methylbenzenesulfonamide |

-continued

| No. | Structure | Name |
|---|---|---|
| 9 | 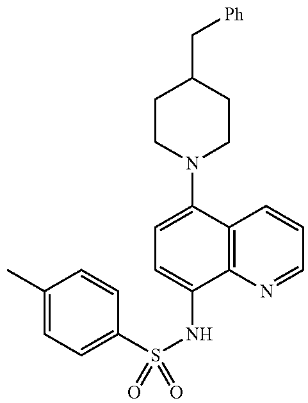 [SMILES: Cc1ccc(S(=O)(=O)Nc2ccc(N3CCC(Cc4ccccc4)CC3)c3cccnc23)cc1] | N-(5-(4-benzylpiperidin-1-yl)quinolin-8-yl)-4-methylbenzenesulfonamide |
| 10 | 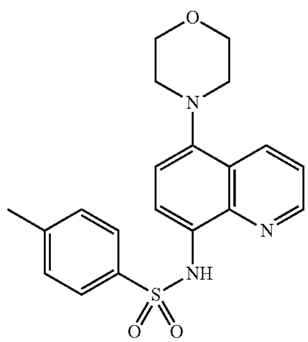 [SMILES: Cc1ccc(S(=O)(=O)Nc2ccc(N3CCOCC3)c3cccnc23)cc1] | 4-methyl-N-(5-morpholinoquinolin-8-yl)benzenesulfonamide |
| 11 | 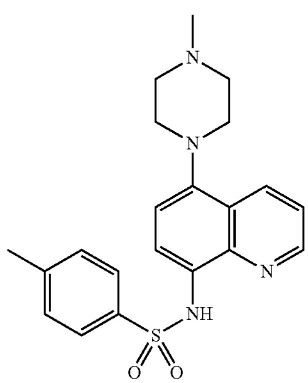 [SMILES: Cc1ccc(S(=O)(=O)Nc2ccc(N3CCN(C)CC3)c3cccnc23)cc1] | 4-methyl-N-(5-(4-methylpiperazin-1-yl)quinolin-8-yl)benzenesulfonamide |
| 12 | 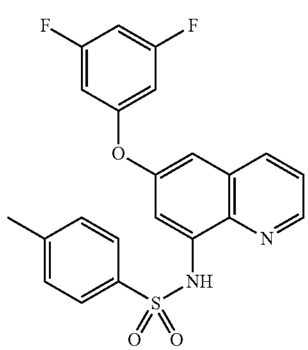 [SMILES: Cc1ccc(S(=O)(=O)Nc2cc(Oc3cc(F)cc(F)c3)cc3cccnc23)cc1] | N-(6-(3,5-difluorophenoxy)quinolin-8-yl)-4-methylbenzenesulfonamide |

| No. | Structure | Name |
|---|---|---|
| 13 | 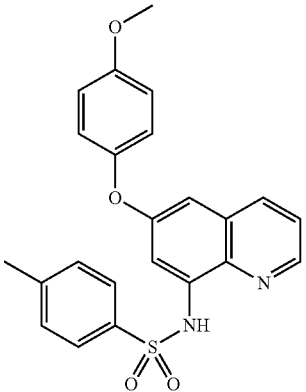 [SMILES: COc1ccc(Oc2cc(NS(=O)(=O)c3ccc(C)cc3)c3ncccc3c2)cc1] | N-(6-(4-methoxyphenoxy)quinolin-8-yl)-4-methylbenzenesulfonamide |
| 14 | 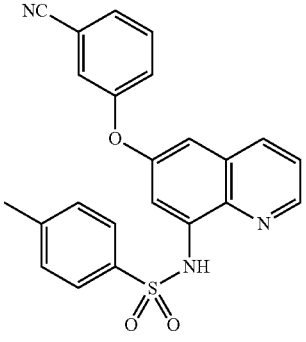 [SMILES: Cc1ccc(S(=O)(=O)Nc2cc(Oc3cccc(C#N)c3)cc3cccnc23)cc1] | N-(6-(3-cyanophenoxy)quinolin-8-yl)-4-methylbenzenesulfonamide |
| 15 | 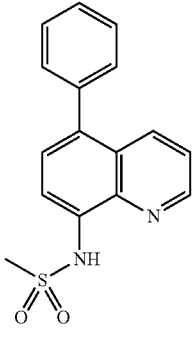 | N-(5-phenylquinolin-8-yl)methanesulfonamide |
| 16 | 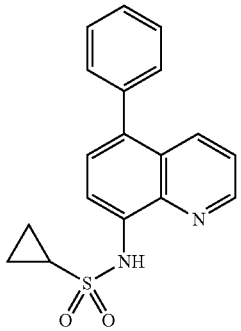 [SMILES: O=S(=O)(Nc1ccc(-c2ccccc2)c2cccnc12)C1CC1] | N-(5-phenylquinolin-8-yl)cyclopropanesulfonamide |

-continued

| No. | Structure | Name |
|---|---|---|
| 17 | 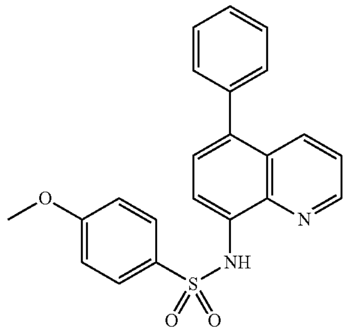 [SMILES: COc1ccc(S(=O)(=O)Nc2ccc(-c3ccccc3)c3cccnc23)cc1] | 4-methoxy-N-(5-phenylquinolin-8-yl)benzenesulfonamide |
| 18 | 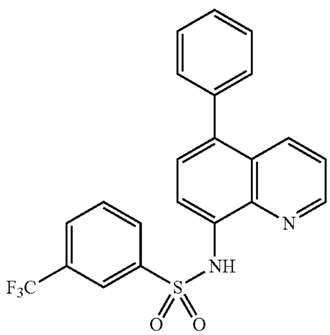 | N-(5-phenylquinolin-8-yl)-3-(trifluoromethyl)benzenesulfonamide |
| 19 | 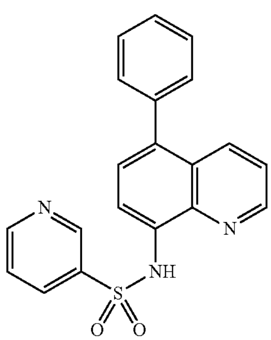 [SMILES: O=S(=O)(Nc1ccc(-c2ccccc2)c2cccnc12)c1cccnc1] | N-(5-phenylquinolin-8-yl)pyridine-3-sulfonamide |
| 20 | 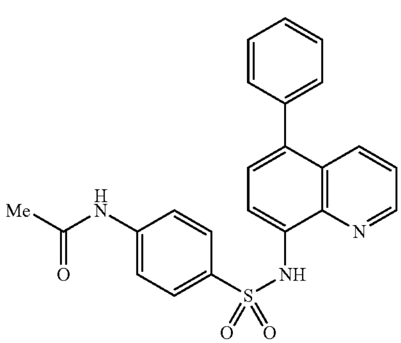 [SMILES: CC(=O)Nc1ccc(S(=O)(=O)Nc2ccc(-c3ccccc3)c3cccnc23)cc1] | N-(4-(N-(5-phenylquinolin-8-yl)sulfamoyl)phenyl)acetamide |

-continued

| No. | Structure | Name |
|---|---|---|
| 21 | 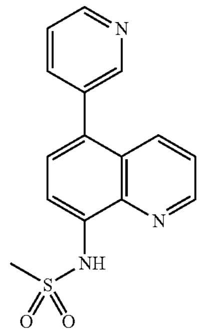 [SMILES: CS(=O)(=O)Nc1ccc(-c2cccnc2)c2cccnc12] | N-(5-(pyridin-3-yl)quinolin-8-yl)methanesulfonamide |
| 22 | 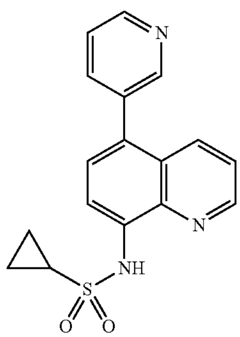 | N-(5-(pyridin-3-yl)quinolin-8-yl)cyclopropanesulfonamide |
| 23 | 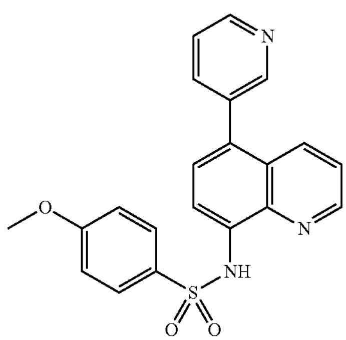 [SMILES: COc1ccc(S(=O)(=O)Nc2ccc(-c3cccnc3)c3cccnc23)cc1] | 4-methoxy-N-(5-(pyridin-4-yl)quinolin-8-yl)benzenesulfonamide |
| 24 | 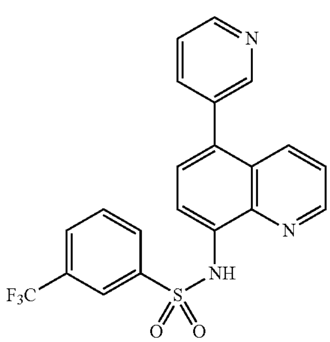 | N-(5-(pyridin-3-yl)quinolin-8-yl)-3-(trifluoromethyl)benzenesulfonamide |

-continued

| No. | Structure | Name |
|---|---|---|
| 25 | 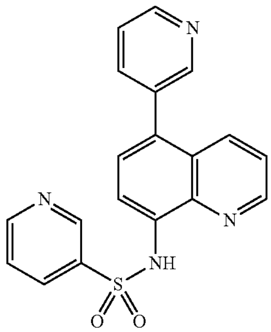 [SMILES: O=S(=O)(Nc1ccc(-c2cccnc2)c2cccnc12)c1cccnc1] | N-(5-(pyridin-3-yl)quinolin-8-yl)pyridine-3-sulfonamide |
| 26 | 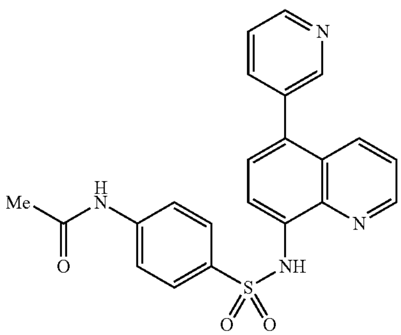 | N-(4-(N-(5-(pyridin-3-yl)quinolin-8-yl)sulfamoyl)phenyl)acetamide |
| 27 | 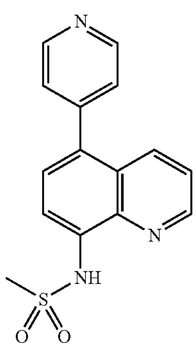 [SMILES: CS(=O)(=O)Nc1ccc(-c2ccncc2)c2cccnc12] | N-(5-(pyridin-4-yl)quinolin-8-yl)methanesulfonamide |
| 28 | 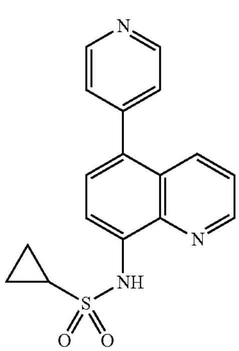 [SMILES: O=S(=O)(Nc1ccc(-c2ccncc2)c2cccnc12)C1CC1] | N-(5-(pyridin-4-yl)quinolin-8-yl)cyclopropanesulfonamide |

| No. | Structure | Name |
|---|---|---|
| 29 | 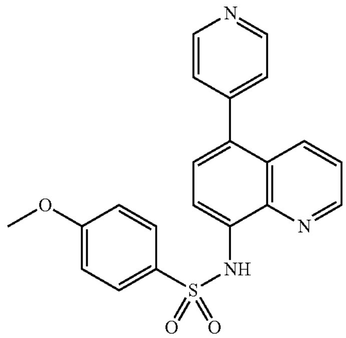 [SMILES: COc1ccc(S(=O)(=O)Nc2ccc(-c3ccncc3)c3cccnc23)cc1] | 4-methoxy-N-(5-(pyridin-3-yl)quinolin-8-yl)benzenesulfonamide |
| 30 | 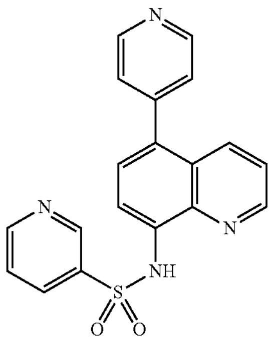 [SMILES: O=S(=O)(Nc1ccc(-c2ccncc2)c2cccnc12)c1cccnc1] | N-(5-(pyridin-4-yl)quinolin-8-yl)pyridine-3-sulfonamide |
| 31 | 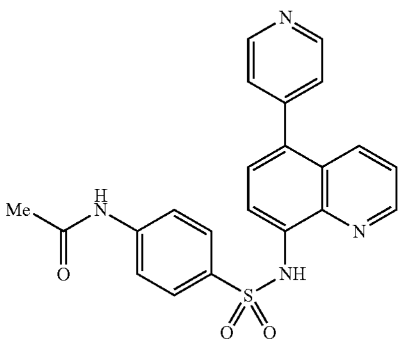 [SMILES: CC(=O)Nc1ccc(S(=O)(=O)Nc2ccc(-c3ccncc3)c3cccnc23)cc1] | N-(4-(N-(5-(pyridin-4-yl)quinolin-8-yl)sulfamoyl)phenyl)acetamide |

In some embodiments, the compound of formulae (I), (Ia-k), (II), (IIa-h), (III) and (IIIa-h) is:
4-methyl-N-(5-phenylquinolin-8-yl)benzenesulfonamide;
N-(5-(furan-2-yl)quinolin-8-yl)-4-methylbenzenesulfonamide;
4-methyl-N-(5-(pyridin-3-yl)quinolin-8-yl)benzenesulfonamide;
4-methyl-N-(5-(thiophen-3-yl)quinolin-8-yl)benzenesulfonamide;
N-(5-(benzo[b]thiophen-2-yl)quinolin-8-yl)-4-methylbenzenesulfonamide;
N-(5-(4-benzylpiperidin-1-yl)quinolin-8-yl)-4-methylbenzenesulfonamide;
4-methyl-N-(5-morpholinoquinolin-8-yl)benzenesulfonamide;
4-methyl-N-(5-(4-methylpiperazin-1-yl)quinolin-8-yl)benzenesulfonamide;
N-(6-(3,5-difluorophenoxy)quinolin-8-yl)-4-methylbenzenesulfonamide;
N-(6-(4-methoxyphenoxy)quinolin-8-yl)-4-methylbenzenesulfonamide;
N-(6-(3-cyanophenoxy)quinolin-8-yl)-4-methylbenzenesulfonamide;
N-(5-phenylquinolin-8-yl)methanesulfonamide;
N-(5-phenylquinolin-8-yl)cyclopropanesulfonamide;
4-methoxy-N-(5-phenylquinolin-8-yl)benzenesulfonamide;
N-(5-phenylquinolin-8-yl)-3-(trifluoromethyl)benzenesulfonamide;
N-(5-phenylquinolin-8-yl)pyridine-3-sulfonamide;
N-(4-(N-(5-phenylquinolin-8-yl)sulfamoyl)phenyl)acetamide;
N-(5-(pyridin-3-yl)quinolin-8-yl)methanesulfonamide;
N-(5-(pyridin-3-yl)quinolin-8-yl)cyclopropanesulfonamide;
4-methoxy-N-(5-(pyridin-4-yl)quinolin-8-yl)benzenesulfonamide;
N-(5-(pyridin-3-yl)quinolin-8-yl)-3-(trifluoromethyl)benzenesulfonamide;
N-(5-(pyridin-3-yl)quinolin-8-yl)pyridine-3-sulfonamide;
N-(4-(N-(5-(pyridin-3-yl)quinolin-8-yl)sulfamoyl)phenyl)acetamide;
N-(5-(pyridin-4-yl)quinolin-8-yl)methanesulfonamide;
N-(5-(pyridin-4-yl)quinolin-8-yl)cyclopropanesulfonamide;

4-methoxy-N-(5-(pyridin-3-yl)quinolin-8-yl)benzenesulfonamide;

N-(5-(pyridin-4-yl)quinolin-8-yl)pyridine-3-sulfonamide; or

N-(4-(N-(5-(pyridin-4-yl)quinolin-8-yl)sulfamoyl)phenyl)acetamide.

In embodiment IV$_1$, the invention comprises compounds having structural formula (IV):

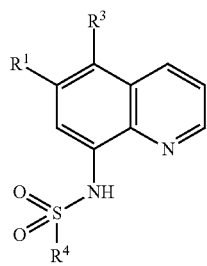

(IV)

and pharmaceutically acceptable salts, prodrugs and N-oxides thereof, and solvates and hydrates thereof, wherein $R^1$ is -hydrogen or —O—(C$_0$-C$_6$ alkyl)-Ar, $R^3$ is -hydrogen, —(C$_0$-C$_6$ alkyl)-Ar or —(C$_0$-C$_6$ alkyl)-Het; and $R^4$ is —(C$_0$-C$_6$ alkyl)-Ar or —(C$_0$-C$_6$ alkyl)-Het;

wherein each Ar (aryl) and Het (heteroaryl) is optionally substituted.

In embodiment IV$_2$, the compounds are of embodiment IV$_1$, provided that:

(1) at least one of $R^1$ and $R^3$ is not hydrogen; or (2) neither $R^1$ nor $R^3$ is hydrogen.

In embodiment IV$_3$, the compounds of the invention are of one of formulae (IVa)-(IVx), wherein $R^1$, $R^3$, and $R^4$ are as defined in embodiment IV$_1$ or IV$_2$, and $R^a$, $R^b$, $R^c$, $R^e$ n, m, y and w are as defined in any embodiment hereinabove:

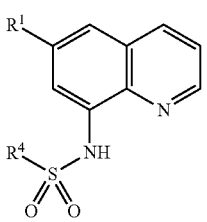

(IVa)

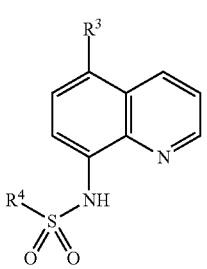

(IVb)

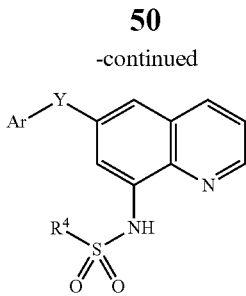

(IVc)

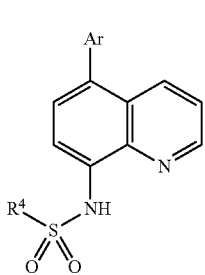

(IVd)

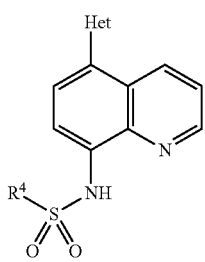

(IVe)

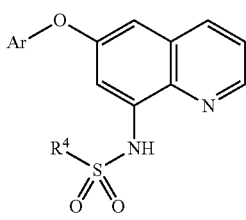

(IVf)

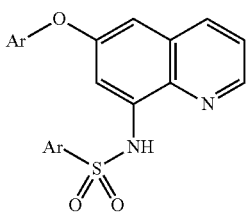

(IVg)

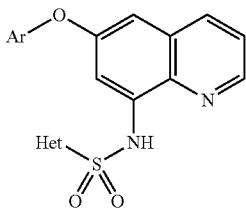

(IVh)

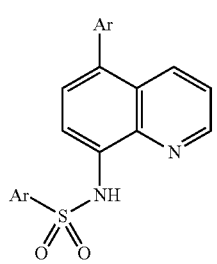 (IVi)
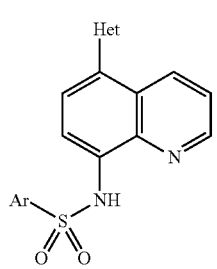 (IVj)
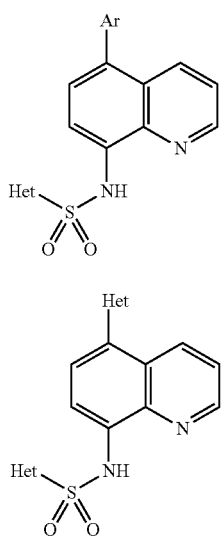 (IVk)
(IVl)
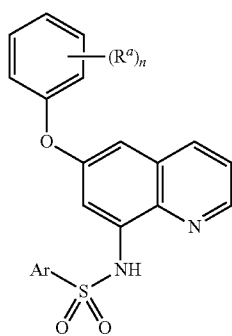 (IVm)
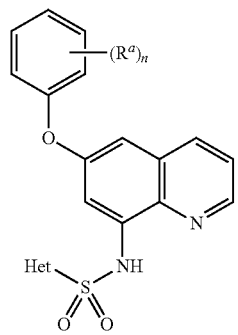 (IVn)
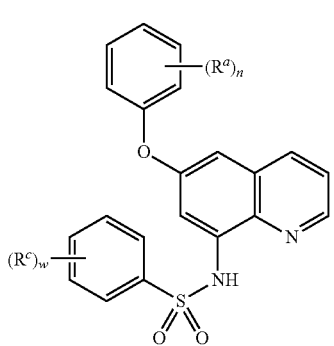 (IVo)
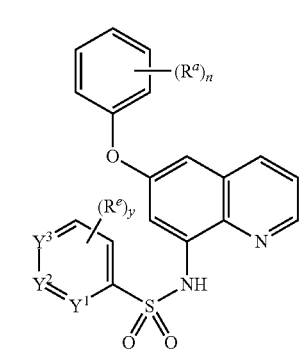 (IVp)
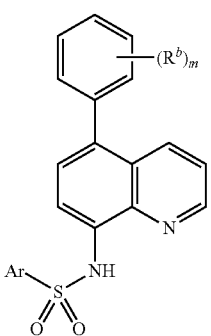 (IVq)

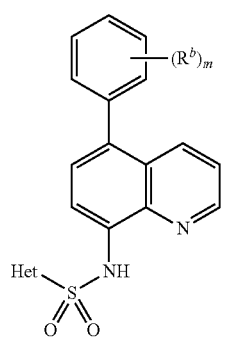 (IVr)
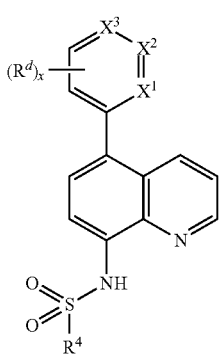 (IVu)
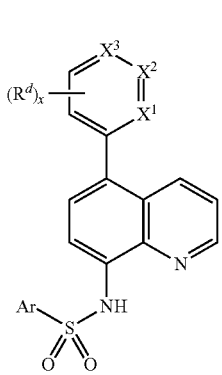 (IVv)
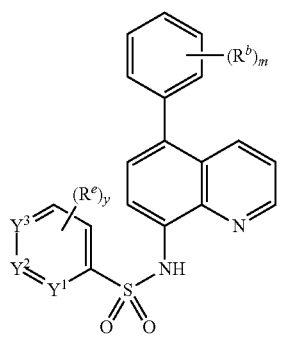 (IVs)
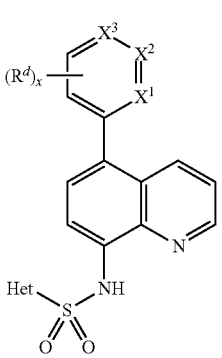 (IVw)
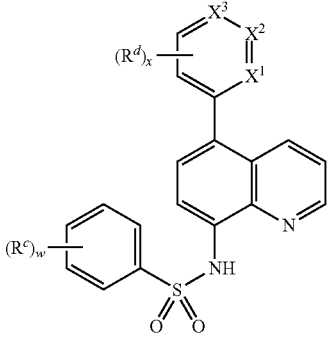 (IVx)
(IVt)

In some embodiments, the compound of formula (IV) is:

| No. | Structure | Name |
|---|---|---|
| 4 | 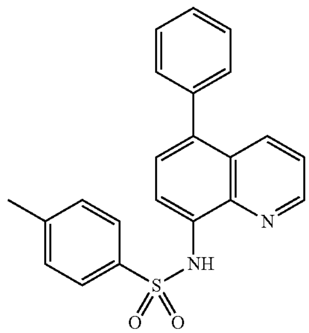 [SMILES: Cc1ccc(S(=O)(=O)Nc2ccc(-c3ccccc3)c3cccnc23)cc1] | 4-methyl-N-(5-phenylquinolin-8-yl)benzenesulfonamide |
| 5 | 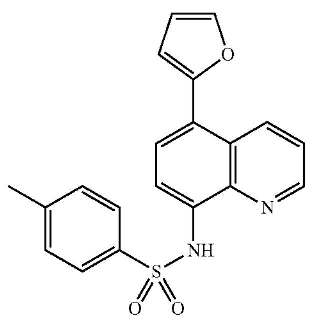 [SMILES: Cc1ccc(S(=O)(=O)Nc2ccc(-c3ccco3)c3cccnc23)cc1] | N-(5-(furan-2-yl)quinolin-8-yl)-4-methylbenzenesulfonamide |
| 6 | 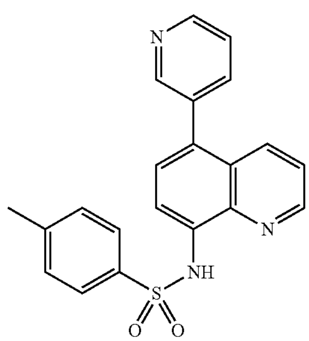 [SMILES: Cc1ccc(S(=O)(=O)Nc2ccc(-c3cccnc3)c3cccnc23)cc1] | 4-methyl-N-(5-(pyridin-3-yl)quinolin-8-yl)benzenesulfonamide |
| 7 | 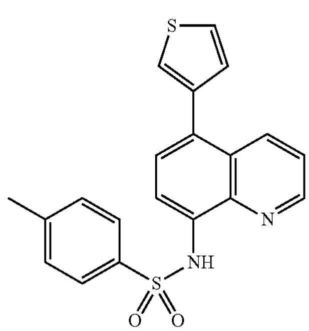 [SMILES: Cc1ccc(S(=O)(=O)Nc2ccc(-c3ccsc3)c3cccnc23)cc1] | 4-methyl-N-(5-(thiophen-3-yl)quinolin-8-yl)benzenesulfonamide |

-continued

| No. | Structure | Name |
| --- | --- | --- |
| 8 | 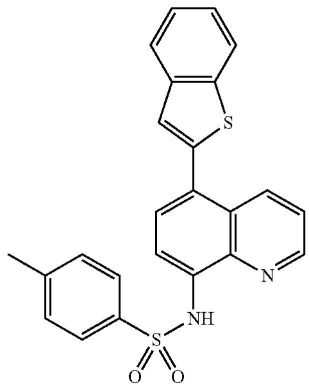 [SMILES: Cc1ccc(S(=O)(=O)Nc2ccc(-c3cc4ccccc4s3)c3cccnc23)cc1] | N-(5-(benzo[b]thiophen-2-yl)quinolin-8-yl)-4-methylbenzenesulfonamide |
| 12 | 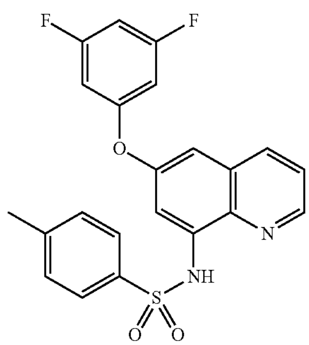 [SMILES: Cc1ccc(S(=O)(=O)Nc2cc(Oc3cc(F)cc(F)c3)cc3cccnc23)cc1] | N-(6-(3,5-difluorophenoxy)quinolin-8-yl)-4-methylbenzenesulfonamide |
| 13 | 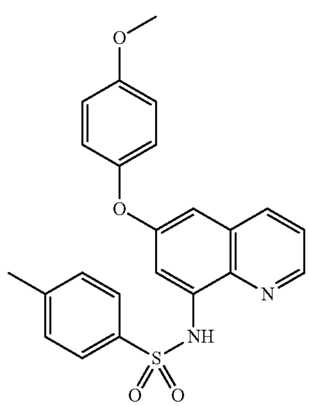 [SMILES: COc1ccc(Oc2cc(NS(=O)(=O)c3ccc(C)cc3)c3ncccc3c2)cc1] | N-(6-(4-methoxyphenoxy)quinolin-8-yl)-4-methylbenzenesulfonamide |
| 14 | 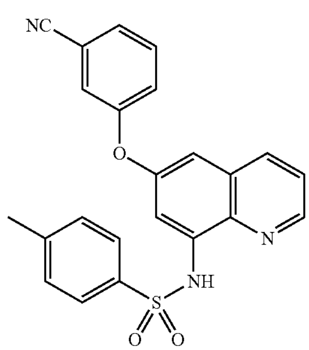 [SMILES: Cc1ccc(S(=O)(=O)Nc2cc(Oc3cccc(C#N)c3)cc3cccnc23)cc1] | N-(6-(3-cyanophenoxy)quinolin-8-yl)-4-methylbenzenesulfonamide |

-continued

| No. | Structure | Name |
|---|---|---|
| 15 | 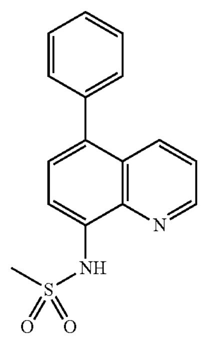 [SMILES: CS(=O)(=O)Nc1ccc(-c2ccccc2)c2cccnc12] | N-(5-phenylquinolin-8-yl)methanesulfonamide |
| 19 | 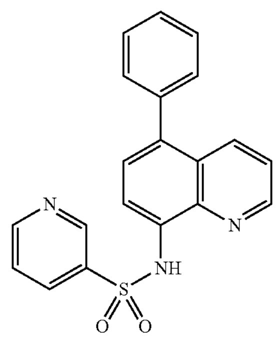 [SMILES: O=S(=O)(Nc1ccc(-c2ccccc2)c2cccnc12)c1cccnc1] | N-(5-phenylquinolin-8-yl)pyridine-3-sulfonamide |
| 23 | 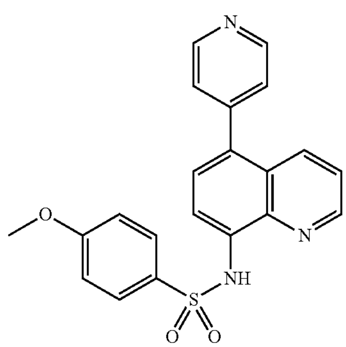 [SMILES: COc1ccc(S(=O)(=O)Nc2ccc(-c3ccncc3)c3cccnc23)cc1] | 4-methoxy-N-(5-(pyridin-4-yl)quinolin-8-yl)benzenesulfonamide |
| 24 | 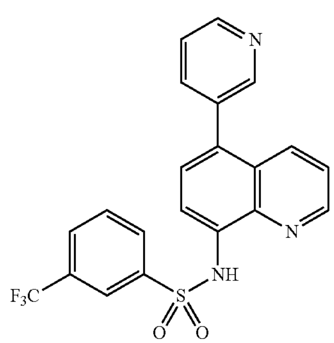 [SMILES: O=S(=O)(Nc1ccc(-c2cccnc2)c2cccnc12)c1cccc(C(F)(F)F)c1] | N-(5-(pyridin-3-yl)quinolin-8-yl)-3-(trifluoromethyl)benzenesulfonamide |

| No. | Structure | Name |
|---|---|---|
| 25 | 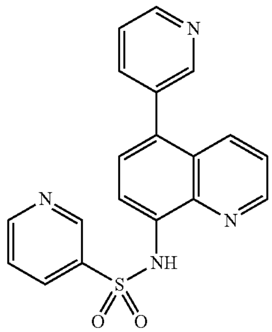 [SMILES: O=S(=O)(Nc1ccc(-c2cccnc2)c2cccnc12)c1cccnc1] | N-(5-(pyridin-3-yl)quinolin-8-yl)pyridine-3-sulfonamide |
| 29 | 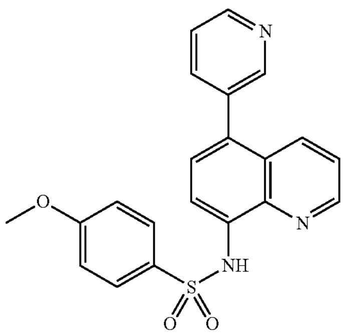 [SMILES: COc1ccc(S(=O)(=O)Nc2ccc(-c3cccnc3)c3cccnc23)cc1] | 4-methoxy-N-(5-(pyridin-3-yl)quinolin-8-yl)benzenesulfonamide |
| 30 | 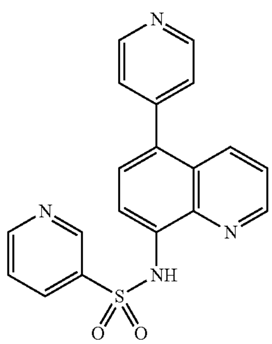 [SMILES: O=S(=O)(Nc1ccc(-c2ccncc2)c2cccnc12)c1cccnc1] | N-(5-(pyridin-4-yl)quinolin-8-yl)pyridine-3-sulfonamide |

In another aspect, the present invention comprises pharmaceutical compositions comprising a compound according to any one of the preceding aspects of the invention or any embodiment thereof, together with a pharmaceutically acceptable excipient, diluent, or carrier.

In another aspect, the invention comprises the use of a compound described by any one of the preceding aspects of the invention or any embodiment thereof, for the preparation of a medicament for the treatment of medical diseases or conditions that benefit from the inhibition of Cks1-Skp2 PPI. Medical conditions contemplated in this aspect include all diseases and conditions described herein.

In another aspect, the invention comprises methods for treating a disease or condition mediated by or involving Cks1-Skp2 PPI in a subject in need thereof, comprising administering to the subject an effective Cks1-Skp2 PPI inhibiting amount of a compound or a pharmaceutical composition according to any of the preceding aspects of the invention or any embodiment thereof. In some embodiments, the subject is an animal, particularly, a mammal. In some embodiments, the subject is a human.

In another aspect, the invention comprises methods of inhibiting Cks1-Skp2 PPI in a cell, the method comprising contacting the cell with an effective Cks1-Skp2 PPI inhibiting amount of a compound or a pharmaceutical composition according to any of the preceding aspects of the invention or any embodiment thereof. In some embodiments the cell is an animal cell, such as a mammalian cell. In some embodiments, the cells are human cells.

In another aspect, the invention comprises methods for inhibiting protein ubiquitination in subjects in need thereof, the method comprising administering an effective ubiquitination-inhibiting amount of a compound preceding aspects of the invention or any embodiment thereof to the subject. In some embodiments, the subject is an animal, particularly, a mammal. In some embodiments, the subject is a human.

In another aspect, the invention comprises methods for treating a disease or condition mediated by or involving protein ubiquitination in a subject in need thereof, comprising administering an effective ubiquitination-inhibiting amount of a compound or a pharmaceutical composition according to any of the preceding aspects of the invention or any embodiment thereof.

In another aspect, the invention comprises methods of inhibiting protein ubiquitination in a cell, comprising contacting the cell in which inhibition of ubiquitination is desired with an effective ubiquitination-inhibiting amount of a compound or a pharmaceutical composition according to any of the preceding aspects of the invention or any embodiment thereof. In some embodiments the cell is an animal cell, such as a mammalian cell. In some embodiments, the cells are human cells.

In another aspect, the invention comprises methods for treating a disease or condition mediated by increasing p27 levels in a subject in need thereof, comprising administering an effective p27-increasing amount of a compound or a pharmaceutical composition according to any of the preceding aspects of the invention or any embodiment thereof. In some embodiments, the subject is an animal, particularly, a mammal. In some embodiments, the subject is a human.

In another aspect, the invention comprises methods of increasing p27 levels in a cell, comprising contacting the cell in which increased levels of p27 is desired with an effective p27-increasing amount of a compound or a pharmaceutical composition according to any of the preceding aspects of the invention or any embodiment thereof. In some embodiments the cell is an animal cell, such as a mammalian cell. In some embodiments, the cells are human cells.

In an embodiment of any of the above aspects, the condition or disease involves a process selected from the group consisting of inflammation, adaptive immunity, innate immunity, bone metabolism, LPS-induced angiogenesis, osteoporosis, osteopinneal diseases, lymph node development, mammary gland development, skin development, and central nervous system development.

In an embodiment of any of the above aspects, the disease or medical condition is cancer.

In some embodiments, the cancer is colon, pancreas, breast, prostate, lung, brain, ovary, cervix, testes, renal, head, or neck cancer, or lymphoma, leukemia, or melanoma.

Definitions

Terms used herein may be preceded and/or followed by a single dash, "—", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, arylalkyl, arylalkyl-, and -alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as $(A)_a$-B—, wherein a is 0 or 1. In such instances, when a is 0 the moiety is B— and when a is 1 the moiety is A-B—.

As used herein, the term "alkyl" includes alkyl, alkenyl and alkynyl groups of a designed number of carbon atoms, such as 1 to 12 carbons (i.e., inclusive of 1 and 12), 1 to 6 carbons, 1 to 3 carbons, or 1, 2, 3, 4, 5, 6, 7, 8, 9, 10, 11, or 12. The term "$C_m$-$C_n$ alkyl" means an alkyl group having from m to n carbon atoms (i.e., inclusive of m and n). The term "$C_m$-$C_n$ alkyl" means an alkyl group having from m to n carbon atoms. For example, "$C_1$-$C_6$ alkyl" is an alkyl group having from one to six carbon atoms. Alkyl and alkyl groups may be straight or branched and depending on context, may be a monovalent radical or a divalent radical (i.e., an alkylene group). In the case of an alkyl or alkyl group having zero carbon atoms (i.e., "$C_0$ alkyl"), the group is simply a single covalent bond if it is a divalent radical or is a hydrogen atom if it is a monovalent radical. For example, the moiety "—($C_0$-$C_6$ alkyl)-Ar" signifies connection of an optionally substituted aryl through a single bond or an alkylene bridge having from 1 to 6 carbons. Examples of "alkyl" include, for example, methyl, ethyl, propyl, isopropyl, butyl, iso-, sec- and tert-butyl, pentyl, hexyl, heptyl, 3-ethylbutyl, 3-hexenyl and propargyl. If the number of carbon atoms is not specified, the subject "alkyl" or "alkyl" moiety has from 1 to 12 carbons.

The term "haloalkyl" is an alkyl group substituted with one or more halogen atoms, e.g. F, Cl, Br and I. A more specific term, e.g., "fluoroalkyl" is an alkyl group substituted with one or more fluorine atoms. Examples of "fluoroalkyl" include fluoromethyl, difluoromethyl, trifluoromethyl, pentafluoroethyl, hexafluoroisopropyl and the like. In certain embodiments of the compounds disclosed herein, each haloalkyl is a fluoroalkyl.

The term "aryl" represents an aromatic ring system having a single ring (e.g., phenyl) which is optionally fused to other aromatic hydrocarbon rings or non-aromatic hydrocarbon rings. "Aryl" includes ring systems having multiple condensed rings and in which at least one is carbocyclic and aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. In certain examples, aryl groups include those having a first carbocyclic, aromatic ring fused to an aromatic or aliphatic heterocycle, for example, 2,3-dihydrobenzofuranyl. The aryl groups herein are unsubstituted or, when specified as "optionally substituted", can unless stated otherwise be substituted in one or more substitutable positions with various groups, as described below.

The term "heteroaryl" refers to an aromatic ring system containing at least one heteroatom selected from nitrogen, oxygen and sulfur in an aromatic ring. The heteroaryl may be fused to one or more cycloalkyl or heterocycloalkyl rings. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as described below.

The term "heterocycloalkyl" refers to a non-aromatic ring or ring system containing at least one heteroatom that is preferably selected from nitrogen, oxygen and sulfur, wherein said heteroatom is in a non-aromatic ring. The heterocycloalkyl may be saturated (i.e., a heterocycloalkyl) or partially unsaturated (i.e., a heterocycloalkenyl). Heterocycloalkyl includes monocyclic groups as well as bicyclic and polycyclic ring systems, including bridged and fused systems. The heterocycloalkyl ring is optionally fused to other heterocycloalkyl rings and/or non-aromatic hydrocarbon rings and/or phenyl rings. In certain embodiments, the heterocycloalkyl groups have from 3 to 7 members in a single ring. In other embodiments, heterocycloalkyl groups have 5 or 6 members in a single ring. In some embodiments, the heterocycloalkyl groups have 3, 4, 5, 6 or 7 members in a single ring. Examples of heterocycloalkyl groups include, for example, azabicyclo[2.2.2]octyl (in each case also "quinuclidinyl" or a quinuclidine derivative), azabicyclo[3.2.1] octyl, 2,5-diazabicyclo[2.2.1]heptyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butryolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as described below.

The term "cycloalkyl" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (e.g., bridged systems) to other cycloalkyl rings. Certain examples of cycloalkyl groups present in the disclosed compounds have from 3 to 7 members in a single ring, such as having 5 or 6 members in a single ring. In some embodiments, the cycloalkyl groups have 3, 4, 5, 6 or 7 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups.

The term "ring system" encompasses monocycles, as well as fused and/or bridged polycycles.

The term "oxa" means a divalent oxygen radical in a chain, sometimes designated as —O—.

The term "oxo" means a doubly bonded oxygen, sometimes designated as =O or for example in describing a carbonyl "C(O)" may be used to show an oxo substituted carbon.

The term "electron withdrawing group" means a group that withdraws electron density from the structure to which it is attached than would a similarly-attached hydrogen atom. For example, electron withdrawing groups can be selected from the group consisting of halo (e.g., fluoro, chloro, bromo, and iodo), cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), $NO_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group.

The term "substituted," when used to modify a specified group or radical, means that one or more hydrogen atoms of the specified group or radical are each, independently of one another, replaced with the same or different substituent groups as defined below, unless specified otherwise.

Substituent groups for substituting for hydrogens on saturated carbon atoms in the specified group or radical are, unless otherwise specified, —$R^{60}$, halo, —$O^-M^+$, =O, —$OR^{70}$, —$SR^{70}$, —$S^-M^+$, =S, —$NR^{80}R^{80}$, =$NR^{70}$, =N—$OR^{70}$, trihalomethyl, —$CF_3$, —CN, —OCN, —SCN, —NO, —$NO_2$, =$N_2$, —$N_3$, —$SO_2R^{70}$, —$SO_2O^-M^+$, —$SO_2OR^{70}$, —$OSO_2R^{70}$, —$OSO_2O^-M^-$, —$OSO_2OR^{70}$, —P(O)($O^-$)$_2$($M^+$)$_2$, —P(O)($OR^{70}$)$O^-M^+$, —P(O)($OR^{70}$)$_2$, —C(O)$R^{70}$, —C(S)$R^{70}$, —C($NR^{70}$)$R^{70}$, —C(O)$O^-M^+$, —C(O)$OR^{70}$, —C(S)$OR^{70}$, —C(O)$NR^{80}R^{80}$, —C($NR^{70}$)$NR^{80}R^{80}$, —OC(O)$R^{70}$, —OC(S)$R^{70}$, —OC(O)$O^-M^+$, —OC(O)$OR^{70}$, —OC(S)$OR^{70}$, —$NR^{70}$C(O)$R^{70}$, —$NR^{70}$C(S)$R^{70}$, —$NR^{70}CO_2^-M^+$, —$NR^{70}CO_2R^{70}$, —$NR^{70}$C(S)$OR^{70}$, —$NR^{70}$C(O)$NR^{80}R^{80}$, —$NR^{70}$C($NR^{70}$)$R^{70}$ and —NR$^{70}$C(NR$^{70}$)NR$^{80}$R$^{80}$. Each R$^{60}$ is independently selected from the group consisting of alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —OR$^{71}$, —SR$^{71}$, —S$^-$M$^+$, =S, —NR$^{81}$R$^{81}$, =NR$^{71}$, =N—OR$^{71}$, trihalomethyl, —CF$_3$, —CN, —OCN, —SCN, —NO, —NO$_2$, =N$_2$, —N$_3$, —SO$_2$R$^{71}$, —SO$_2$O$^-$M$^+$, —SO$_2$OR$^{71}$, —OSO$_2$R$^{71}$, —OSO$_2$O$^-$M, —OSO$_2$OR$^{71}$, —P(O)(O$^-$)$_2$(M$^+$)$_2$, —P(O)(OR$^{71}$)O$^-$M$^+$, —P(O)(OR$^{71}$)$_2$, —C(O)R$^{71}$, —C(S)R$^{71}$, —C(NR$^{71}$)R$^{71}$, —C(O)O$^-$M$^+$, —C(O)OR$^{71}$, —C(S)OR$^{71}$, —C(O)NR$^{81}$R$^{81}$, —C(NR$^{71}$)NR$^{81}$R$^{81}$, —OC(O)R$^{71}$, —OC(S)R$^{71}$, —OC(O)O$^-$M$^+$, —OC(O)OR$^{71}$, —OC(S)OR$^{71}$, —NR$^{71}$C(O)R$^{71}$, —NR$^{71}$C(S)R$^{71}$, —NR$^{71}$CO$_2$$^-$M$^+$, —NR$^{71}$CO$_2$R$^{71}$, —NR$^{71}$C(S)OR$^{71}$, —NR$^{71}$C(O)NR$^{81}$R$^{81}$, —NR$^{71}$C(NR$^{71}$)R$^{71}$ and —NR$^{71}$C(NR$^{71}$)NR$^{81}$R$^{81}$. Each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each R$^{71}$ is independently hydrogen or R$^{61}$, in which R$^{61}$ is alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —OR$^{72}$, —SR$^{72}$, —S$^-$M$^+$, =S, —NR$^{82}$R$^{82}$, =NR$^{72}$, =N—OR$^{72}$, trihalomethyl, —CF$_3$, —CN, —OCN, —SCN, —NO, —NO$_2$, =N$_2$, —N$_3$, —SO$_2$R$^{71}$, —SO$_2$O$^-$M$^+$, —SO$_2$OR$^{72}$, —OSO$_2$R$^{72}$, —OSO$_2$O$^-$M$^-$, —OSO$_2$OR$^{72}$, —P(O)(O$^-$)$_2$(M$^+$)$_2$, —P(O)(OR$^{72}$)O$^-$M$^+$, —P(O)(OR$^{72}$)$_2$, —C(O)R$^{72}$, —C(S)R$^{72}$, —C(NR$^{72}$)R$^{72}$, —C(O)O$^-$M$^+$, —C(O)OR$^{72}$, —C(S)OR$^{72}$, —C(O)NR$^{82}$R$^{82}$, —C(NR$^{72}$)NR$^{82}$R$^{82}$, —OC(O)R$^{72}$, —OC(S)R$^{72}$, —OC(O)O$^-$M$^+$, —OC(O)OR$^{72}$, —OC(S)OR$^{72}$, —NR$^{72}$C(O)R$^{72}$, —NR$^{72}$C(S)R$^{72}$, —NR$^{72}$CO$_2$$^-$M$^+$, —NR$^{72}$CO$_2$R$^{72}$, —NR$^{72}$C(S)OR$^{72}$, —NR$^{72}$C(O)NR$^{82}$R$^{82}$, —NR$^{72}$C(NR$^{72}$)R$^{72}$ and —NR$^{72}$C(NR$^{72}$)NR$^{82}$R$^{82}$; and each R$^{81}$ is independently R$^{71}$ or alternatively, two R$^{81}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution. Each R$^{72}$ is independently hydrogen, (C$_1$-C$_6$ alkyl) or (C$_1$-C$_6$ fluoroalkyl); each R$^{82}$ is independently R$^{72}$ or alternatively, two R$^{82}$s, taken together with the nitrogen atom to which they are bonded, form a 5-, 6- or 7-membered heterocycloalkyl which may optionally include 1, 2, 3 or 4 of the same or different additional heteroatoms selected from the group consisting of O, N and S, of which N may have —H or C$_1$-C$_3$ alkyl substitution. Each M may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means e.g. that one of the counter ions for such divalent alkali earth ions can be an ionized form of a presently disclosed compound and the other a typical counter ion such as chloride, or two ionized presently disclosed molecules can serve as counter ions for such divalent alkali earth ions, or a doubly ionized compound can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4-methyl-piperazin-1-yl and N-morpholinyl.

Substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$$^-$M$^+$, —SO$_3$R$^{70}$, —OSO$_2$R$^{70}$, —OSO$_3$M$^+$, —OSO$_3$R$^{70}$, —PO$_3$$^{-2}$(M$^+$)$_2$, —P(O)(OR$^{70}$)OM$^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

Substituent groups for hydrogens on nitrogen atoms in "substituted" heteroalkyl and heterocycloalkyl groups are, unless otherwise specified, —R$^{60}$, —O$^-$M$^+$, —OR$^{70}$, —SR$^{70}$, —S$^-$M$^-$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)—R$^{70}$, —OC(S)R$^{70}$, —OC(S)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In certain embodiments of the compounds disclosed herein, a group that is substituted has 1, 2, 3, or 4 substituents, 1, 2, or 3 substituents, 1 or 2 substituents, or 1 substituent.

In certain preferred embodiments, substituent groups on "substituted" alkyl, cycloalkyl, heterocycloalkyl, aryl and heteroaryl groups are -halo, —OH, —O—(C$_1$-C$_4$ alkyl), —O—(C$_1$-C$_4$ haloalkyl), —N(C$_0$-C$_4$ alkyl)(C$_0$-C$_4$ alkyl), —SH, —S(O)$_{0-2}$—(C$_1$-C$_4$ alkyl), —(C$_1$-C$_4$ alkyl), —(C$_1$-C$_4$ haloalkyl), —C(O)—(C$_0$-C$_4$ alkyl), —C(O)N(C$_0$-C$_4$ alkyl)(C$_0$-C$_4$ alkyl), —N(C$_0$-C$_4$ alkyl)C(O)(C$_0$-C$_4$ alkyl)(C$_0$-C$_4$ alkyl), —C(O)O—(C$_0$-C$_4$ alkyl), —OC(O)—(C$_0$-C$_4$ alkyl), S(O)$_2$—O(C$_0$-C$_4$ alkyl), and —NO$_2$, in which no alkyl is further substituted.

The compounds disclosed herein can also be provided as pharmaceutically acceptable salts. The term "pharmaceutically acceptable salts" or "a pharmaceutically acceptable salt thereof" refer to salts prepared from pharmaceutically acceptable non-toxic acids or bases including inorganic acids and bases and organic acids and bases. If the compound is basic, salts may be prepared from pharmaceutically acceptable non-toxic acids. Such salts may be, for example, acid addition salts of at least one of the following acids: benzenesulfonic acid, citric acid, α-glucoheptonic acid, D-gluconic acid, glycolic acid, lactic acid, malic acid, malonic acid, mandelic acid, phosphoric acid, propanoic acid, succinic acid, sulfuric acid, tartaric acid (d, l, or dl), tosic acid (toluenesulfonic acid), valeric acid, palmitic acid, pamoic acid, sebacic acid, stearic acid, lauric acid, acetic acid, adipic acid, carbonic acid, 4-chlorobenzenesulfonic acid, ethanedisulfonic acid, ethylsuccinic acid, fumaric acid, galactaric acid (mucic acid), D-glucuronic acid, 2-oxoglutaric acid, glycerophosphoric acid, hippuric acid, isethionic acid (ethanolsulfonic acid), lactobionic acid, maleic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, hydriodic acid, hydrobromic acid, hydrochloric acid, methanesulfonic acid, nicotinic acid, nitric acid, orotic acid, oxalic acid, picric acid, L-pyroglutamic acid, saccharine, salicylic acid, gentisic acid, and/or 4-acetamidobenzoic acid.

The compounds described herein can also be provided in prodrug form. "Prodrug" refers to a derivative of an active compound (drug) that undergoes a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. A wide variety of progroups, as well as the resultant promoieties, suitable for masking functional groups in the active drugs to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Specific examples of suitable progroups and their respective promoieties will be apparent to those of skill in the art.

The compounds disclosed herein can also be provided as N-oxides.

The presently disclosed compounds, salts, prodrugs and N-oxides can be provided, for example, in solvate or hydrate form.

One of ordinary skill in the art of medicinal chemistry also will appreciate that the disclosed structures are intended to include isotopically enriched forms of the present compounds. As used herein "isotopes" includes those atoms having the same atomic number but different mass numbers. As is known to those of skill in the art, certain atoms, such as hydrogen occur in different isotopic forms. For example, hydrogen includes three isotopic forms, protium, deuterium and tritium. As will be apparent to those of skill in the art upon consideration of the present compounds, certain compounds can be enriched at a given position with a particular isotope of the atom at that position. For example, compounds having a fluorine atom, may be synthesized in a form enriched in the radioactive fluorine isotope $^{18}F$. Similarly, compounds may be enriched in the heavy isotopes of hydrogen: deuterium and tritium; and similarly can be enriched in a radioactive isotope of carbon, such as $^{13}C$. Such isotopic variant compounds undergo different metabolic pathways and can be useful, for example, in studying the ubiquitination pathway and its role in disease.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" an enzyme with a compound includes the administration of a compound described herein to an individual or patient, such as a human, as well as, for example, introducing a compound into a sample containing a cellular or purified preparation containing the enzyme.

As used herein, the terms "individual," "patient," or "subject" are used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, condition, for disorder, such as, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or (ii) eliciting the referenced biological effect (e.g., modulation or inhibition of Cks1-Skp2 PPI, inhibition of ubiqutination, or increase in p27 levels).

Manifestation of amelioration of a disease condition by inhibiting ubiquitination and/or Cks1-Skp2 PPI may require the concomitant or sequential administration of additional therapeutic agents, such as antineoplastic agents in the case of cancer, or antiretroviral agents in the case of viral diseases. For example, administration of ubiquitination and/or Cks1-Skp2 PPI inhibitors for the treatment of cancer does not always produce a direct antitumor effect when used as a single agent. However, when combined with chemotherapeutic drugs (antineoplastic) the antitumor effect observed is higher than the sum of effects of each agent alone.

As used herein, the terms "catalytic pocket", "catalytic site", "active site" collectively and indistinctly refer to a region of the enzyme that contains amino acid residues responsible for the substrate binding (charge, hydrophobicity, steric hindrance) and catalytic amino acid residues which act as proton donors or acceptors or are responsible for binding a cofactor and participate in the catalysis of a chemical reaction.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Methods of Use

The compounds and pharmaceutical compositions described herein can modulate activity of the Cks1-Skp2 PPI. The term "modulate" is meant to refer to an ability to decrease activity of an enzyme or receptor, or disrupt binding. Accordingly, compounds described herein can be used in methods of modulating Cks1-Skp2 PPI by contacting the proteins with any one or more of the compounds or compositions described herein. In some embodiments, the compounds described herein can act as inhibitors of ubiquitination. In further embodiments, the compounds described herein can be used to modulate activity of the Cks1-Skp2 PPI in a cell or in an individual in need of modulation of the interaction by administering a modulating (e.g., inhibiting) amount of a compound described herein.

Further provided are methods of inhibiting the degradation of tumor suppressors. In some embodiments methods of altering (e.g., decreasing) the degradation of tumor suppressors comprise administering an effective amount of a compound or pharmaceutical composition provided herein. In some embodiments, an effective amount of a compound or pharmaceutical composition provided herein and a tumor suppressor are administered simultaneously. In other embodiments, an effective amount of a compound or pharmaceutical composition provided herein and a tumor suppressor are administered sequentially. In other embodiments, the tumor suppressor is p27.

For example, a subject undergoing or having completed a course of chemotherapy and/or radiation therapy for the treatment of a disease state, such as a cancer, can benefit from administering to the patient a therapeutically effective amount of a compound or composition recited herein for inhibiting degradation of a tumor suppressor.

Pharmaceutical Formulations and Dosage Forms

The compounds of structural formulae (I)-(IV) can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like.

Pharmaceutical compositions can be made using the presently disclosed compounds. For example, in one embodiment, a pharmaceutical composition includes a pharmaceutically acceptable carrier, diluent or excipient, and compound as described above with reference to structural formulae (I)-(IV).

In the pharmaceutical compositions disclosed herein, one or more compounds of structural formulae (I)-(IV) may be present in association with one or more pharmaceutically acceptable carriers, diluents or excipients, and, if desired, other active ingredients. The pharmaceutical compositions containing compounds of structural formulae (I)-(IV) may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

In some embodiments, the pharmaceutically acceptable carrier, diluent, or excipient is not water. In other embodiments, the water comprises less than 50% of the composition. In some embodiments, compositions comprising less than 50% water have at least 1%, 2%, 3%, 4% or 5% water. In other embodiments, the water content is present in the composition in a trace amount.

In some embodiments, the pharmaceutically acceptable carrier, diluent, or excipient is not alcohol. In other embodiments, the alcohol comprises less than 50% of the composition. In some embodiments, compositions comprising less than 50% alcohol have at least 1%, 2%, 3%, 4% or 5% alcohol. In other embodiments, the alcohol content is present in the composition in a trace amount.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Compounds of structural formulae (I)-(IV) can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

Compounds of structural formula (I)-(IV) can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

EXAMPLES

The compounds disclosed herein can be made using procedures familiar to the person of ordinary skill in the art and as described herein. For example, compounds of structural formulae (I)-(IV) can be prepared according to Schemes 1 or 2, below, or analogous synthetic schemes:

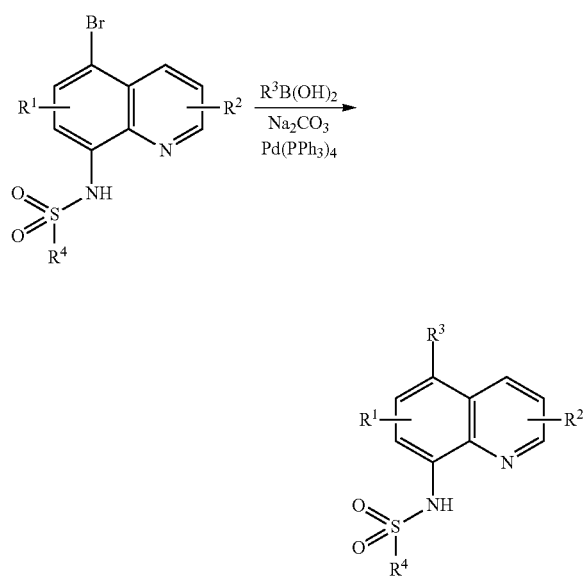

Referring to Scheme 1, to a mixture of the bromoisoquinoline and $R^3$-boronic acid (1.5 eq) in dioxane was added aqueous sodium carbonate (3.0 eq). The reaction mixture was degassed by bubbling argon through. Tetrakis(triphenylphosphine)palladium (0.1 eq) was added and the reaction further degassed before sealing and heating to 150° C. in the microwave for 1 hour. The reaction was cooled and partitioned between EtOAc and $NaHCO_3$. The organics were washed with brine, dried ($Na_2SO_4$) and concentrated under reduced pressure. MPLC yielded the Suzuki coupled compound.

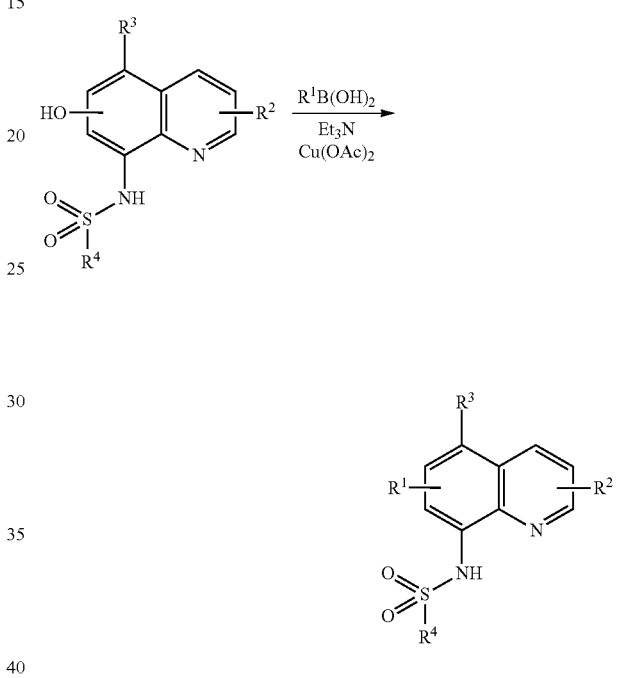

Referring to Scheme 2, to a solution of the 6-hydroxyquinoline (1.0 eq) and the $R^1$-boronic acid (2.0 eq) in dichloromethane was added freshly crushed 4 Å molecular sieves. Copper acetate (1.0 eq) was added followed by triethylamine (5.0 eq) and the reactions stirred at room temperature for 24 hours. The solution was diluted with $CH_2Cl_2$, washed with $NaHCO_3$, dried ($MgSO_4$) and concentrated under reduced pressure. Column chromatography yielded the aryl ethers.

One of skill in the art can adapt the reaction sequences of Schemes 1 and 2 to fit the desired target molecule. Of course, in certain situations one of skill in the art will use different reagents to affect one or more of the individual steps or to use protected versions of certain of the substituents. Additionally, one skilled in the art would recognize that compounds of structural formulae (I)-(IV) can be synthesized using different routes altogether.

Compounds suitable for use in the presently disclosed pharmaceutical compositions include compounds of Table 1, above. These compounds can be made according to the general schemes described above, for example using a procedure similar to that described below in the Examples.

The following examples are intended to further illustrate certain embodiments and are not intended to limit the scope of the presently disclosed compounds.

EXAMPLES

Example 1: Synthesis and Characterization

General Procedure for Sulfonamide Formation

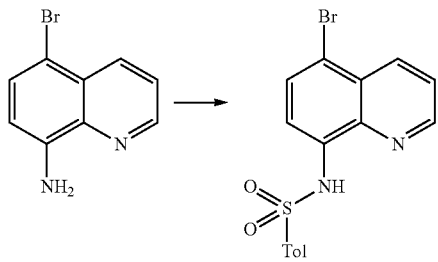

To a solution of 5-bromo-8-aminoquinoline (0.507 g, 2.27 mmol, 1.0 eq) in dichloromethane (15 mL) at 0° C. was added toluenesulfonyl chloride (0.477 g, 2.50 mmol, 1.1 eq) followed by triethylamine (0.47 mL, 3.41 mmol, 1.5 eq). The reaction was allowed to warm to room temperature and stirred for 20 hours. The reaction was partitioned between $CH_2Cl_2$ (50 mL) and $NaHCO_3$ (50 mL). The organics were washed with water (50 mL) and brine (50 mL) before drying ($Na_2SO_4$) and concentrating under reduced pressure. Column chromatography (silica, 20→70% EtOAc-hexane) yielded the sulfonamide.

Compound 1: N-(5-bromoquinolin-8-yl)-4-methyl-benzenesulfonamide

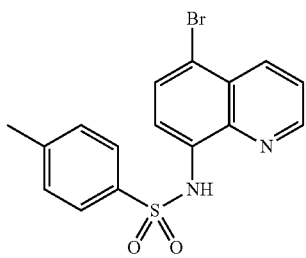 [SMILES: Cc1ccc(S(=O)(=O)Nc2ccc(Br)c3cccnc23)cc1]

$^1$H NMR (CDCl$_3$) δ 9.19 (1H, s, SO$_2$NH), 8.76 (1H, dd, J 4.0, 1.5 Hz, quinolineH-2), 8.42 (1H, dd, J 8.5, 1.5 Hz, quinolineH-4), 7.78 (2H, d, J 8.5 Hz, 2H of SO$_2$C$_6$H$_4$Me), 7.78, 7.67 (2H, 2d, J 8.5 Hz, quinolineH-6 and H-7), 7.50 (1H, dd, J 9.0, 4.0 Hz, quinolineH-3), 7.15 (2H, d, J 8.0 Hz, 2H of SO$_2$C$_6$H$_4$Me), 2.29 (3H, s, C$_6$H$_4$CH$_3$); $^{13}$C NMR (CDCl$_3$) δ 148.2, 144.0, 139.1, 136.2, 135.9, 133.8, 130.3, 129.6, 127.5, 127.2, 123.0, 115.2, 114.9, 21.5; m/z: 377, 379 [M+H]$^+$ (found [M+H]$^+$, 376.9989, C$_{16}$H$_{13}$BrN$_2$O$_2$S requires [M+H]$^+$ 376.9954)

Compound 4: 4-methyl-N-(5-phenylquinolin-8-yl)benzenesulfonamide

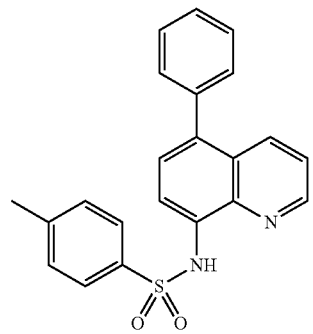 [SMILES: Cc1ccc(S(=O)(=O)Nc2ccc(-c3ccccc3)c3cccnc23)cc1]

To a solution of 5-chloroquinoline-8-sulfonyl chloride hydrochloric acid salt (0.030 g, 0.101 mmol, 1.0 eq) in dichloromethane (1 mL) was added p-toluidine (0.012 g, 0.111 mmol, 1.1 eq) followed by triethylamine (0.029 mL, 0.211 mmol, 2.1 eq) and dimethylaminopyridine (0.001 g, 0.010 mmol, 0.1 eq). The reaction was stirred at room temperature for 20 hours, before diluting with EtOAc-CH$_2$Cl$_2$ (35:5, 40 mL). The solution was washed with NaHCO$_3$ (40 mL), water (40 mL) and brine (40 mL). The organics were dried (Na$_2$SO$_4$) and concentrated under reduced pressure. MPLC (20→60% EtOAc-hexane) yielded the sulfonamide as a colorless oil; $^1$H NMR (CDCl$_3$) δ 9.20 (1H, dd, J 4.5, 1.5 Hz, quinolineH-2), 8.71 (1H, dd, J 8.5, 1.5 Hz, quinolineH-4), 8.24 (1H, d, J 8.0 Hz, quinolineH-6 or H-7), 8.17 (1H, s, SO$_2$NH), 7.72 (1H, dd, J 8.4, 4.5 Hz, quinolineH-3), 7.64 (1H, d, J 8.0 Hz, 1H of quinolineH-6 or H-7), 6.91 (2H, d, J 8.5 Hz, 2H of C$_6$H$_4$Me), 6.84 (2H, d, J 8.5 Hz, 2H of C$_6$H$_4$Me), 2.18 (3H, s, C$_6$H$_4$CH$_3$); m/z: 333, 335 [M+H]$^+$. To a mixture of phenylboronic acid (0.010 g, 0.082 mmol, 1.3 eq) and the chloroquinoline (0.021 g, 0.063 mmol, 1.0 eq) in dioxane (1 mL) was added sodium carbonate (0.063 mL of a 2M aqueous solution, 0.127 mmol, 2.0 eq). The mixture was degassed by bubbling argon through before adding tetrakis(triphenylphosphine)palladium (0.014 g, 0.013 mmol, 0.2 eq). The reaction was further degassed before sealing and heating in a microwave to 150° C. for 1 hour. After cooling the reaction was diluted with EtOAc (40 mL) and washed with NaHCO$_3$ (2×20 mL) and brine (20 mL). The organics were dried (Na$_2$SO$_4$) and concentrated under reduced pressure. Column chromatography (silica, 15→40% EtOAc-hexane) yielded the coupled compound as a colorless oil; $^1$H NMR (CDCl$_3$) δ 9.14 (1H, m, quinolineH-2), 8.42 (1H, s, SO$_2$NH), 8.34 (2H, m, quinolineH-4, 1H of quinolineH-6 or H-7), 7.56-7.48 (5H, m, quinolineH-3, quinolineH-6 or H-7, 3H of C$_6$H$_5$), 7.39 (2H, m, 2H of C$_6$H$_5$), 6.93 (4H, s, C$_6$H$_4$Me), 2.20 (3H, s, C$_6$H$_4$CH$_3$); m/z: 375 [M+H]$^+$.

General Procedure of the Suzuki Couplings

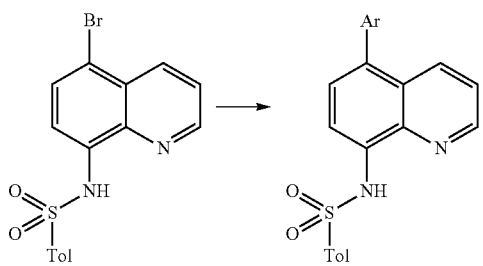

To a mixture of the bromoisoquinoline (0.085 mmol, 1.0 eq) and arylboronic acid (0.127 mmol, 1.5 eq) in dioxane (1.0 mL) was added aqueous sodium carbonate (0.127 mL of a 2M solution, 0.255 mmol, 3.0 eq). The reaction mixture was degassed by bubbling argon through. Tetrakis(triphenylphosphine)palladium (0.010 g, 0.008 mmol, 0.1 eq) was added and the reaction further degassed before sealing and heating to 150° C. in the microwave for 1 hour. The reaction was cooled and partitioned between EtOAc (30 mL) and NaHCO$_3$ (30 mL). The organics were washed with brine (30 mL), dried (Na$_2$SO$_4$) and concentrated under reduced pressure. MPLC (0→10% MeOH-CH$_2$Cl$_2$) yielded the Suzuki coupled compound.

Compound 5: N-(5-(furan-2-yl)quinolin-8-yl)-4-methylbenzenesulfonamide

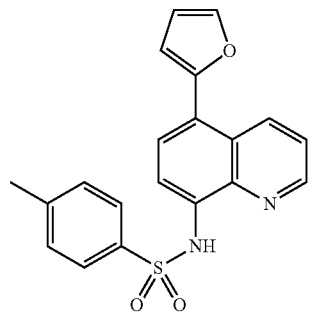

$^1$H NMR (CDCl$_3$) δ 9.36 (1H, br s, SO$_2$NH), 8.78 (1H, dd, J 4.0, 1.5 Hz, quinolineH-2), 8.72 (1H, dd, J 9.0, 1.5 Hz, quinolineH-4), 7.82 (3H, m, quinolineH-6 or H-7, 2H of SO$_2$C$_6$H$_4$Me), 7.66 (1H, d, J 8.0 Hz, quinolineH-6 or H-7), 7.58 (1H, d, J 2.0 Hz, furanH-H-3 or H-5), 7.46 (1H, dd, J 9.0, 4.5 Hz, quinolineH-3), 7.17 (2H, d, J 8.5 Hz, 2H of SO$_2$C$_6$H$_4$Me), 6.62 (1H, d, J 3.0 Hz, furanH-3 or H-5), 6.55 (1H, dd, J 3.0, 2.0 Hz, furanH-4), 2.30 (3H, s, C$_6$H$_4$CH$_3$); $^{13}$C NMR (CDCl$_3$) δ 148.5, 143.8, 142.7, 138.4, 136.4, 134.7, 133.8, 129.6, 127.2, 126.4, 125.5, 123.1, 122.2, 114.2, 111.5, 108.6, 21.5; m/z: 365 [M+H]$^+$ (found [M+H]$^+$, 365.0937, C$_{20}$H$_{16}$N$_2$O$_3$S requires [M+H]$^+$ 365.0955).

Compound 4: 4-methyl-N-(5-phenylquinolin-8-yl)benzenesulfonamide

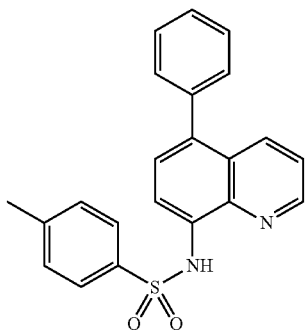

$^1$H NMR (CDCl$_3$) δ 9.33 (1H, br s, SO$_2$NH), 8.77 (1H, dd, J 4.5, 1.5 Hz, quinolineH-2), 8.20 (1H, dd, J 9.0, 2.0 Hz, quinolineH-4), 7.85 (3H, d, J 8.0 Hz, quinolineH-6 or H-7, 2H of SO$_2$C$_6$H$_4$Me), 7.47-7.35 (7H, m, quinolineH-6 or H-7, quinolineH-3, C$_6$H$_5$), 7.19 (2H, d, J 8.0 Hz, 2H of SO$_2$C$_6$H$_4$Me), 6.97 (1H, d, J 8.0 Hz, quinolineH-6 or H-7), 2.32 (3H, s, C$_6$H$_4$CH$_3$); $^{13}$C NMR (CDCl$_3$) δ 148.4, 143.7, 138.8, 138.5, 136.6, 134.7 (2C), 133.2, 130.0, 129.6, 128.5, 127.6, 127.3 (2C), 126.6, 121.8, 114.1, 21.5; m/z: 375 [M+H]$^+$ (found [M+H]$^+$, 375.1127, C$_{22}$H$_{18}$N$_2$O$_2$S requires [M+H]$^+$ 375.1162).

Compound 6: 4-methyl-N-(5-(pyridin-3-yl)quinolin-8-yl)benzenesulfonamide

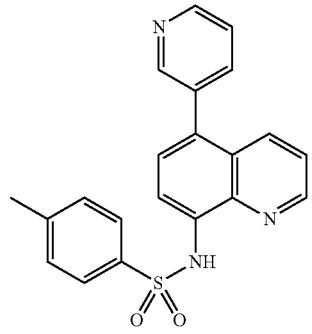 [SMILES: Cc1ccc(S(=O)(=O)Nc2ccc(-c3cccnc3)c3cccnc23)cc1]

$^1$H NMR (CDCl$_3$) δ 9.35 (1H, br s, SO$_2$NH), 8.80 (1H, br d, J 2.5 Hz, quinolineH-2), 8.66 (2H, m, quinolineH-4, pyH-2), 8.11 (1H, d, J 9.0 Hz, 1H of pyH-4, H-5 or H-6), 7.85 (3H, m, 2H of SO$_2$C$_6$H$_4$Me, 1H of pyH-4, H-5 or H-6), 7.71 (1H, br d, J 8.0 Hz, 1H of quinolineH-6 or H-7 or pyH-4, H-5 or H-6), 7.49-7.38 (3H, m, quinolineH-3, 2H of quinolineH-6 or H-7 or pyH-H-4, H-5 or H-6), 7.20 (2H, d, J 8.0 Hz, 2H of SO$_2$C$_6$H$_4$Me), 2.33 (3H, s, C$_6$H$_4$CH$_3$); $^{13}$C NMR (CDCl$_3$) δ 148.7, 143.9, 140.3, 140.1, 138.3, 136.5, 134.5, 134.2, 129.7, 128.9, 127.3, 126.7, 124.5, 124.1, 123.6, 122.3, 122.1, 113.6, 21.5; m/z: 381 [M+H]$^+$ (found [M+H]$^+$, 376.1114, C$_{21}$H$_{17}$N$_3$O$_2$S requires [M+H]$^+$ 376.1114).

Compound 7: 4-methyl-N-(5-(thiophen-3-yl)quinolin-8-yl)benzenesulfonamide

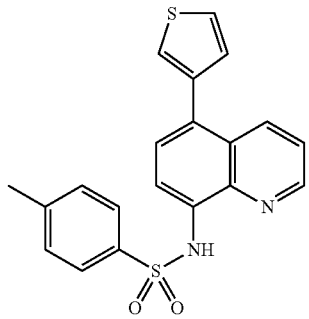 [SMILES: Cc1ccc(S(=O)(=O)Nc2ccc(-c3ccsc3)c3cccnc23)cc1]

$^1$H NMR (CDCl$_3$) δ 9.32 (1H, br s, SO$_2$NH), 8.77 (1H, dd, J 4.5, 1.5 Hz, quinolineH-2), 8.32 (1H, dd, J 8.5, 2.0 Hz, quinolineH-4), 7.84 (2H, d, J 8.5 Hz, 2H of SO$_2$C$_6$H$_4$Me), 7.83 (1H, d, J 8.0 Hz, quinolineH-6 or H-7), 7.46-7.43 (2H, m, quinolineH-6 or H-7, 1H of thiophene), 7.40 (1H, dd, J 8.5, 4.5 Hz, quinolineH-3), 7.30 (1H, dd, J 2.5, 1.5 Hz, 1H of thiophene), 7.19 (2H, d, J 8.5 Hz, 2H of SO$_2$C$_6$H$_4$Me), 7.18 (1H, m, 1H of thiophene), 2.31 (3H, s, C$_6$H$_4$C$\underline{H}$$_3$); $^{13}$C NMR (CDCl$_3$) δ 148.4, 143.7, 139.3, 138.5, 136.6, 134.6, 133.2, 129.6, 129.4, 129.1, 127.3, 126.8, 125.9, 123.7, 121.9, 114.2, 21.5; m/z: 381 [M+H]$^+$ (found [M+H]$^+$, 381.0710, C$_{20}$H$_{16}$N$_2$O$_2$S$_2$ requires [M+H]$^+$ 381.0726).

Compound 8: N-(5-(benzo[b]thiophen-2-yl)quinolin-8-yl)-4-methylbenzenesulfonamide

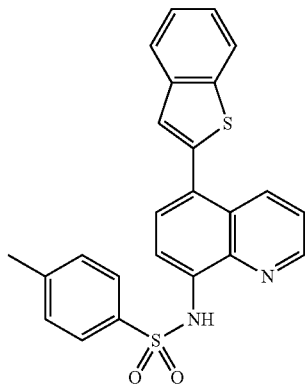 [SMILES: Cc1ccc(S(=O)(=O)Nc2ccc(-c3cc4ccccc4s3)c3cccnc23)cc1]

$^1$H NMR (CDCl$_3$) δ 9.32 (1H, br s, SO$_2$NH), 8.73 (1H, dd, J 4.0, 1.5 Hz, quinolineH-2), 8.51 (1H, dd, J 9.0, 1.5 Hz, quinolineH-4), 7.79 (2H, d, J 8.5 Hz, 2H of SO$_2$C$_6$H$_4$Me), 7.79-7.74 (3H, 3× ArH), 7.54 (1H, d, J 8.5 Hz, 1× ArH), 7.41-7.27 (4H, m, 4× ArH), 7.19 (2H, d, J 8.5 Hz, 2H of SO$_2$C$_6$H$_4$Me), 2.27 (3H, s, C$_6$H$_4$C$\underline{H}$$_3$); $^{13}$C NMR (CDCl$_3$) δ 148.7, 143.9, 140.3, 140.2, 140.1, 138.3, 136.5, 134.5, 134.2, 129.7, 128.9, 127.3, 126.9, 126.7, 124.7, 124.5, 124.1, 123.6, 122.3, 122.1, 113.6, 21.5; m/z: 431 [M+H]$^+$ (found [M+H]$^+$, 431.0887, C$_{24}$H$_{18}$N$_2$O$_2$S$_2$ requires [M+H]$^+$ 431.0876).

General Procedure for Buchwald-Hartwig Reactions

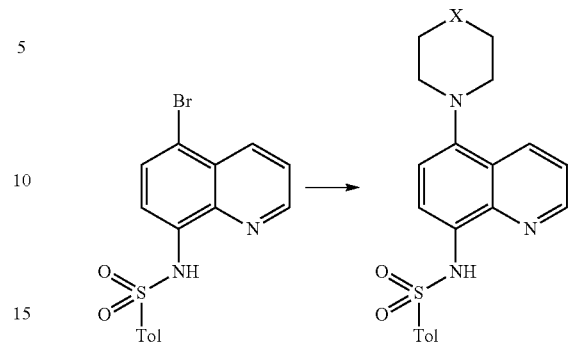

To a solution of bromoisoquinoline (0.035 g, 0.093 mmol, 1.0 eq) in N-methylpyrrolidinone (0.7 mL) was added the amine (0.18 mmol, 2.0 eq). The solution was degassed by bubbling argon through for three minutes before adding potassium carbonate (0.033 g, 0.29 mmol, 3.1 eq), X-Phos (0.004 g, 0.009 mmol, 0.09 eq) and tris(dibenzylideneacetone)dipalladium (0.004 g, 0.009 mmol, 0.09 eq). The reaction mixture was further degassed by bubbling argon through for three minutes and the reaction vessel sealed. The reaction was heated to 140° C. in a microwave for 10 minutes. After cooling the reaction mixture was poured onto aqueous NH$_4$Cl solution (5 mL). The resulting precipitate was collected and dissolved in CH$_2$Cl$_2$ (30 mL). The organics were washed with brine (30 mL), dried (Na$_2$SO$_4$) and concentrated under reduced pressure. The samples were isolated by reversed phase HPLC.

Compound 9: N-(5-(4-benzylpiperidin-1-yl)quinolin-8-yl)-4-methylbenzenesulfonamide

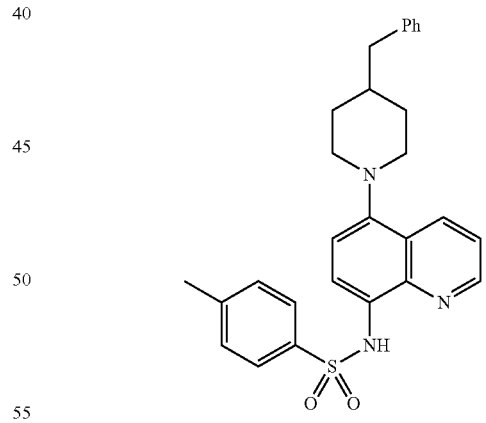

$^1$H NMR (CDCl$_3$) δ 9.01 (1H, br s, SO$_2$NH), 8.69 (1H, dd, J 4.0, 1.5 Hz, quinolineH-2), 8.40 (1H, dd, J 8.5, 1.5 Hz, quinolineH-4), 7.75 (2H, d, J 8.0 Hz, 2H of SO$_2$C$_6$H$_4$Me), 7.71 (1H, d, J 8.5 Hz, quinolineH-6 or H-7), 7.37 (1H, dd, J 8.5, 4.5 Hz, quinolineH-3), 7.33-7.28 (2H, m, 2H of C$_6$H$_5$), 7.23-7.18 (3H, m, 3H of C$_6$H$_5$), 7.11 (2H, d, J 8.5 Hz, 2H of SO$_2$C$_6$H$_4$Me), 6.97 (1H, d, J 8.0 Hz, quinolineH-6 or H-7), 3.20 (2H, m, 2H of pipH-2, H-6), 2.70-2.60 (4H, m, 2H of pipH-2, H-6, C$\underline{H}$$_2$C$_6$H$_5$), 2.28 (3H, s, C$_6$H$_4$C$\underline{H}$$_3$), 1.78 (2H, m, 2H of pipH-3, H-5), 1.74-1.65 (1H, m pipH-4), 1.56 (2H, m, 2H of pipH-3, H-5); $^{13}$C NMR (CDCl$_3$) δ 148.4, 146.0, 143.4, 140.4, 139.7, 136.6, 132.7, 129.4, 129.1, 128.2, 127.2, 125.9, 124.2, 120.9, 115.6, 115.1, 54.0, 43.3, 38.0, 32.8, 21.4; m/z: 472 [M+H]$^+$ (found [M+H]$^+$, 472.2047, $C_{28}H_{29}N_3O_2S$ requires [M+H]$^+$ 472.2053).

Compound 10: 4-methyl-N-(5-morpholinoquinolin-8-yl)benzenesulfonamide

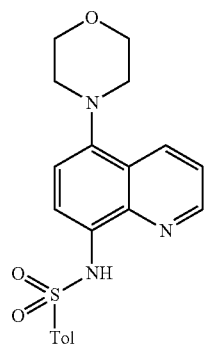

$^1$H NMR (CDCl$_3$) δ 9.06 (1H, br s, SO$_2$NH), 8.74 (1H, dd, J 4.0, 0.5 Hz, quinolineH-2), 8.46 (1H, dd, J 8.5, 1.0 Hz, quinolineH-4), 7.78 (2H, d, J 8.5 Hz, 2H of SO$_2$C$_6$H$_4$Me), 7.34 (1H, d, J 8.0 Hz, quinolineH-6 or H-7), 7.41 (1H, dd, J 8.5, 4.0 Hz, quinolineH-3), 7.15 (2H, d, J 8.0 Hz, 2H of SO$_2$C$_6$H$_4$Me), 7.05 (1H, d, J 8.5 Hz, quinolineH-6 or H-7), 3.93, 3.92 (4H, 2d AB system, J 4.5 Hz, 4H of morpholine), 3.01, 2.99 (4H, 2d AB system, J 4.5 Hz, 4H of morpholine), 2.30 (3H, s, C$_6$H$_4$CH$_3$); $^{13}$C NMR (CDCl$_3$) δ 148.6, 144.6, 143.5, 139.6, 136.6, 132.3, 129.9, 129.4, 127.2, 124.0, 121.2, 115.5, 115.2, 67.3, 53.6, 21.5; m/z: 384 [M+H]$^+$ (found [M+H]$^+$, 384.1338, $C_{20}H_{21}N_3O_3S$ requires [M+H]$^+$ 384.1377).

Compound 11: 4-methyl-N-(5-(4-methylpiperazin-1-yl)quinolin-8-yl)benzenesulfonamide

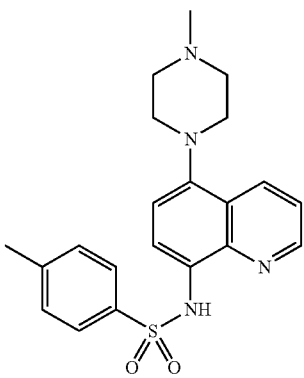 [SMILES: Cc1ccc(S(=O)(=O)Nc2ccc(N3CCN(C)CC3)c3cccnc23)cc1]

$^1$H NMR (CDCl$_3$) δ 9.02 (1H, br s, SO$_2$NH), 8.70 (1H, br s, quinolineH-2), 8.42 (1H, d, J 8.5 Hz, quinolineH-4), 7.77 (2H, d, J 8.0 Hz, 2H of SO$_2$C$_6$H$_4$Me), 7.70 (1H, m, quinolineH-3, H-6 or H-7), 7.37 (1H, m, quinolineH-3, H-6 or H-7), 7.12 (1H, m, quinolineH-3, H-6 or H-7), 7.02 (2H, d, J 8.5 Hz, 2H of SO$_2$C$_6$H$_4$Me), 3.02 (4H, m, 4H of piperazine), 2.65 (4H, m, 4H of piperazine), 2.39 (3H, s, NCH$_3$), 2.27 (3H, s, C$_6$H$_4$CH$_3$); $^{13}$C NMR (CDCl$_3$) δ 148.5, 144.9, 143.5, 139.7, 136.6, 132.5, 129.6, 129.4, 127.2, 124.1, 121.0, 115.5, 115.4, 55.5, 53.1, 46.2, 21.4; m/z: 397 [M+H]$^+$ (found [M+H]$^+$, 397.1694, $C_{20}H_{21}N_3O_3S$ requires [M+H]$^+$ 397.1693).

Demethylation of 6-methoxy-8-tosylsulfonamidoquinoline to form 6-hydroxy-8-tosylsulfonamidoquinoline

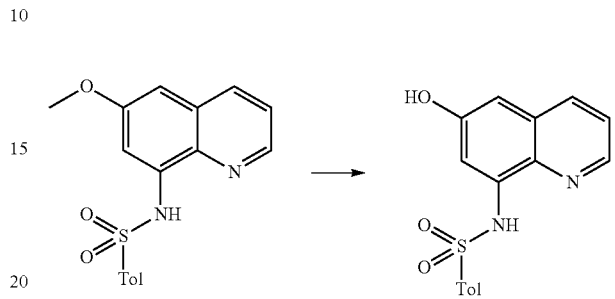

To a solution of the 6-methoxyquinoline (0.300 g, 2.43 mmol, 1.0 eq) in dichloromethane (25 mL) was cooled to −78° C. and boron tribromide (0.38 mL, 2.92 mmol, 1.2 eq) added dropwise. The yellow solution was stirred at −78° C. for 1.5 hours and 0° C. for 3 hours. Further boron tribromide (0.20 mL, 2.12 mmol, 0.9 eq) was added and the reaction stirred at 0° C. for 1 hour before adding NaHCO$_3$ (50 mL). The organics were extracted with CH$_2$Cl$_2$ (2×60 mL), combined, washed with brine (60 mL), dried (MgSO$_4$) and concentrated under reduced pressure. Column chromatography (silica, 0→5% MeOH-CH$_2$Cl$_2$) yielded the 6-hydroxy-8-tosylsulfonamidoquinoline.

General Procedure for Evans-Chan-Lam Reaction

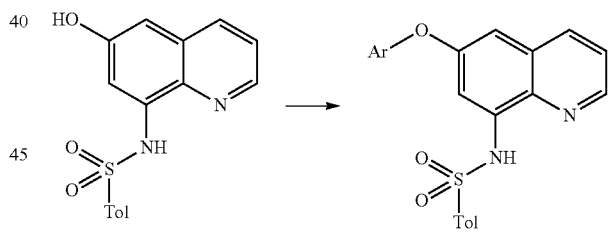

To a solution of the 6-hydroxyquinoline (0.020 g, 0.064 mmol, 1.0 eq) and the arylboronic acid (0.127 mmol, 2.0 eq) in dichloromethane (1.0 mL) was added freshly crushed 4 Å molecular sieves. Copper acetate (0.012 g, 0.064 mmol, 1.0 eq) was added followed by triethylamine (0.044 mL, 0.318 mmol, 5.0 eq) and the reactions stirred at room temperature for 24 hours. If LC-MS analysis showed only partial reaction, further boronic acid (0.127 mmol, 1.0 eq), triethylamine (0.018 mL, 0.128 mmol, 2.0 eq) and copper acetate (0.006 g, 0.032 mmol, 0.5 eq) was added and the reaction stirred for a further 14 hours before diluting with CH$_2$Cl$_2$ (20 mL). The solution was washed with NaHCO$_3$ (20 mL), dried (MgSO$_4$) and concentrated under reduced pressure. Column chromatography (silica, 0→3% MeOH-CH$_2$Cl$_2$) yielded the aryl ethers.

Compound 12: N-(6-(3,5-difluorophenoxy)quinolin-8-yl)-4-methylbenzenesulfonamide

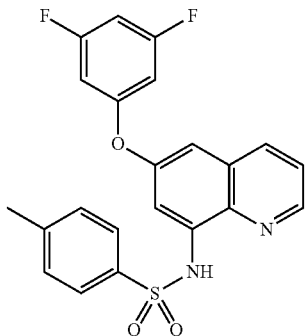 [SMILES: Cc1ccc(S(=O)(=O)Nc2cc(Oc3cc(F)cc(F)c3)cc3cccnc23)cc1]

$^1$H NMR (CDCl$_3$) δ 9.27 (1H, br s, NH), 8.71 (1H, dd, J 4.0, 1.5 Hz, quinolineH-2), 8.00 (1H, d, J 8.5 Hz, quinolineH-4), 7.76 (2H, d, J 8.5 Hz, 2H of C$_6$H$_4$SO$_2$Me), 7.54 (1H, d, J 2.5 Hz, quinolineH-5 or H-7), 7.42 (1H, dd, J 8.5, 4.0 Hz, quinolineH-3), 7.18 (2H, d, J 8.5 Hz, 2H of C$_6$H$_4$SO$_2$Me), 6.99 (1H, d, J 2.5 Hz, quinolineH-5 or H-7), 6.60 (1H, br t, J 9.0 Hz, C$_6$H$_3$F$_2$H-4), 6.43 (2H, d, J 8.5 Hz, C$_6$H$_3$F$_2$H-2, H-6), 2.34 (3H, s, SO$_2$CH$_3$); m/z: 427 [M+H]$^+$.

Compound 13: N-(6-(4-methoxyphenoxy)quinolin-8-yl)-4-methylbenzenesulfonamide

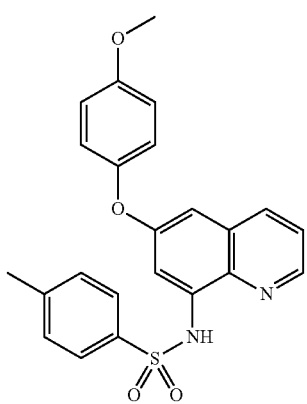 [SMILES: COc1ccc(Oc2cc(NS(=O)(=O)c3ccc(C)cc3)c3ncccc3c2)cc1]

$^1$H NMR (CDCl$_3$) δ 9.23 (1H, br s, NH), 8.62 (1H, m, quinolineH-2), 7.86 (1H, d, J 7.5 Hz, quinolineH-4), 7.78 (2H, d, J 7.5 Hz, 2H of C$_6$H$_4$SO$_2$Me), 7.53 (1H, m, quinolineH-5 or H-7), 7.33 (2H, m, quinolineH-3, quinolineH-5 or H-7), 7.19 (2H, d, J 7.5 Hz, 2H of C$_6$H$_4$SO$_2$Me), 6.99 (2H, d, J 9.5 Hz, 2H of C$_6$H$_4$OMe), 6.92 (2H, d, J 9.5 Hz, 2H of C$_6$H$_4$OMe), 3.85 (3H, s, OCH$_3$), 2.35 (3H, s, SO$_2$CH$_3$); m/z: 421 [M+H]$^+$.

Compound 14: N-(6-(3-cyanophenoxy)quinolin-8-yl)-4-methylbenzenesulfonamide

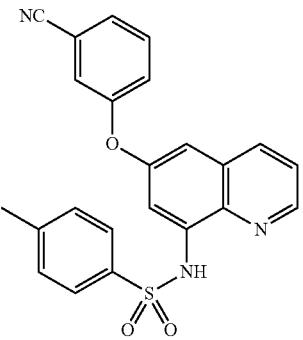 [SMILES: Cc1ccc(S(=O)(=O)Nc2cc(Oc3cccc(C#N)c3)cc3cccnc23)cc1]

m/z: 416 [M+H]$^+$.

Compound 15: N-(5-phenylquinolin-8-yl)methanesulfonamide

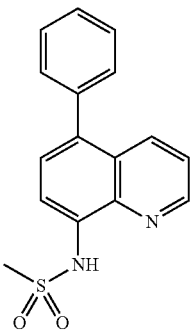 [SMILES: CS(=O)(=O)Nc1ccc(-c2ccccc2)c2cccnc12]

$^1$H NMR (CDCl$_3$) δ 9.02 (1H, br s, SO$_2$NH), 8.84 (1H, dd, J 4.5, 1.5 Hz, quinolineH-2), 8.30 (1H, dd, J 9.0, 1.5 Hz, quinolineH-4), 7.92 (1H, d, J 8.0 Hz, quinolineH-6 or H-7), 7.55-7.43 (7H, m, quinolineH-3, quinolineH-6 or H-7, C$_6$H$_5$), 3.08 (3H, s, SO$_2$CH$_3$); m/z: 299 [M+H]$^+$ (found [M+H]$^+$, 299.0824, C$_{16}$H$_{14}$N$_2$O$_2$S requires [M+H]$^+$ 299.0849).

Compound 16: N-(5-phenylquinolin-8-yl)cyclopropanesulfonamide

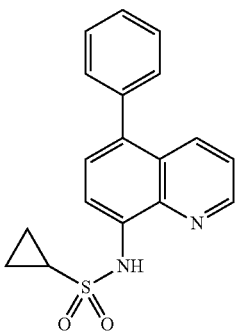

¹H NMR (CDCl₃) δ 9.02 (1H, br s, SO₂NH), 8.83 (1H, dd, J 4.5, 1.5 Hz, quinolineH-2), 8.29 (1H, dd, J 9.0, 1.5 Hz, quinolineH-4), 7.96 (1H, d, J 8.0 Hz, quinolineH-6 or H-7), 7.54-7.42 (7H, m, quinolineH-3, quinolineH-6 or H-7, C₆H₅), 2.59 (1H, tt, J 8.0, 5.0 Hz, cPrH-1), 1.31 (2H, m, 2H of cPrH-2, H-3), 0.92 (2H, m, 2H of cPrH-2, H-3); ¹³C NMR (CDCl₃) δ 148.6, 138.9, 138.8, 135.1, 134.8, 133.7, 130.0, 128.6, 127.7, 127.5, 126.7, 122.0, 115.1, 30.1, 5.7; m/z: 325 [M+H]⁺ (found [M+H]⁺, 325.0956, C₁₈H₁₆N₂O₂S requires [M+H]⁺ 325.1005).

Compound 17: 4-methoxy-N-(5-phenylquinolin-8-yl)benzenesulfonamide

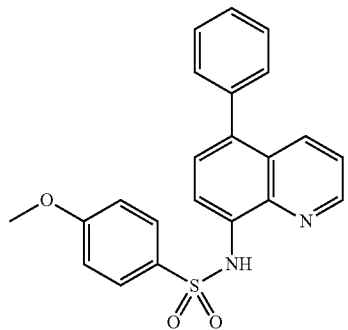 [SMILES: COc1ccc(S(=O)(=O)Nc2ccc(-c3ccccc3)c3cccnc23)cc1]

¹H NMR (CDCl₃) δ 9.30 (1H, br s, SO₂NH), 8.87 (1H, dd, J 4.5, 1.5 Hz, quinolineH-2), 8.20 (1H, dd, J 8.5, 1.5 Hz, quinolineH-4), 7.90 (2H, d, J 9.5 Hz, 2H of C₆H₄OMe), 7.85 (1H, d, J 8.0 Hz, quinolineH-6 or H-7), 7.50-7.35 (7H, m, quinolineH-3, quinolineH-6 or H-7, C₆H₅), 6.86 (2H, d, J 9.5 Hz, 2H of C₆H₄OMe), 3.78 (3H, s, OCH₃); ¹³C NMR (CDCl₃) δ 163.0, 152.2, 148.4, 138.8, 138.5, 134.7, 133.3, 131.2, 130.0, 129.4, 128.5, 127.6, 127.3, 126.6, 121.8, 114.2, 114.1, 55.5; m/z: 391 [M+H]⁺ (found [M+H]⁺, 391.1111, C₂₂H₁₈N₂O₃S requires [M+H]⁺ 391.1111).

Compound 18: N-(5-phenylquinolin-8-yl)-3-(trifluoromethyl)benzenesulfonamide

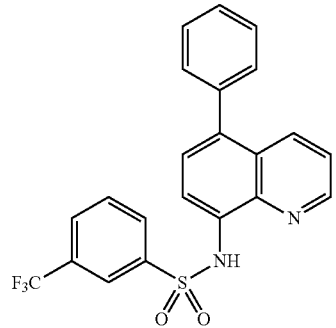 [SMILES: O=S(=O)(Nc1ccc(-c2ccccc2)c2cccnc12)c1cccc(C(F)(F)F)c1]

¹H NMR (CDCl₃) δ 9.34 (1H, s, SO₂NH), 8.75 (1H, dd, J 4.0, 1.5 Hz, quinolineH-2), 8.20 (1H, dd, J 8.5, 1.5 Hz, quinolineH-4), 8.19 (1H, s, C₆H₄CF₃H-2), 8.11 (1H, d, J 8.0 Hz, C₆H₄CF₃H-4, H-5 or H-6), 7.90 (1H, d, J 8.0 Hz, quinolineH-6 or H-7), 7.69 (1H, d, J 7.5 Hz, C₆H₄CF₃H-4, H-5 or H-6), 7.55-7.43 (5H, m, 5× ArH), 7.40-7.36 (3H, m, 3× ArH); ¹³C NMR (CDCl₃) δ 148.7, 140.6, 138.8, 138.6, 135.9, 134.9, 132.4, 131.5 (d, J 33.5 Hz), 130.4, 129.9, 129.7, 129.5 (m), 128.6, 127.7, 127.2, 126.7, 124.4 (d, J 3.5 Hz), 122.0, 115.6; ¹⁹F NMR (CDCl₃) δ −63.0; m/z: 429 [M+H]⁺ (found [M+H]⁺, 429.0872, C₂₂H₁₅F₃N₂O₂S requires [M+H]⁺ 429.0879).

Compound 19: N-(5-phenylquinolin-8-yl)pyridine-3-sulfonamide

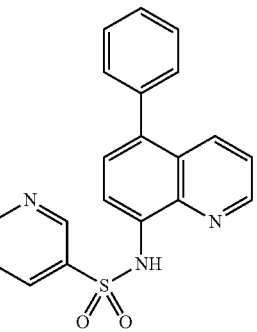

¹H NMR (CDCl₃) δ 9.40 (1H, br s, NH), 9.13 (1H, d, J 2.0 Hz, pyH-2), 8.76 (1H, dd, J 4.0, 3.0 Hz, quinolineH-2), 8.67 (1H, dd, J 5.0, 1.5 Hz, pyH-4 or H-6), 8.24-8.20 (2H, m, quinolineH-4, pyH-5), 7.92 (1H, d, J 8.0 Hz, quinolineH-6 or H-7), 7.51-7.32 (8H, m, quinolineH-3, quinolineH-6 or H-7, pyH-4 or H-6, C₆H₅); ¹³C NMR (CDCl₃) δ 153.4, 148.7, 148.0, 138.6, 136.1, 135.8, 134.9, 132.3, 129.9, 128.6, 127.7, 127.3, 126.7, 123.6, 122.0, 115.2; m/z: 362 [M+H]⁺ (found [M+H]⁺, 362.0969, C₂₀H₁₅N₃O₂S requires [M+H]⁺362.0958).

Compound 20: N-(4-(N-(5-phenylquinolin-8-yl)sulfamoyl)phenyl)acetamide

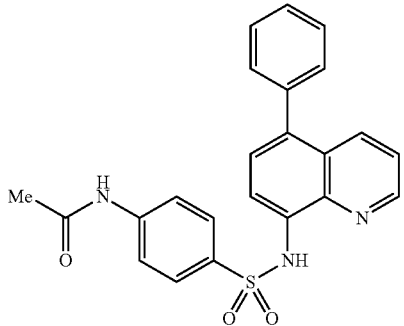 [SMILES: CC(=O)Nc1ccc(S(=O)(=O)Nc2ccc(-c3ccccc3)c3cccnc23)cc1]

¹H NMR (CDCl₃) δ 9.32 (1H, br s, NH), 8.77 (1H, dd, J 8.0, 1.5 Hz, quinolineH-2), 8.20 (1H, dd, J 8.5, 1.5 Hz, quinolineH-4), 7.90 (2H, d, J 8.5 Hz, 2H of C₆H₄NHCO), 7.85 (1H, d, J 8.0 Hz, quinolineH-6 or H-7), 7.53 (2H, d, J 9.0 Hz, 2H of C₆H₄NHCO), 7.49-7.35 (7H, m, quinolineH-3, quinolineH-6 or H-7, C₆H₅), 7.31 (1H, br s, NHCO), 2.15 (3H, s, COCH₃); ¹³C NMR (CDCl₃) δ 148.5, 142.0, 138.8, 138.5, 134.9, 134.8, 133.0, 130.0, 126.8, 128.5, 127.6, 127.3, 126.6, 121.9, 119.1, 114.4, 24.7; m/z: 418 [M+H]⁺ (found [M+H]⁺, 418.1180, C₂₃H₁₉N₃O₃S requires [M+H]⁺ 418.1220).

Compound 21: N-(5-(pyridin-3-yl)quinolin-8-yl)methanesulfonamide

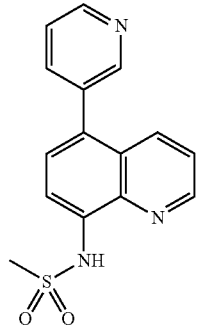 [SMILES: CS(=O)(=O)Nc1ccc(-c2cccnc2)c2cccnc12]

¹H NMR (CDCl₃) δ 9.08 (1H, br s, SO₂NH), 8.87 (1H, m, quinolineH-2), 8.72 (2H, m, pyH-2, H-6), 8.20 (1H, dd, J 8.5, 1.5 Hz, quinolineH-4), 7.94 (1H, d, J 7.5 Hz, quinolineH-6 or H-7), 7.79 (1H, br d, J 7.5 Hz, pyH-4), 7.53-7.45 (3H, m, quinolineH-3, quinolineH-6 or H-7, pyH-5), 3.10 (3H, s, SO₂CH₃); ¹³C NMR (CDCl₃) δ 150.5, 149.0 (2C), 138.6, 137.3, 134.5, 134.4, 134.2, 131.2, 128.1, 126.7, 123.5, 122.6, 114.4, 39.5; m/z: 300 [M+H]⁺ (found [M+H]⁺, 300.0788, C₁₅H₁₃N₁₃O₂S requires [M+H]⁺ 300.0801).

Compound 23: 4-methoxy-N-(5-(pyridin-4-yl)quinolin-8-yl)benzenesulfonamide

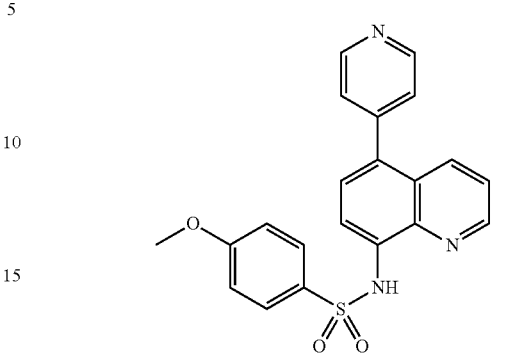

¹H NMR (CDCl₃) δ 9.34 (1H, br s, SO₂NH), 8.81 (1H, dd, J 4.0, 1.5 Hz, quinolineH-2), 8.67 (2H, m, pyH-2, H-6), 8.12 (1H, dd, J 8.5, 1.0 Hz, quinolineH-4), 7.91 (2H, d, J 8.5 Hz, 2H of C₆H₄OMe), 7.87 (1H, d, J 8.5 Hz, quinolineH-6 or H-7 or pyH-4), 7.72 (1H, dt, J 8.0, 2.0 Hz, quinolineH-6 or H-7 or pyH-4), 7.45-7.39 (3H, m, quinolineH-3, quinolineH-6 or H-7, pyH-5), 6.87 (2H, d, J 9.0 Hz, 2H of C₆H₄OMe), 3.78 (3H, s, OCH₃); ¹³C NMR (CDCl₃) δ 163.1, 150.5, 148.9, 148.7, 138.5, 137.2, 134.1, 134.0, 131.0, 130.5, 129.4, 128.0, 126.5, 123.4, 122.3, 114.2, 113.9, 55.5; m/z: 392 [M+H]⁺ (found [M+H]⁺, 392.1040, C₂₁H₁₇N₃O₃S requires [M+H]⁺ 392.1063).

Compound 22: N-(5-(pyridin-3-yl)quinolin-8-yl)cyclopropanesulfonamide

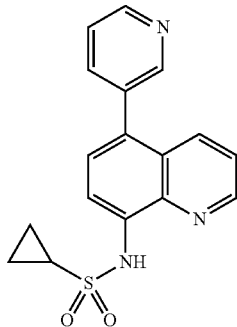 [SMILES: O=S(=O)(Nc1ccc(-c2cccnc2)c2cccnc12)C1CC1]

¹H NMR (CDCl₃) δ 9.06 (1H, br s, SO₂NH), 8.88 (1H, dd, J 4.0, 1.5 Hz, quinolineH-2), 8.73-8.70 (2H, m, pyH-2, H-6), 8.20 (1H, dd, J 8.5, 1.5 Hz, quinolineH-4), 8.00 (1H, d, J 8.0 Hz, quinolineH-6 or H-7), 7.79 (1H, dt, J 7.5, 2.0 Hz, pyH-4), 7.51-7.44 (3H, m, quinolineH-3, quinolineH-6 or H-7, pyH-5), 2.62 (1H, tt, J 8.0, 5.0 Hz, cPrH-1), 1.33 (2H, m, 2H of cPrH-2, H-3), 0.95 (2H, m, 2H of cPrH-2, H-3); ¹³C NMR (CDCl₃) δ 150.5, 149.0, 148.9, 138.8, 137.3, 134.6, 134.1, 130.9, 128.1, 126.7, 123.4, 122.4, 114.7, 30.3, 5.8; m/z: 326 [M+H]⁺ (found [M+H]⁺, 326.0949, C₁₇H₁₅N₃O₂S requires [M+H]⁺ 326.0958).

Compound 24: N-(5-(pyridin-3-yl)quinolin-8-yl)-3-(trifluoromethyl)benzenesulfonamide

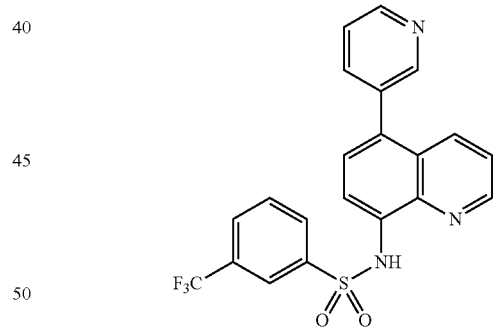

¹H NMR (CDCl₃) δ 9.39 (1H, br s, SO₂NH), 8.81 (1H, dd, J 4.0, 1.5 Hz, quinolineH-2), 8.69 (1H, dd, J 5.0, 1.5 Hz, pyH-6), 8.66 (1H, d, J 2.0 Hz, pyH-2), 8.20 (1H, s, C₆H₄CF₃H-2), 8.12 (2H, m, quinolineH-2, C₆H₄CF₃H-4 or H-6), 7.93 (1H, d, J 8.0 Hz, quinolineH-6 or H-7), 7.74-7.70 (2H, m, pyH-5, C₆H₄CF₃H-4 or H-6), 7.55 (1H, t, J 8.0 Hz, C₆H₄CF₃H-5), 7.46-7.41 (4H, m, quinolineH-3, H-6 or H-7, pyH-4); ¹³C NMR (CDCl₃) δ 150.4, 149.0, 140.5, 138.7, 137.2, 134.4, 134.1, 133.3, 131.7, 130.3 (d, J 1.0 Hz), 129.8, 129.6, 127.9, 126.6, 124.5 (q, J 3.5 Hz), 123.4, 122.5; ¹⁹F NMR (CDCl₃) δ −63.0; m/z: 430 [M+H]⁺ (found [M+H]⁺, 430.0804, C₂₁H₁₄F₃N₃O₂S requires [M+H]⁺ 430.0832).

Compound 25: N-(5-(pyridin-3-yl)quinolin-8-yl)pyridine-3-sulfonamide

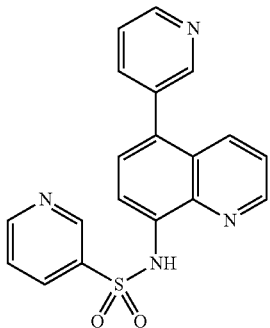 [SMILES: O=S(=O)(Nc1ccc(-c2cccnc2)c2cccnc12)c1cccnc1]

¹H NMR (CDCl₃) δ 9.45 (1H, br s, SO₂NH), 9.15 (1H, dd, J 2.5, 1.0 Hz, 1× pyH-2), 8.81 (1H, m, quinolineH-2), 8.69 (2H, dd, J 5.0, 1.5 Hz, 2H of 2× pyH-4, H-6), 8.66 (1H, dd, J 2.0, 1.0 Hz, 1× pyH-2), 8.24 (1H, ddd, J 7.5, 2.5, 2.0 Hz, 1× pyH-4 or H-6), 8.13 (1H, dd, J 8.5, 1.5 Hz, quinolineH-4), 7.95 (1H, d, J 8.0 Hz, quinolineH-6 or H-7), 7.73 (1H, ddd, J 8.0, 2.0, 1.5 Hz, 1× pyH-4 or H-6), 7.46-7.41 (3H, m, quinolineH-3, quinolineH-6 or H-7, 1× pyH-5), 7.35 (1H, ddd, J 8.0, 5.0, 1.0 Hz, 1× pyH-5); ¹³C NMR (CDCl₃) δ 153.5, 150.4, 149.1, 149.0, 148.0, 138.6, 137.2, 136.0, 137.2, 136.0, 134.9, 134.3, 134.2, 133.2, 131.7, 127.9, 126.6, 123.7, 123.4, 122.5, 114.9; m/z: 363 [M+H]⁺ (found [M+H]⁺, 363.0807, $C_{19}H_{14}N_4O_2S$ requires [M+H]⁺ 363.0910).

Compound 26: N-(4-(N-(5-(pyridin-3-yl)quinolin-8-yl)sulfamoyl)phenyl)acetamide

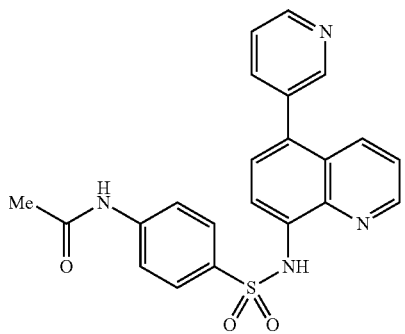

¹H NMR (CDCl₃) δ 9.36 (1H, br s, SO₂NH), 8.81 (1H, dd, 4.0, 2.0 Hz, quinolineH-2), 8.66 (2H, m, pyH-2, H-6), 8.11 (1H, dd, J 8.5, 12.0 Hz, quinolineH-4), 7.91 (2H, d, J 9.0 Hz, 2H of C₆H₄NHAc), 7.87 (1H, d, J 8.0 Hz, quinolineH-6 or H-7), 7.73 (1H, ddd, J 8.5, 2.0, 1.5 Hz, pyH-4), 7.55 (2H, d, J 9.0 Hz, 2H of C₆H₄NHAc), 7.45-7.39 (4H, m, quinolineH-3, quinolineH-6 or H-7, pyH-5, NHAc), 2.15 (3H, s, COCH₃); ¹³C NMR (CDCl₃) δ 160.8, 150.5, 148.9, 148.8, 142.1, 138.5, 137.3, 134.6, 134.1, 134.0, 133.9, 130.8, 128.6, 127.9, 126.5, 123.4, 122.3, 119.2, 114.1, 24.7; m/z: 419 [M+H]⁺ (found [M+H]⁺, 419.1172, $C_{22}H_{18}N_4O_3S$ requires [M+H]⁺ 419.1164).

Compound 27: N-(5-(pyridin-4-yl)quinolin-8-yl)methanesulfonamide

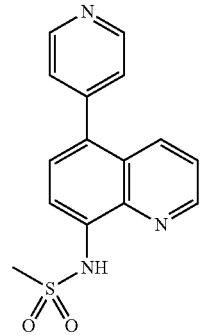 [SMILES: CS(=O)(=O)Nc1ccc(-c2ccncc2)c2cccnc12]

¹H NMR (CDCl₃) δ 9.08 (1H, br s, SO₂NH), 8.87 (1H, m, quinolineH-2), 8.75 (2H, d, J 5.5 Hz, 2H of py), 8.25 (1H, dd, J 8.5, 1.0 Hz, quinolineH-4), 7.93 (1H, d, J 8.0 Hz, quinolineH-6 or H-7), 7.51 (2H, m, quinolineH-3, quinolineH-6 or H-7), 7.39 (2H, d, J 5.5 Hz, 2H of py), 3.10 (3H, s, SO₂CH₃); ¹³C NMR (CDCl₃) δ 150.1, 149.0, 146.6, 138.5, 134.7, 134.0, 132.1, 127.7, 126.1, 124.8, 122.6, 114.2, 39.5; m/z: 300 [M+H]⁺ (found [M+H]⁺, 300.0789, $C_{15}H_{13}N_3O_2S$ requires [M+H]⁺ 300.0801).

Compound 28: N-(5-(pyridin-4-yl)quinolin-8-yl)cyclopropanesulfonamide

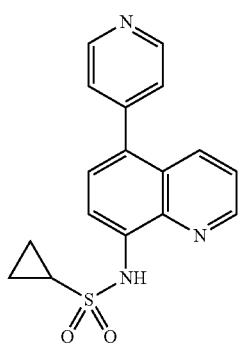 [SMILES: O=S(=O)(Nc1ccc(-c2ccncc2)c2cccnc12)C1CC1]

¹H NMR (CDCl₃) δ 9.08 (1H, br s, SO₂NH), 8.88 (1H, m, quinolineH-2), 8.75 (2H, d, J 5.5 Hz, pyH-2, H-6), 8.25 (1H, br d, J 8.5 Hz, quinolineH-4), 7.98 (1H, d, J 7.5 Hz, quinolineH-6 or H-7), 7.52-7.48 (2H, m, quinolineH-3, quinolineH-6 or H-7), 7.40 (2H, d, J 5.5 Hz, pyH-3, H-5), 2.61 (1H, tt, J 8.0, 5.0 Hz, cPrH-1), 1.34 (2H, m, 2H of cPrH-2, H-3), 0.95 (2H, m, 2H of cPrH-2, H-3); ¹³C NMR (CDCl₃) δ 150.1, 148.9, 146.7, 138.7, 135.0, 134.0, 131.8, 127.7, 126.0, 124.9, 122.5, 114.5, 30.3, 5.8; m/z: 326 [M+H]⁺ (found [M+H]⁺, 326.0953, $C_{17}H_{15}N_3O_2S$ requires [M+H]⁺ 326.0958).

Compound 29: 4-methoxy-N-(5-(pyridin-3-yl)quinolin-8-yl)benzenesulfonamide

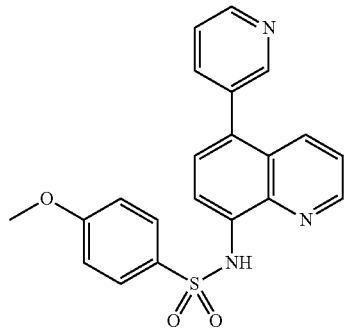 [SMILES: COc1ccc(S(=O)(=O)Nc2ccc(-c3cccnc3)c3cccnc23)cc1]

$^1$H NMR (CDCl$_3$) δ 9.33 (1H, br s, SO$_2$NH), 8.82 (1H, m, quinolineH-2), 8.71 (2H, d, J 5.5 Hz, pyH-2, H-6), 8.17 (1H, dd, J 8.0, 1.5 Hz, quinolineH-4), 7.91 (2H, d, J 9.0 Hz, 2H of C$_6$H$_4$OMe), 7.86 (1H, d, J 8.0 Hz, quinolineH-6 or H-7), 7.43 (2H, m, quinolineH-3, quinolineH-6 or H-7), 7.34 (2H, d, J 5.5 Hz, pyH-3, H-5), 6.88 (2H, d, J 9.5 Hz, 2H of C$_6$H$_4$OMe), 3.79 (3H, s, OCH$_3$); m/z: 392 [M+H] (found [M+H]$^+$, 392.1086, C$_{21}$H$_{17}$N$_3$O$_3$S requires [M+H]$^+$ 392.1063).

Compound 30: N-(5-(pyridin-4-yl)quinolin-8-yl)pyridine-3-sulfonamide

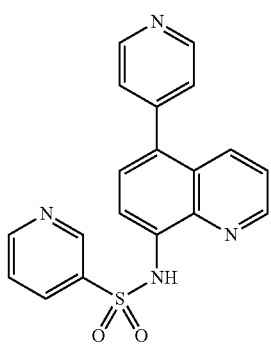 [SMILES: O=S(=O)(Nc1ccc(-c2ccncc2)c2cccnc12)c1cccnc1]

$^1$H NMR (CDCl$_3$) δ 9.45 (1H, br s, SO$_2$NH), 9.14 (1H, dd, J 2.5, 1.0 Hz, pyH-2), 8.82 (1H, dd, J 4.0, 1.5 Hz, quinolineH-2), 8.73 (2H, d, J 6.0 Hz, pyH-2, H-6), 8.70 (1H, dd, J 5.0, 1.5 Hz, pyH-6), 8.24 (1H, ddd, J 8.0, 2.5, 1.5 Hz, pyH-4), 8.18 (1H, dd, J 8.5, 1.5 Hz, quinolineH-4), 7.95 (1H, d, J 8.0 Hz, quinolineH-6 or H-7), 7.45 (2H, m, quinolineH-3, quinolineH-6 or H-7), 7.37 (1H, m, pyH-5), 7.34 (2H, d, J 6.0 Hz, pyH-3, H-5); $^{13}$C NMR (CDCl$_3$) δ 153.5, 150.1, 149.0, 148.0, 146.4, 138.5, 136.1, 134.8, 134.0, 133.6, 132.6, 127.5, 126.0, 124.7, 123.6, 122.5, 114.8; m/z: 363 [M+H]$^+$ (found [M+H]$^+$, 363.0913, C$_{19}$H$_{14}$N$_4$O$_2$S requires [M+H]$^+$ 363.0910).

Compound 31: N-(4-(N-(5-(pyridin-4-yl)quinolin-8-yl)sulfamoyl)phenyl)acetamide

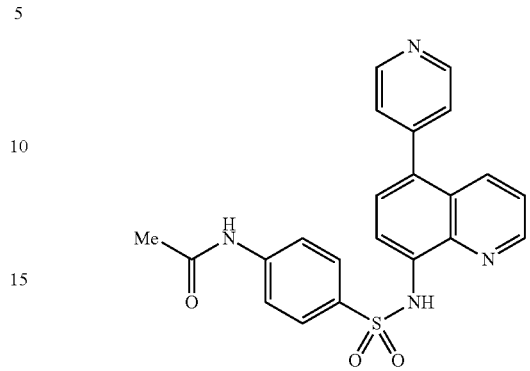

$^1$H NMR (CDCl$_3$) δ 9.38 (1H, br s, SO$_2$NH), 8.81 (1H, dd, J 4.5, 1.5 Hz, quinolineH-2), 8.71 (2H, d, J 6.0 Hz, pyH-2, H-6), 8.17 (1H, dd, J 8.5, 1.5 Hz, quinolineH-4), 7.89 (2H, d, J 9.0 Hz, 2H of C$_6$H$_4$NHAc), 7.86 (1H, d, J 8.5 Hz, quinolineH-6 or H-7), 7.81 (1H, s, NH), 7.56 (2H, d, J 9.0 Hz, 2H of C$_6$H$_4$NHAc), 7.44 (1H, dd, J 8.5, 4.5 Hz, quinolineH-3), 7.41 (1H, d, J 8.0 Hz, quinolineH-6 or H-7), 7.35 (2H, d, J 5.5 Hz, pyH-3, H-5), 2.14 (3H, s, COCH$_3$); $^{13}$C NMR (CDCl$_3$) δ 168.7, 150.0, 148.8, 146.8, 142.4, 138.4, 134.2, 133.9, 131.7, 128.6, 127.6, 125.9, 124.9, 122.5, 119.3, 113.9, 24.6; m/z: 419 [M+H]$^+$ (found [M+H]$^+$, 419.1224, C$_{22}$H$_{18}$N$_4$O$_3$S requires [M+H]$^+$ 419.1173).

Example 2: Cks1-Skp2 Protein-Protein Interaction

In vitro binding of Skp2 to Cks1 was established in an ELISA assay format, with Cks1 protein immobilized on a 384-well plate and binding of Skp1/Skp2 to Cks1 detected by anti-Skp2 immunoreaction.

TABLE 1

Potency of compounds in the interaction assay.

| Compound | Cks1-Skp2 (μM) | GFP-p27 |
|---|---|---|
| 1 | 0.84 | ++ |
| 4 | 0.54 | + |
| 5 | 0.55 | + |
| 6 | 1.73 | + |
| 7 | 5.54 | + |
| 8 | 7.84 | + |
| 12 | 3.57 | + |
| 13 | 1.15 | NA |
| 14 | 1.74 | NA |

Example 3: p27-GFP Stabilization

A constitutively degraded mutant p27(T187D) is fused to GFP and used as a reporter for SCF-Skp2 E3 ligase activity in Hela cells. Inhibition of Cks1-Skp2 interaction by the compounds will inhibit p27 ubiquitination and degradation, thus stabilizing p27-GFP protein levels within the cells.

TABLE 2

Potency of the sulfonamide analogues in the Cks1-Skp2 interaction assay (µM).

| Compound | Potency (µM) |
|---|---|
| 15 | 2.20 |
| 16 | 12.10 |
| 17 | 8.02 |
| 18 | 6.70 |
| 19 | 2.20 |
| 20 | 7.60 |
| 21 | 15.13 |
| 22 | 7.16 |
| 23 | 0.58 |
| 24 | 0.17 |
| 25 | 1.67 |
| 26 | 14.49 |
| 28 | 10.94 |
| 29 | 2.45 |
| 30 | 1.21 |
| 31 | 6.55 |

Example 4: Inhibition of Tumor Cell Growth

Compounds that were able to inhibit the interaction of Cks1-Skp2 were screened in both the lung tumor cell line A549 and the fibrosarcoma HT1080, which have been shown to be sensitive to p27.

TABLE 3

Potency of selected compounds against two cancer cell lines.

| | IC$_{50}$ (µM) | | |
|---|---|---|---|
| Compound | Cks1-Skp2 | A549 | HT1080 |
| 4 | 0.54 | 2.36 | 1.64 |
| 5 | 0.55 | 26.01 | 9.78 |
| 6 | 1.73 | 6.02 | 4.22 |
| 7 | 5.54 | 2.36 | 0.64 |
| 8 | 7.84 | 0.39 | 0.15 |
| 12 | 3.57 | 4.11 | 0.08 |
| 13 | 1.15 | 4.09 | 0.74 |
| 14 | 1.74 | 6.48 | 6.83 |
| 23 | 0.58 | 1.24 | 0.44 |
| 24 | 0.17 | 0.91 | 0.40 |
| 25 | 1.67 | 5.24 | 1.07 |
| 29 | 2.45 | 3.06 | 1.32 |
| 30 | 1.21 | 5.88 | 1.07 |

What is claimed:

1. A compound having structural formula (Ia),

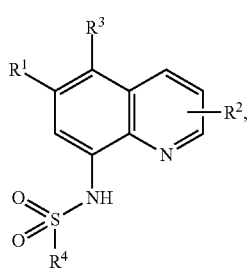

(Ia)

or a pharmaceutically acceptable salt, or N-oxide thereof, or solvate or hydrate thereof, wherein $R^1$ is -hydrogen, —O—Ar, or —O-Het, wherein —O—Ar and —O-Het are each optionally substituted with one or more —($C_1$-$C_6$ alkyl), —O—($C_1$-$C_6$ haloalkyl), -halogen, —$NO_2$ or —CN;

$R^2$ is -hydrogen, —($C_1$-$C_6$ alkyl), —($C_1$-$C_6$ haloalkyl), —O—($C_1$-$C_6$ alkyl), —O—($C_1$-$C_6$ haloalkyl), -halogen, —$NO_2$ or —CN, wherein —($C_1$-$C_6$ alkyl), —($C_1$-$C_6$ haloalkyl), —O—($C_1$-$C_6$ alkyl), and —O—($C_1$-$C_6$ haloalkyl) are each optionally substituted with one or more —($C_1$-$C_6$ alkyl), —($C_1$-$C_6$ haloalkyl), -halogen, —$NO_2$ or —CN;

$R^3$ is -hydrogen, —Ar, or -Het, wherein —Ar and -Het are each optionally substituted with one or more —($C_1$-$C_6$ alkyl), —($C_1$-$C_6$ haloalkyl), —($C_1$-$C_6$ alkyl)—Ar, -halogen, —$NO_2$ or —CN; and $R^4$ is —($C_1$-$C_6$ alkyl), —($C_1$-$C_6$ haloalkyl), —($C_0$-$C_6$ alkyl)-Ar, —($C_0$-$C_6$ alkyl)-Het or —($C_0$-$C_6$ alkyl)-Cak, wherein —($C_1$-$C_6$ haloalkyl), —($C_0$-$C_6$ alkyl)-Ar, —($C_0$-$C_6$ alkyl)-Het and —($C_0$-$C_6$ alkyl)-Cak are each optionally substituted with one or more —($C_1$-$C_6$ alkyl), —($C_1$-$C_6$ haloalkyl), —O—($C_1$-$C_6$ alkyl), N($R^5$)($R^6$), -halogen, —$NO_2$ or —CN, wherein $R^5$ and $R^6$ are independently -hydrogen, —($C_1$-$C_6$ alkyl) or —C(O)—($C_1$-$C_6$ alkyl), provided that at least one of $R^1$ and $R^3$ is not hydrogen.

2. The compound of claim 1, wherein
$R^1$ is optionally substituted —O—Ar.

3. The compound of claim 1, wherein
$R^3$ is optionally substituted —Ar.

4. The compound of claim 1, wherein
$R^1$ is optionally substituted —O-Het.

5. The compound of claim 1, wherein
$R^3$ is optionally substituted -Het.

6. The compound of claim 1, wherein
$R^2$ is -hydrogen, —($C_1$-$C_6$ haloalkyl), —O—($C_1$-$C_6$ haloalkyl), -halogen, —$NO_2$ or —CN.

7. The compound of claim 1, wherein
$R^2$ is —($C_1$-$C_6$ haloalkyl), —O—($C_1$-$C_6$ haloalkyl), -halogen, —$NO_2$ or —CN.

8. The compound of claim 1, wherein $R^2$ is hydrogen.

9. The compound of claim 1, wherein $R^2$ is halogen.

10. The compound of claim 1, having the structure of formula (II),

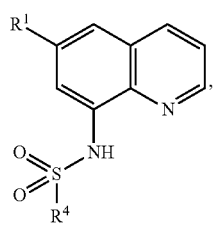
(II)

wherein R¹ is —O—Ar or —O-Het.

11. The compound of claim 1, having the structure of formula (III),

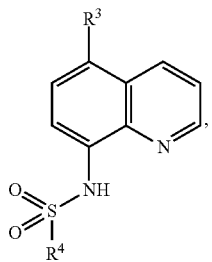
(III)

wherein R³ is —Ar, or -Het.

12. The compound of claim 1 having structural formula (IV),

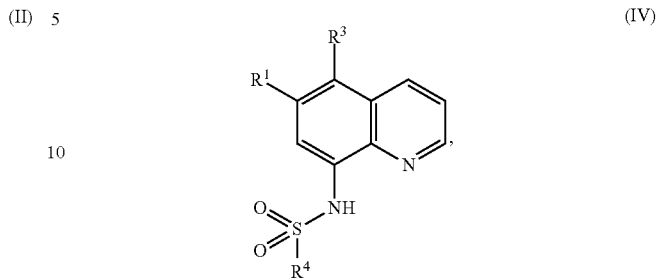
(IV)

or a pharmaceutically acceptable salt, or N-oxide thereof, or solvate or hydrate thereof,
wherein
R¹ is -hydrogen or optionally substituted —O—Ar,
R⁴ is optionally substituted —($C_0$-$C_6$ alkyl)-Ar or —($C_0$-$C_6$ alkyl)-Het.

13. The compound of claim 1, wherein
R¹ is —O—Ar.

14. The compound of claim 1, wherein
R¹ is —O-Het.

15. A pharmaceutical composition comprising a pharmaceutically acceptable diluent, carrier, or excipient and a compound according to claim 1.

16. A method for inhibiting Cks1-Skp2 PPI, comprising administering an effective Cks1-Skp2 PPI inhibiting amount of a compound according to claim 1.

* * * * *